United States Patent
Wong et al.

(10) Patent No.: US 11,009,508 B2
(45) Date of Patent: May 18, 2021

(54) METHODS OF DIAGNOSING AND PROGNOSING LUNG CANCER

(71) Applicants: Dana-Farber Cancer Institute, Inc., Boston, MA (US); The University of North Carolina at Chapel Hill, Chapel Hill, NC (US); The General Hospital Corporation, Boston, MA (US); Board of Regents of the University of Texas System, Austin, TX (US)

(72) Inventors: Kwok-Kin Wong, Arlington, MA (US); Bruce E. Johnson, Brookline, MA (US); Pasi A. Janne, Needham, MA (US); Hongbin Ji, Boston, MA (US); Nabeel Bardeesy, Boston, MA (US); Norman E. Sharpless, Chapel Hill, NC (US); Diego H. Castrillon, Austin, TX (US)

(73) Assignees: Dana-Farber Cancer Institute, Inc., Boston, MA (US); The University of North Carolina at Chapel Hill; The General Hospital Corporation, Boston, MA (US); Board of Regents of the University of Texas System, Austin, TX (US)

(*) Notice: Subject to any disclaimer, the term of this patent is extended or adjusted under 35 U.S.C. 154(b) by 55 days.

(21) Appl. No.: 16/255,239

(22) Filed: Jan. 23, 2019

(65) Prior Publication Data
US 2019/0145977 A1 May 16, 2019

Related U.S. Application Data

(63) Continuation of application No. 12/449,404, filed as application No. PCT/US2008/052920 on Feb. 4, 2008, now abandoned.

(60) Provisional application No. 60/888,190, filed on Feb. 5, 2007.

(51) Int. Cl.
*G01N 33/574* (2006.01)

(52) U.S. Cl.
CPC .............. *G01N 33/57423* (2013.01); *G01N 2333/9121* (2013.01)

(58) Field of Classification Search
CPC ............. G01N 33/57423; G01N 2333/9121
See application file for complete search history.

(56) References Cited

U.S. PATENT DOCUMENTS

2011/0119776 A1  5/2011  Wong et al.

FOREIGN PATENT DOCUMENTS

WO   WO-2005023202 A2 *  3/2005  ........... G01N 33/574

OTHER PUBLICATIONS

Alessi et al. Annu Rev Biochem. 2006. 75:137-163 (Year: 2006).*
Gridelli et al. The Oncologist. 2008. 13:139-147. (Year: 2008).*
Sanchez-Cespedes. Familial Cancer. 2011. 10:447-453. (Year: 2011).*
Blanco et al. Hum Mutat. 2009. 30(8): 1199-1206. (Year: 2009).*
Mahoney et al. British Journal of Cancer. 2009. 100:370-375. (Year: 2009).*
Avizienyte et al., "LKB1 Somatic Mutations in Sporadic Tumors." *Am. J. Pathol.* 154:677-681 (1999).
Bardeesy et al., "Loss of the Lkb1 tumour suppressor provokes intestinal polyposis but resistance to transformation." *Nature.* 419(6903):162-167 (2002).
Bolstad et al., "A Comparison of Normalization Methods for High Density Oligonucleotide Array Data Based on Variance and Bias." *Bioinformatics.* 19(2):185-193 (2003).
Boudeau et al., "LKB1, a protein kinase regulating cell proliferation and polarity." *FEBS Letters.* 546:159-165 (2003).
Brugarolas et al., "Regulation of mTOR function in response to hypoxia by REDD1 and TSC1/TSC2 tumor suppressor complex." *Genes & Development.* 18(23):2893-2904 (2004).
Camilo et al., "Expression of p64, Keratin 5/6, Keratin 7, and Surfactant-A in Non-Small Cell Lung Carcinomas." *Hum. Pathol.* 37:542-546 (2006).
Carretero et al., "Dysfunctional AMPK Activity, Signalling Through mTOR and Survival in Response to Energetic Stress in LKB1-Deficient Lung Cancer." *Oncogene.* 26:1616-1625 (2007).
Carretero et al., "Novel and Natural Knockout Lung Cancer Cell Lines for the LKB1/STK11 Tumor Suppressor Gene." *Oncogene.* 23:4037-4040 (2004).
Chenette, "LbK1 loss poses a triple threat," Retrieved on Apr. 2, 2014 from the Internet: http://www.signaling-gateway.org/update/Updates/200708/su-0708-2.html, 7 pages.
Corradetti et al., "Regulation of the TSC Pathway by LKB1: Evidence of a Molecular Link Between Tuberous Sclerosis Complex and Peutz-Jeghers Syndrome." *Genes Dev.* 18:1533-1538 (2004).
Dennis et al., "David: Database for Annotation, Visualization, and Integrated Discovery." *Genome Biol.* 4:R60 (2003).
Dermer, "Another Anniversary for the War on Cancer." *Biotechnology.* 12:320 (1994).
Eberhard et al., "Mutations in the Epidermal Growth Factor Receptor and in KRAS are Predictive and Prognostic Indicators in Patients With Non-Small-Cell Lung Cancer Treated With Chemotherapy Alone and in Combination With Erlotinib." *Journal of Clinical Oncology.* 23(25):5900-5909 (2005).
Eisen et al., "Cluster Analysis and Display of Genome-Wide Expression Patterns." *PNAS.* 95(25):14863-14868 (1998).
eMICE. Retrieved on Apr. 22, 2013 from the Internet: http://emice.nci.nih.gov/aam, 2 pages.
Entius et al., "Molecular Genetic Alterations in Hamartomatous Polyps and Carcinomas of Patients with Peutz-Jeghers Syndrome." *J. Clin. Pathol.* 54:126-131 (2001).
Entius et al., "Peutz-Jeghers Polyps, Dysplasia, and K-ras Codon 12 Mutations." *Gut.* 41:320-322 (1997).

(Continued)

*Primary Examiner* — Joseph G. Dauner
(74) *Attorney, Agent, or Firm* — Baker Donelson

(57) ABSTRACT

The present invention provides methods of detecting cancer using biomarkers.

15 Claims, 13 Drawing Sheets

Specification includes a Sequence Listing.

(56) References Cited

OTHER PUBLICATIONS

Fernandez et al., "Distinctive Gene Expression of Human Lung Adenocarcinomas Carrying LKB1 Mutations." *Oncogene.* 23:5084-5091 (2004).
Fisher et al., "Induction and Apoptotic Regression of Lung Adenocarcinomas by Regulation of a K-Ras Transgene in the Presence and Absence of Tumor Suppressor Genes." *Genes Dev.* 15:3249-3262 (2001).
Forbes et al., "Cosmic 2005." *Br. J. Cancer.* 94:318-322 (2006).
Gruber et al., "Pathogenesis of Adenocarcinoma in Peutz-Jeghers Syndrome." *Cancer Res.* 58:5267-5270 (1998).
Hahn et al., "Comparative Oncology of Lung Tumors." *Toxicologic Pathology.* 35:130-135 (2007).
Hardie, "The AMP-activated protein kinase pathway—new players upstream and downstream." *Journal of Cell Science.* 117:5479-5487 (2004).
Hardie et al., "New Roles for LKB1→AMPK Pathway." *Curr. Opin. Cell Biol.* 17:167-173 (2005).
Hearle et al., "Frequency and Spectrum of Cancers in the Peutz-Jeghers Syndrome." *Clin. Cancer Res.* 12:3209-3215 (2006).
International Search Report dated May 11, 2009, for Application No. PCT/US2008/052920, filed on Feb. 4, 2008, 7 pages.
Irizarry et al., "Exploration, Normalization, and Summaries of High Density Oligonucleotide Array Probe Level Data." *Biostatistics.* 4(2):249-264 (2003).
Irizarry et al., "Summaries of Affymetrix GeneChip Probe Level Data." *Nucl. Acids Res.* 31(4):e15 (2003).
Jackson et al., "Analysis of Lung Tumor Initiation and Progression Using Conditional Expression of Oncogenic K-ras." *Genes Dev.* 15:3243-3248 (2001).
Jackson et al., "The Differential Effects of Mutant p53 Alleles on Advanced Murine Lung Cancer." *Cancer Res.* 65:10280-10288 (2005).
Ji et al., "K-ras Activation Generates an Inflammatory Response in Lung Tumors." *Oncogene.* 25:2105-2112 (2006).
Ji et al., "The Impact of Human EGFR Kinase Domain Mutations on Lung Tumorigenesis and in vivo Sensitivity to EGFR-Targeted Therapies." *Cancer Cell.* 9:485-495 (2006).
Ji et al., "LKB1 modulates lung cancer differentiation and metastasis." *Nature.* 448(7155):807-810 (2007).
Johnson et al., "Somatic activation of the K-ras oncogene causes early onset lung cancer in mice." *Nature.* 410:1111-1116 (2001).
Jonkers et al., "Synergistic Tumor Suppressor Activity of BRCA2 and p53 in a Conditional Mouse Model for Breast Cancer." *Nat. Genet.* 29:418-425 (2001).
Karuman et al., "Peutz-Jegher Gene Product LKB1 is a Mediator of p53-Dependent Cell Death." *Mol. Cell.* 7:1307-1319 (2001).
Koivunen et al., "Mutations in the LKB1 tumour suppressor are frequently detected in tumours from Caucasian but not Asian lung cancer patients." *British Journal of Cancer.* 99:245-252 (2008).
Kottakis et al., "LKB1 suppresses melanoma metastasis: the answer is YES." *Pigment Cell and Melanoma Research.* 25(6):716-718 (2012).
Krishnamurthy et al., "INK4a/ARF Expression is a Biomarker of Aging." *J. Clin. Invest.* 114:1299-1307 (2004).
Kwon & Berns, "Mouse models for lung cancer." *Molecular Oncology.* 7:165-177 (2013).
Launonen et al., "No Evidence of Peutz-Jeghers Syndrome Gene *LKB1* Involvement in Left-sided Colorectal Carcinomas." *Cancer Research.* 60:546-548 (2000).
Launonen, "Mutations in the Human LKB1/STK11 Gene." *Hum. Mutat.* 26(4):291-297 (2005).
Lung Cancer 101. Retrieved on Apr. 22, 2013 from the Internet: http://www.lungcancer.org/find_information/publications/163-lung_cancer_101/268-types_and_staging>, 2 pages.
Mahoney et al., "Human non-small cell lung cancer (NSCLC) cell lines with inactivated LKB1 and KRAS mutations are sensitive to MEK inhibition." *European Journal of Cancer.* 6(9):32-33 (2008).
Mantripragada & Khurshid, "Targeting genomic alterations in squamous cell lung cancer." *Frontiers in Oncology.* 3:1-9 (2013).

Marcus & Zhou, "LKB1 regulated pathways in lung cancer invasion and metastasis." *J Thorac Oncol.* 5(12):1883-1886 (2010).
Matsumoto, S. et al., "Prevalence and specificity of LKB1 genetic alterations in lung cancers." *Oncogene.* 26:5911-5918 (2007).
Mehenni et al., "Loss of LKB1 Kinase Activity in Peutz-Jeghers Syndrome, and Evidence for Allelic and Locus Heterogeneity." *Am. J. Hum. Genet.* 63:1641-1650 (1998).
Meuwissen et al., "Induction of Small Cell Lung Cancer by Somatic Inactivation of Both Trp53 and Rb1 in a Conditional Mouse Model." *Cancer Cell.* 4:181-189 (2003).
Meuwissen et al., "Mouse Model for Lung Tumorigenesis Through Cre/lox Controlled Sporadic Activation of the K-Ras Oncogene." *Oncogene.* 20:6551-6558 (2001).
Meuwissen & Berns, "Mouse models for human lung cancer." *Genes & Development.* 19:643-664 (2005).
MGI—Lee Silver's Mouse Genetics. Retrieved on Apr. 22, 2013 from the Internet: <http://www.informatics.jax.org/silver/frames/frame1-3.shtml>, 5 pages.
Olilla & Makela, "The tumor suppressor kinase LKB1: lessons from mouse models." *Journal of Molecular Cell Biology.* 0:1-11 (2011).
Onozato et al., "LKB1 gene mutations in Japanese lung cancer patients." *Cancer Science.* 98(11):1747-1751 (2007).
Pao et al., *KRAS* Mutations and Primary Resistance of Lung Adenocarcinomas to Gefitinib or Erlotinib. *PLoS Medicine.* 2(1):e17 (2005).
Patek et al., "Mutationally activated K-ras 4A and 4B both mediate lung carcinogenesis." *Experimental Cell Research.* 314(5):1105-1114 (2007).
Raponi et al., "Gene Expression Signatures for Predicting Prognosis of Squamos Cell and Adenocarcinomas of the Lung." *Cancer Res.* 66:7466-7472 (2006).
Sanchez-Cespedes et al., "Inactivation of LKB1/STK11 is a common event in adenocarcinomas of the lung." *Cancer Research.* 62:3659-3662 (2002).
Schneider et al., "Genetic alterations in pancreatic carcinoma." *Molecular Cancer.* 2(1):15 (2003).
Serrano et al., "Role of the INK4a Locus in Tumor Suppression and Cell Mortality." *Cell.* 85:27-37 (1996).
Sharpless et al., "Loss of p16INK4a with Retention of p19Arf Predisposes Mice to Tumorigenesis." *Nature.* 413:86-91 (2001).
Sharpless et al., "The Differential Impact of p16INK4a or p19ARF Deficiency on Cell Growth and Tumorigenesis." *Oncogene.* 23:379-385 (2004).
Shaw et al., "The LKB1 Tumor Suppressor Negatively Regulates mTOR Signaling." *Cancer Cell.* 6:91-99 (2004).
Sobottka et al., "Frequent loss of heterozygosity at the 19p13.3. locus without LKB1/STK11 mutations in human carcinoma metastases to the brain." *Journal of Neuro-Oncology.* 49:187-195 (2000).
Strazisar et al., "Somatic Alterations of the Serine/Threonine Kinase LKB1 Gene in Squamous Cell (SCC) and Large Cell (LCC) Lung Carcinoma." *Cancer Investigation.* 27:407-416 (2009).
Sun et al., "Targeting mTOR Signaling for Lung Cancer Therapy." *J. Thorac. Oncol.* 1(2):109-111 (2006).
Swinkels et al., "Early Detection of Leptomeningeal Metastasis by PCR Examination of Tumor-derived K-ras DNA in Cerebrospinal Fluid." *Clinical Chemistry.* 46(1):132-133 (2000).
Takahashi et al., "A novel germline mutation of the LKB1 gene in a patient with Peutz-Jeghers syndrome with early-onset gastric cancer." *J Gastroenterol.* 39:1210-1214 (2004).
Thisted, "What is a P-value?" The University of Chicago, pp. 1-6 (1998).
Tiainen et al., "Growth Arrest by the LKB1 Tumor Suppressor: Induction of p21WAF1/CIP1." *Hum. Mol. Genet.* 11(13):1497-1504 (2002).
Tuveson & Jacks, "Modeling human lung cancer in mice: similarities and shortcomings." *Oncogene.* 18:5318-5324 (1999).
Upadhyay et al., "LKB1/STK11 Suppresses Cyclooxygenase-2 Induction and Cellular Invasion Through PEA3 in Lung Cancer." *Cancer Res.* 66:7870-7879 (2006).
Wang et al., Germline mutations of the LKB1 (STK11) gene in Peutz-Jeghers patients. *J Med Genet.* 36:365-368 (1999).

(56) References Cited

OTHER PUBLICATIONS

Xie et al., "Identification of the Serine 307 of LKB1 as a Novel Phosphorylation Site Essential for Its Nucleocytoplasmic Transport and Endothelial Cell Angiogenesis." *Molecular and Cellular Biology.* 29(13):3582-3596 (2009).

Ylikorkala et al., "Mutations and impaired function of LKB1 in familial and non-familial Peutz-Jeghers syndrome and a sporadic testicular cancer." *Human Molecular Genetics.* 8(1):45-51 (1999).

Young et al., "Differential Expression and Biodistribution of Cytokeratin 18 and Desmoplakins in Non-Small Cell Lung Carcinoma Subtypes." *Lung Cancer.* 36:133-141 (2002).

Zhong et al., "LBK1 Mutation in Large Cell Carcinoma of the Lung." *Lung Cancer.* 53:285-294 (2006).

* cited by examiner

METHODS OF DIAGNOSING AND PROGNOSING LUNG CANCER

RELATED APPLICATIONS

This application is a continuation of U.S. application Ser. No. 12/449,404, filed on Jan. 31, 2011, which is a national stage application, filed under 35 U.S.C. § 371, of international Application No. PCT/US2008/052920, filed on Feb. 4, 2008, which claims the benefit of U.S. Application No. 60/888,190, filed Feb. 5, 2007, the contents of each of which are incorporated herein by reference in their entireties.

FIELD OF THE INVENTION

The invention relates generally to detecting cancer.

INCORPORATION-BY-REFERENCE OF SEQUENCE LISTING

The contents of the textile file named "DFCI-045C01US_SeqList.txt", which was created on Jan. 18, 2019 and is 9 KB in size, are hereby incorporated by reference in their entirety.

BACKGROUND OF THE INVENTION

Non-small cell lung cancer (NSCLC) is the most common and lethal cancer world-wide. At least three major histologies of NSCLC are described: squamous carcinoma (48%), large cell carcinoma (12%) and adenocarcinoma (40%). The standard treatment for these patients is systemic chemotherapy. However, systemic chemotherapy has modest efficacy and has not greatly prolonged the median survival (8-12 months) or 5-year survival rates (2%) in these patients. Although these sub-types differ markedly in histologic appearance and gene expression, each is highly lethal, and until recently, little clinical distinction has been made among those entities.

It is anticipated that a better understanding of the molecular mechanisms involved in the initiation and progression lung tumorigenesis—as well as the impact of environmental exposures on lung carcinogenesis—would help guide the development of better and more targeted lung cancer therapeutics as well as potential prevention strategies. The recent identification of the oncogenic kinase domain mutations in the epidermal growth factor receptor (EDFR) in human lung adenocarcinomas and their association with sensitivity to small molecule EGFR kinase inhibitors such as gefitinib and erlotinib further support that the molecular understanding of the mechanisms involved in lung tumorigenesis will lead to advances in patient screening, development of better targeted therapeutics, and identification of patients who are best suited for each type of targeted treatment. Activating K-RAS, EGFR, and BRAF mutations comprise the most common oncogenic mutations in human NSCLC. However, their interaction with other concurrent tumor suppressor loss is not well understood.

SUMMARY OF THE INVENTION

The invention provides biological markers for monitoring, diagnosing and prognosing lung cancer.

In one aspect the invention provides a method for determining the aggressiveness of a lung cancer in a mammal, e.g. human, by determining in a test sample from the mammal, the presence or absence of Lkb1 expression or activity and correlating the presence or absence with aggressiveness of the lung cancer. The absence of Lkb1 expression or decrease of the activity of Lkb1 indicates the cancer is aggressive and/or metastatic. In contrast, the presence of intact Lkb1, e.g. non-mutated indicates the cancer is not aggressive. The test sample is for example a tumor biopsy.

Optionally, the method includes determining the presence or absence of an additional tumor biomarker such as determining the presence or absence of a mutation in K-ras, EGFR or BRAF.

Also included in the invention is a method of assessing the efficacy of an m-TOR inhibitor for treating or inhibiting the growth of lung cancer in a patient, by detecting inactivation of Lkb1 gene expression in a lung cancer tumor from a subject. Inactivation of Lkb1 gene expression in the lung cancer tumor indicates treatment with an m-TOR inhibitor is efficacious.

Lung cancer is diagnosed or a predisposition to developing lung cancer in a subject by determining a level of expression of a lung cancer-associated gene in a patient derived tissue sample. By LC associated gene is meant a gene that is characterized by a level of expression which differs in a cell obtained from a lung cancer cell compared to a normal cell. A normal cell is one obtained from lung tissue. A LC-associated gene includes for example LC 1-461. An alteration, e.g., increase of the level of expression of the gene compared to a normal control level of the gene indicates that the subject suffers from or is at risk of developing lung cancer.

Alternatively, expression of a panel of LC-associated genes in the sample is compared to a LC control level of the same panel of genes. By LC control level is meant the expression profile of the LC-associated genes found in a population suffering from lung cancer.

Gene expression is increased or decreased 10%, 25%, 50% compared to the control level. Alternately, gene expression is increased or decreased 1, 2, 5 or more fold compared to the control level. Expression is determined by detecting hybridization, e.g., on a chip, of a LC-associated gene probe to a gene transcript of the patient-derived tissue sample.

The patient derived tissue sample is any tissue from a test subject, e.g., a patient known to or suspected of having lung cancer. For example, the tissue contains a sputum, blood, serum, plasma or lung cell.

The invention also provides a LC reference expression profile of a gene expression level of two or more of PRC 1-461.

The invention further provides a kit with a detection reagent which binds to two or more LC nucleic acid sequences or which binds to a gene product encoded by the nucleic acid sequences. Also provided is an array of nucleic acids that binds to two or more LC nucleic acids.

In another aspect, the invention includes a transgenic animal whose genome contains a mutant K-ras oncogene, e.g. G12D mutation and at least one Lkb1null allele. The transgenic animal constitutively expresses a mutated K-ras protein in at least one tissue and exhibits accelerated development of a lung tumor. Optionally, the animal is homozygous null for Lkb1.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION OF THE INVENTION

Figure 1A:
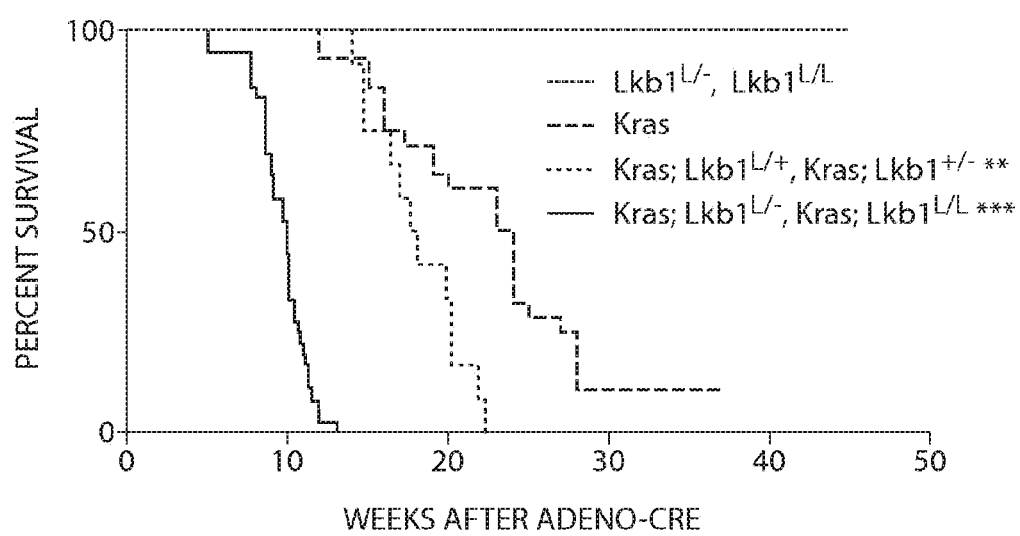
FIG. 1A is a line graph showing the tumor-free survival of mice treated with adeno-CRE. Cohort consists of K-ras (n=26), K-ras Lkb1$^{+/-}$ (n=27), K-ras Lkb1$^{L/L\ or\ L/-}$ (n=56), and Lkb1$^{-/-}$ (n=15). P<0.002 for pair-wise comparison between K-ras and K-ras Lkb1$^{+/-}$, and p<0.0001 for pair-wise comparison between K-ras and K-ras Lkb1$^{-/-}$.

The invention is based upon the discovery of biomarkers for the detection and assessment of cancer. Specifically, it has been shown that a somatic defficency in the kinase, Lkb1 accelerates the development of lung tumerigenesis. More specifically, Lkb1 deficiency in the setting of K-ras$^{G12D}$ mutation (K-rasLkb1$^{L/L}$) was associated with decreased tumor latency and increased tumor aggressiveness including metastasis. Furthermore, tumors from K-ras Lkb1$^{L/L}$ mice demonstrated mice exhibit the full range of histologic subtypes (including squamous, adenosquamous, and large-cell) that arise in humans, whereas K-ras$^{G12D}$ mutation, Ink4a/Arf inactivation, or p53 inactivation alone or in combination result only in adenocarcinoma. These findings suggest that, unexpectedly, Lkb1 influences cell differentiation in addition to its roles in the suppression of cell growth. Experiments in vitro demonstrate that LKB1 suppresses lung tumorigenesis and progression through both p16$^{INK4a}$-ARF-p53 dependent and independent mechanisms. These data indicate that LKB1 regulates lung tumor progression by controlling multiple aspects of cell growth and differentiation.

Additionally, a comprehensive microarray analysis was performed on K-ras induced lung tumors to identify commonly over-expressed genes. Four hundred and sixty one genes were up-regulated.

The genes whose expression levels are modulated (i.e., increased) in lung cancer are summarized in Table A and are collectively referred to herein as "lung cancer-associated genes", "LC nucleic acids" or "LC polynucleotides" and the corresponding encoded polypeptides are referred to as "LC polypeptides" or "LC proteins," Unless indicated otherwise, "LC" is meant to refer to any of the sequences disclosed herein. (e.g., LC 1-461). The genes have been previously described and are presented along with a database accession number.

Accordingly, the invention provides methods of detecting and evaluating the agressivness of lung cancer in a subject by determining the presence or absence of Lkb1. In addition, the differntially expressed genes identified herein are used for diagnositic purposes and to develop gene targeted therapeutic approaches to inhibiting lung cancer.

TABLE A

| LC Assignment | CLID | NAME |
|---|---|---|
| 1 | Tgfb2 | Tgfb2 ‖ transforming growth factor, beta 2 |
| 2 | Zfp36l1 | Zfp36l1 ‖ zinc finger protein 36, C3H type-like 1 |
| 3 | Fusip1 | Fusip1 ‖ FUS interacting protein (serine-arginine rich) 1 |
| 4 | Abcc9 | Abcc9 ‖ ATP-binding cassette, sub-family C (CFTR/MRP), member 9 |
| 5 | Rnf130 | Rnf130 ‖ ring finger protein 130 |
| 6 | Nfkbie | Nfkbie ‖ nuclear factor of kappa light polypeptide gene enhancer in B-cells inhibitor, epsilon |
| 7 | Ppargc1b | Ppargc1b ‖ peroxisome proliferative activated receptor, gamma, coactivator 1 beta |
| 8 | Srrm2 | Srrm2 ‖ serine/arginine repetitive matrix 2 |
| 9 | Thrap3 | Thrap3 ‖ thyroid hormone receptor associated protein 3 |
| 10 | Smarca2 | Smarca2 ‖ SWI/SNF related, matrix associated, actin dependent regulator of chromatin, subfamily a, member 2 |
| 11 | Tmcc3 | Tmcc3 ‖ transmembrane and coiled coil domains 3 |
| 12 | Fez2 | Fez2 ‖ fasciculation and elongation protein zeta 2 (zygin II) |
| 13 | Suv39h1 | Suv39h1 ‖ suppressor of variegation 3-9 hoinolog 1 (*Drosophila*) |
| 14 | Klf6 | Klf6 ‖ Kruppel-like factor 6 |
| 15 | Col7a1 | Col7a1 ‖ procollagen, type VII, alpha 1 |
| 16 | Tspan17 | Tspan17 tetraspanin 17 |
| 17 | Gats | Gats ‖ opposite strand transcription unit to Stag3 |
| 18 | Tiparp | Tiparp ‖ TCDD-inducible poly(ADP-ribose) polymerase |
| 19 | Sfrs8 | Sfrs8 ‖ splicing factor, arginine/serine-rich 8 |
| 20 | Slc6a8 | Slc6a8 ‖ solute carrier family 6 (neurotransmitter transporter, creatine), member 8 |
| 21 | Trip12 | Trip12 ‖ thyroid hormone receptor interactor 12 |
| 22 | Wdsub1 | Wdsub1 ‖ WD repeat, SAM and U-box domain containing 1 |
| 23 | Vdr | Vdr ‖ vitamin D receptor |
| 24 | Ece1 | Ece1 ‖ endothelin converting enzyme 1 |
| 25 | Uxt | Uxt ‖ ubiquitously expressed transcript |
| 26 | Zdhhc4 | Zdhhc4 ‖ zinc finger, DHHC domain containing 4 |
| 27 | Ndn | Ndn /// Pctk1 ‖ necdin /// PCTAIRE-motif protein kinase 1 |
| 28 | 6330549H03Rik | 6330549H03Rik ‖ RIKEN cDNA 6330549H03 gene |
| 29 | Rab15 | Rab15 ‖ RAB15, member RAS oncogene family |
| 30 | Arf6 | Arf6 ‖ ADP-ribosylation factor 6 |
| 31 | Dnase1l1 | Dnase1l1 ‖ deoxyribonuclease 1-like 1 |
| 32 | 1190002N15Rik | 1190002N15Rik ‖ RIKEN cDNA 1190002N15 gene |
| 33 | Clic4 | Clic4 ‖ chloride intracellular channel 4 (mitochondrial) |
| 34 | Txnip | Txnip ‖ thioredoxin interacting protein |
| 35 | Pim3 | Pim3 ‖ proviral integration site 3 |
| 36 | Grin3b | Grin3b ‖ glutamate receptor, ionotropic, NMDA3B |
| 37 | Pscd3 | Pscd3 ‖ pteckstrin homology, Sec7 and coiled-coil domains 3 |
| 38 | Macf1 | Macf1 ‖ microtubule-actin crosslinking factor 1 |
| 39 | Pctk1 | Pctk1 ‖ PCTAIRE-motif protein kinase 1 |
| 40 | Lyn | Lyn /// LOC676654 ‖ Yamaguchi sarcoma viral (v-yes-1) oncogene homolog /// similar to Yamaguchi sarcoma viral (v-yes-1) oncogene homolog |
| 41 | Tspyl1 | Tspyl1 ‖ testis-specific protein, Y-encoded-like 1 |
| 42 | Fbxw4 | Fbxw4 ‖ F-box and WD-40 domain protein 4 |
| 43 | C80012 | C80012 ‖ expressed sequence C80012 |
| 44 | Col16a1 | Col16a1 ‖ procollagen, type XVI, alpha 1 |
| 45 | Sv2a | Sv2a ‖ synaptic vesicle glycoprotein 2 a |
| 46 | Gm672 | Gm672 ‖ Gene model 672, (NCBI) |
| 47 | Centg2 | Centg2 ‖ centaurin, gamma 2 |
| 48 | Ahdc1 | Ahdc1 ‖ AT hook, DNA binding motif, containing 1 |
| 49 | Olfr65 | Olfr65 ‖ olfactory receptor 64 |
| 50 | 9130404D08Rik | 9130404D08Rik ‖ RIKEN cDNA 9130404D08 gene |
| 51 | Lgals8 | Lgals8 ‖ lectin, galactose binding, soluble 8 |

TABLE A-continued

| LC Assignment | CLID | NAME |
|---|---|---|
| 52 | Slc6a6 | Slc6a6 \|\| solute carrier family 6 (neurotransmitter transporter, taurine), member 6 |
| 53 | C79248 | C79248 \|\| expressed sequence C79248 |
| 54 | Per3 | Per3 \|\| period homolog 3 (*Drosophila*) |
| 55 | Nisch | Nisch \|\| nischarin |
| 56 | Mylip | Mylip \|\| myosin regulatory light chain interacting protein |
| 57 | Abca1 | Abca1 \|\| ATP-binding cassette, sub-family A (ABC1), member 1 |
| 58 | Lfng | Lfng \|\| lunatic fringe gene homolog (*Drosophila*) |
| 59 | Pitpnm1 | Pitpnm1 \|\| phosphatidylinositol membrane-associated 1 |
| 60 | Jak2 | Jak2 \|\| Janus kinase 2 |
| 61 | 4732495E13Rik | 4732495E13Rik \|\| RIKEN cDNA 4732495E13 gene |
| 62 | Pscd1 | Pscd1 \|\| pleckstrin homology, Sec7 and coiled-coil domains 1 |
| 63 | Tpp1 | Tpp1 \|\| tripeptidyl peptidase I |
| 64 | Rbm7 | Rbm7 \|\| RNA binding motif protein 7 |
| 65 | Drctnnb1a | Drctnnb1a \|\| down-regulated by Ctnnb1, a |
| 66 | Mospd1 | Mospd1 \|\| motile sperm domain containing 1 |
| 67 | Huwe1 | Huwe1 \|\| HECT, UBA and WWE domain containing 1 |
| 68 | Cfl2 | Cfl2 \|\| cofilin 2, muscle |
| 69 | Birc3 | Birc3 \|\| baculoviral IAP repeat-containing 3 |
| 70 | 2410005O16Rik | 2410005O16Rik \|\| RIKEN cDNA 2410005O16 gene |
| 71 | Zc3h12c | Zc3h12c \|\| zinc finger CCCH-type containing 12C |
| 72 | Syk | Syk \|\| spleen tyrosine kinase |
| 73 | Adamts15 | Adamts15 \|\| a disintegrin-like and metallopeptidase (reprolysin type) with thrombospondin type 1 motif, 15 |
| 74 | Npl | Npl \|\| N-acetylneuraminate pyruvate lyase |
| 75 | — | —\|\| Transcribed locus |
| 76 | Mef2d | Mef2d \|\| myocyte enhancer factor 2D |
| 77 | Cdc42bpa | Cdc42bpa \|\| Cdc42 binding protein kinase alpha |
| 78 | Eln | Eln \|\| elastin |
| 79 | Serpina3n | Serpma3n \|\| serine (or cysteine) peptidase inhibitor, clade A, member 3N |
| 80 | Lox | Lox \|\| lysyl oxidase |
| 81 | Cias1 | Cias1 \|\| cold autoinflammatory syndrome 1 homolog (human) |
| 82 | Gdpd3 | Gdpd3 \|\| glycerophosphodiester phosphodiesterase domain containing 3 |
| 83 | H2-K1 | H2-K1 \|\| Histocompatibility 2, K1, K region |
| 84 | Clasp2 | Clasp2 \|\| CLIP associating protein 2 |
| 85 | Cnnm3 | Cnnm3 \|\| cyclin M3 |
| 86 | Nfia | Nfia \|\| nuclear factor I/A |
| 87 | 9430029L20Rik | 9430029L20Rik \|\| RIKEN cDNA 9430029L20 gene |
| 88 | Pi4k2b | Pi4k2b \|\| phosphatidylinositol 4-kinase type 2 beta |
| 89 | Ptger1 | Ptger1 \|\| Prostaglandin E receptor 1 (subtype EP1) |
| 90 | Leng8 | Leng8 \|\| leukocyte receptor cluster (LRC) member 8 |
| 91 | Cables1 | Cables1 /// LOC635753 \|\| Cdk5 and Abl enzyme substrate 1 /// similar to Cdk5 and Abl enzyme substrate 1 |
| 92 | Sorbs3 | Sorbs3 \|\| sorbin and SH3 domain containing 3 |
| 93 | Adipor1 | Adipor1 \|\| adiponectin receptor 1 |
| 94 | LOC547343 | LOC547343 \|\| similar to H-2 class I histocompatibility antigen, L-D alpha chain precursor |
| 95 | H2-D1 | H2-D1 \|\| histocompatibility 2, D region locus 1 |
| 96 | H2-D1 | H2-D1 /// H2-L /// LOC547343 /// LOC636948 \|\| histocompatibility 2, D region locus 1 /// histocompatibility 2, D region /// similar to H-2 class I histocompatibility antigen, L-D alpha chain precursor /// similar to H-2 class I histocompatibility antigen, D-B alpha chain precursor (H-2D(B)) |
| 97 | H2-L | H2-L \|\| histocompatibility 2, D region |
| 98 | 2310043N10Rik | 2310043N10Rik \|\| RIKEN cDNA 2310043N10 gene |
| 99 | Per1 | Per1 \|\| period homolog 1 (*Drosophila*) |
| 100 | Slc24a3 | Slc24a3 \|\| solute carrier family 24 (sodium/potassium/calcium exchanger), member 3 |
| 101 | Slco3a1 | Slco3a1 \|\| solute carrier organic anion transporter family, member 3a1 |
| 102 | Epb4.1 | Epb4.1 \|\| erythrocyte protein band 4.1 |
| 103 | Emilin1 | Emilin1 \|\| elastin microfibril interfacer 1 |
| 104 | Usf2 | Usf2 \|\| upstream transcription factor 2 |
| 105 | Trak1 | Trak1 \|\| trafficking protein, kinesin binding |
| 106 | Ctsb | Ctsb \|\| cathepsin B |
| 107 | Man2b1 | Man2b1 \|\| mannosidase 2, alpha B1 |
| 108 | Adrbk1 | Adrbk1 \|\| adrenergic receptor kinase, beta 1 |
| 109 | BC018473 | BC018473 \|\| cDNA sequence BC018473 |
| 110 | Setdb1 | Setdb1 \|\| SET domain, bifurcated 1 |
| 111 | Zxdc | Zxdc \|\| ZXD family zinc finger C |
| 112 | Cetn1 | Cetn1 \|\| centrin 1 |
| 113 | F2rl2 | F2rl2 \|\| coagulation factor II (thrombin) receptor-like 2 |
| 114 | Zfp346 | Zfp346 \|\| zinc finger protein 346 |
| 115 | Eps15l1 | Eps15l1 \|\| epidermal growth factor receptor pathway substrate 15-like 1 |
| 116 | Xpo4 | Xpo4 \|\| exportin 4 |
| 117 | Scly | Scly \|\| selenocysteine lyase |
| 118 | Tlr5 | Tlr5 \|\| toll-like receptor 5 |
| 119 | Chst12 | Chst12 \|\| carbohydrate sulfotransferase 12 |
| 120 | Sipa1 | Sipa1 \|\| signal-induced proliferation associated gene 1 |

TABLE A-continued

| LC Assignment | CLID | NAME |
|---|---|---|
| 121 | Samsn1 | Samsn1 ‖ SAM domain, SH3 domain and nuclear localization signals, 1 |
| 122 | Krt1-14 | Krt1-14 /// Krt1-17 ‖ keratin complex 1, acidic, gene 14 /// keratin complex 1, acidic, gene 17 |
| 123 | Fgr | Fgr ‖ Gardner-Rasheed feline sarcoma viral (Fgr) oncogene homolog |
| 124 | Scube1 | Scube1 ‖ signal peptide, CUB domain, EGF-like 1 |
| 125 | Unc5c | Unc5c ‖ unc-5 homolog C (*C. elegans*) |
| 126 | Mmp24 | Mmp24 ‖ matrix metallopeptidase 24 |
| 127 | Nxph3 | Nxph3 ‖ neurexophilin 3 |
| 128 | Stau1 | Stau1 ‖ staufen (RNA binding protein) homolog 1 (*Drosophila*) |
| 129 | Ddi2 | Ddi2 // Rsc1a1 ‖ DNA-damage inducible protein 2 /// regulatory solute carrier protein, family 1, member 1 |
| 130 | Pacs2 | Pacs2 ‖ phosphofurin acidic cluster sorting protein 2 |
| 131 | Rac2 | Rac2 ‖ RAS-related C3 botulinum substrate 2 |
| 132 | Impact | Impact ‖ imprinted and ancient |
| 133 | Trex1 | Trex1 ‖ three prime repair exonuclease 1 |
| 134 | Sp4 | Sp4 ‖ trans-acting transcription factor 4 |
| 135 | 2900002H16Rik | 2900002H16Rik ‖ RIKEN cDNA 2900002H16 gene |
| 136 | D930015E06Rik | D930015E06Rik ‖ RIKEN cDNA D930015E06 gene |
| 137 | Rbl2 | Rbl2 /// LOC635075 ‖ retinoblastoma-like 2 /// similar to retinobiastoma-like 2 |
| 138 | Parp8 | Parp8 ‖ poly (ADP-ribose) polymerase family, member 8 |
| 139 | Gnb4 | Gnb4 ‖ guanine nucleotide binding protein, beta 4 |
| 140 | Il1r1 | Il1r1 ‖ interleukin 1 receptor, type I |
| 141 | Gfm1 | Gfm1 ‖ G elongation factor, mitochondrial 1 |
| 142 | Vps11 | Vps11 ‖ vacuolar protein sorting 11 (yeast) |
| 143 | Epim | Epim ‖ epimorphin |
| 144 | Cd37 | Cd37 ‖ CD37 antigen |
| 145 | Map3k1 | Map3k1 ‖ mitogen activated protein kinase kinase kinase 1 |
| 146 | BC039093 | BC039093 ‖ cDNA sequence BC039093 |
| 147 | Tug1 | Tug1 ‖ taurine upregulated gene 1 |
| 148 | 4631426J05Rik | 4631426J05Rik ‖ RIKEN cDNA 4631426J05 gene |
| 149 | Grn | Grn ‖ granulin |
| 150 | Irf8 | Irf8 ‖ interferon regulatory factor 8 |
| 151 | Lycat | Lycat ‖ lysocardiolipin acyltransferase |
| 152 | Trps1 | Trps1 ‖ trichorhinophalangeal syndrome I (human) |
| 153 | Cysltr1 | Cysltr1 ‖ cysteinyl leukotriene receptor 1 |
| 154 | T2bp | T2bp ‖ Traf2 binding protein |
| 155 | Tm6sf1 | Tm6sf1 ‖ transmembrane 6 superfamily member 1 |
| 156 | Hdgfrp3 | Hdgfrp3 /// Tm6sf1 ‖ hepatoma-derived growth factor, related protein 3 /// transmembrane 6 superfamily member 1 |
| 157 | Il17ra | Il17ra ‖ interleukin 17 receptor A |
| 158 | Hal | Hal /// LOC638196 ‖ histidine ammonia lyase /// similar to Histidine ammonia-lyase (Histidase) |
| 159 | Map3k8 | Map3k8 ‖ mitogen activated protein kinase kinase kinase 8 |
| 160 | Cd300lf | Cd300lf ‖ CD300 antigen like family member F |
| 161 | Osbpl9 | Osbpl9 ‖ Oxysterol binding protein-like 9 |
| 162 | BC013712 | BC013712 ‖ cDNA sequence BC013712 |
| 163 | Igsf6 | Igsf6 ‖ immunoglobulin superfamily, member 6 |
| 164 | LOC676654 | LOC676654 ‖ similar to Yamaguchi sarcoma viral (v-yes-1) oncogene homolog |
| 165 | Prei4 | Prei4 ‖ preimplantation protein 4 |
| 166 | Cebpb | Cebpb ‖ CCAAT/enhancer binding protein (C/EBP), beta |
| 167 | Lst1 | Lst1 ‖ leukocyte specific transcript 1 |
| 168 | Siglecf | Siglecf ‖ sialic acid binding Ig-like lectin F |
| 169 | Ccr1 | Ccr1 ‖ chemokine (C-C motif) receptor 1 |
| 170 | Rassf5 | Rassf5 ‖ Ras association (RalGDS/AF-6) domain family 5 |
| 171 | Vamp4 | Vamp4 ‖ vesicle-associated membrane protein 4 |
| 172 | Lgals7 | Lgals7 ‖ lectin, galactose binding, soluble 7 |
| 173 | Rcbtb2 | Rcbtb2 ‖ regulator of chromosome condensation (RCC1) and BTB (POZ) domain containing protein 2 |
| 174 | Rhoq | Rhoq ‖ ras homolog gene family, member |
| 175 | Dcamkl1 | Dcamkl1 ‖ double cortin and calcium/calmodulin-dependent protein kinase-like 1 |
| 176 | Apob48r | Apob48r ‖ apolipoprotein B48 receptor |
| 177 | Slit2 | Slit2 ‖ slit homolog 2 (*Drosophila*) |
| 178 | Prkcb1 | Prkcb1 ‖ protein kinase C, beta 1 |
| 179 | Dmpk | Dmpk ‖ dystrophia myotonica-protein kinase |
| 180 | Lamc1 | Lamc1 ‖ laminin, gamma 1 |
| 181 | Rbpsuh | Rbpsuh ‖ recombining binding protein suppressor of hairless (*Drosophila*) |
| 182 | 2310016C16Rik | 2310016C16Rik ‖ RIKEN cDNA 2310016C16 gene |
| 183 | Cd19 | Cd19 ‖ CD19 antigen |
| 184 | Src | Src ‖ Rous sarcoma oncogene |
| 185 | Cyp2j6 | Cyp2j6 ‖ cytochrome P450, family 2, subfamily j, polypeptide 6 |
| 186 | Ikbkb | Ikbkb ‖ inhibitor of kappaB kinase beta |
| 187 | Pabpn1 | Pabpn1 ‖ poly(A) binding protein, nuclear 1 |
| 188 | Mll1 | Mll1 ‖ myeloid/lymphoid or mixed-lineage leukemia 1 |
| 189 | Wisp1 | Wisp1 ‖ WNT1 inducible signaling pathway protein 1 |

TABLE A-continued

| LC Assignment | CLID | NAME |
|---|---|---|
| 190 | Ptplad2 | Ptplad2 \|\| protein tyrosine phosphatase-like A domain containing 2 |
| 191 | Dkk2 | Dkk2 \|\| dickkopf homolog 2 (*Xenopus laevis*) |
| 192 | Ankrd1 | Ankrd1 \|\| ankyrin repeat domain 1 (cardiac muscle) |
| 193 | Ltbp3 | Ltbp3 \|\| latent transforming growth factor beta binding protein 3 |
| 194 | Sspn | Sspn \|\| sarcospan |
| 195 | Pfkfb3 | Pfkfb3 \|\| 6-phosphofructo-2-kinase/fructose-2,6-biphosphatase 3 |
| 196 | Tuba1 | Tuba1 \|\| tubulin, alpha 1 |
| 197 | Ptprs | Ptprs \|\| protein tyrosine phosphatase, receptor type, S |
| 198 | Dync1i2 | Dync1i2 \|\| dynein cytoplasmic 1 intermediate chain 2 |
| 199 | Lgals1 | Lgals1 \|\| lectin, galactose binding, soluble 1 |
| 200 | Akr1b7 | Akr1b7 \|\| aldo-keto reductase family 1, member B7 |
| 201 | Vim | Vim \|\| vimentin |
| 202 | Pdgfa | Pdgfa \|\| platelet derived growth factor, alpha |
| 203 | Postn | Postn \|\| periostin, osteoblast specific factor |
| 204 | Itgb5 | Itgb5 \|\| integrin beta 5 |
| 205 | Naalad2 | Naalad2 \|\| N-acetylated alpha-linked acidic dipeptidase 2 |
| 206 | Evl | Evl \|\| Ena-vasodilator stimulated phosphoprotein |
| 207 | Syt11 | Syt11 \|\| synaptotagmin XI |
| 208 | Sparc | Sparc \|\| secreted acidic cysteine rich glycoprotein |
| 209 | Pkd1 | Pkd1 \|\| polycystic kidney disease 1 homolog |
| 210 | Mark1 | Mark1 \|\| MAP/microtubule affinity-regulating kinase 1 |
| 211 | Chst2 | Chst2 \|\| carbohydrate sulfotransferase 2 |
| 212 | Ptpre | Ptpre \|\| protein tyrosine phosphatase, receptor type, E |
| 213 | Ncf4 | Ncf4 \|\| neutrophil cytosolic factor 4 |
| 214 | Mnt | Mnt \|\| max binding protein |
| 215 | 4632428N05Rik | 4632428N05Rik \|\| RIKEN cDNA 4632428N05 gene |
| 216 | Nid1 | Nid1 \|\| nidogen 1 |
| 217 | Apbb2 | Apbb2 \|\| amyloid beta (A4) precursor protein-binding, family B, member 2 |
| 218 | Stxbp1 | Stxbp1 \|\| syntaxin binding protein 1 |
| 219 | 4732435N03Rik | 4732435N03Rik \|\| RIKEN cDNA 4732435N03 gene |
| 220 | Pilrb | Pilrb \|\| paired immunoglobin-like type 2 receptor beta |
| 221 | Ank | Ank \|\| progressive ankylosis |
| 222 | Polb | Polb \|\| polymerase (DNA directed), beta |
| 223 | Unc5b | Unc5b \|\| unc-5 homolog B (*C. elegans*) |
| 224 | Inhba | Inhba \|\| inhibin beta-A |
| 225 | Cxxc5 | Cxxc5 \|\| CXXC finger 5 |
| 226 | Tnnt2 | Tnnt2 \|\| troponin T2, cardiac |
| 227 | Adamts4 | Adamts4 \|\| a disintegrin-like and metallopeptidase (reprolysin type) with thrombospondin type 1 motif, 4 |
| 228 | Mtap1b | Mtap1b \|\| microtubule-associated protein 1 B |
| 229 | Ints6 | Ints6 \|\| integrator complex subunit 6 |
| 230 | Aplp1 | Aplp1 \|\| amyloid beta (A4) precursor-like protein 1 |
| 231 | Muc5ac | Muc5ac \|\| mucin 5, subtypes A and C, tracheobronchial/gastric |
| 232 | Cdkn2b | Cdkn2b \|\| cyclin-dependent kinase inhibitor 2B (p15, inhibits CDK4) |
| 233 | Dbn1 | Dbn1 \|\| drebrin 1 |
| 234 | Pyy | Pyy \|\| peptide YY |
| 235 | Rnf38 | Rnf38 \|\| ring finger protein 38 |
| 236 | Bace1 | Bace1 \|\| beta-site APP cleaving enzyme 1 |
| 237 | 1200003C05Rik | 1200003C05Rik \|\| RIKEN cDNA 1200003C05 gene |
| 238 | Sh3glb1 | Sh3glb1 \|\| SH3-domain GRB2-like B1 (endophilin) |
| 239 | LOC637870 | LOC637870 \|\| similar to Nedd4 WW binding protein 4 |
| 240 | Tmepai | Tmepai \|\| transmembrane, prostate androgen induced RNA |
| 241 | Skil | Skil \|\| SKI-like |
| 242 | LOC637870 | LOC637870 /// LOC676013 \|\| similar to Nedd4 WW binding protein 4 /// similar to Nedd4 WW binding protein 4 |
| 243 | Slc25a30 | Slc25a30 \|\| solute carrier family 25, member 30 |
| 244 | Cpne1 | Cpne1 \|\| copine 1 |
| 245 | Mfge8 | Mfge8 \|\| milk fat globule-EGF factor 8 protein |
| 246 | Rnase1 | Rnase1 \|\| ribonuclease L (2',5'-oligoisoadenylate synthetase-dependent) |
| 247 | Mtap4 | Mtap4 \|\| microtubule-associated protein 4 |
| 248 | Tcf4 | Tcf4 \|\| transcription factor 4 |
| 249 | Raver1 | Raver1 \|\| ribonucleoprotein, PTB-binding 1 |
| 250 | Extl3 | Extl3 \|\| exostoses (multiple)-like 3 |
| 251 | Stx1a | Stx1a \|\| syntaxin 1A (brain) |
| 252 | Gtf2ird1 | Gtf2ird1 \|\| general transcription factor II I repeat domain-containing 1 |
| 253 | 5430405G24Rik | 5430405G24Rik \|\| RIKEN cDNA 5430405G24 gene |
| 254 | Fbln2 | Fbln2 \|\| fibulin 2 |
| 255 | Col5a3 | Col5a3 \|\| procollagen, type V, alpha 3 |
| 256 | Ppp2r4 | Ppp2r4 \|\| protein phosphatase 2A, regulatory subunit B (PR 53) |
| 257 | Tnip1 | Tnip1 \|\| TNFAIP3 interacting protein 1 |
| 258 | Cic | Cic \|\| capicua homolog (*Drosophila*) |
| 259 | C81521 | C81521 \|\| expressed sequence C81521 |
| 260 | AI450540 | AI450540 \|\| expressed sequence AI450540 |
| 261 | Rem2 | Rem2 \|\| rad and gem related GTP binding protein 2 |
| 262 | Cplx2 | Cplx2 \|\| complexin 2 |
| 263 | Igfbp4 | Igfbp4 \|\| insulin-like growth factor binding protein 4 |
| 264 | Vapb | Vapb \|\| vesicle-associated membrane protein, associated protein B and C |

TABLE A-continued

| LC Assignment | CLID | NAME |
|---|---|---|
| 265 | Slc6a6 | Slc6a6 ‖ Solute carrier family 6 (neurotransmitter transporter, taurine), member 6 |
| 266 | BC023055 | BC023055 ‖ cDNA sequence BC023055 |
| 267 | Sec61a2 | Sec61a2 ‖ Sec61, alpha subunit 2 (*S. cerevisiae*) |
| 268 | Ext2 | Ext2 ‖ exostoses (multiple) 2 |
| 269 | Crtap | Crtap ‖ cartilage associated protein |
| 270 | Pla1a | Pla1a ‖ phospholipase A1 member A |
| 271 | Ncor2 | Ncor2 ‖ nuclear receptor co-repressor 2 |
| 272 | Suhw4 | Suhw4 ‖ suppressor of hairy wing homolog 4 (*Drosophila*) |
| 273 | Ptn | Ptn ‖ pleiotrophin |
| 274 | Ltbp4 | Ltbp4 ‖ latent transforming growth factor beta binding protein 4 |
| 275 | Chd7 | Chd7 ‖ Chromodomain helicase DNA binding protein 7 |
| 276 | Nkd2 | Nkd2 ‖ naked cuticle 2 homolog (*Drosophila*) |
| 277 | Tgfb3 | Tgfb3 ‖ transforming growth factor, beta 3 |
| 278 | Ptpn1 | Ptpn1 ‖ protein tyrosine phosphatase, non-receptor type 1 |
| 279 | Nudt16 | Nudt16 ‖ nudix (nucleoside diphosphate linked moiety X)-type motif 16 |
| 280 | 4631408O11Rik | 4631408O11Rik ‖ RIKEN cDNA 4631408O11 gene |
| 281 | Gtf3c2 | Gtf3c2 ‖ general transcription factor IIC, polypeptide 2, beta |
| 282 | Arid1a | Arid1a /// LOC675933 ‖ AT rich interactive domain 1A (Swi1 like) /// similar to AT rich interactive domain 1A isoform a |
| 283 | B3gnt1 | B3gnt1 ‖ UDP-GlcNAc::betaGal beta-1,3-N-acetylglucosaminyltransferase 1 |
| 284 | Stk11ip | Stk11ip ‖ serine/threonine kinase 11 interacting protein |
| 285 | Rasal2 | Rasal2 ‖ RAS protein activator like 2 |
| 286 | Myst4 | Myst4 ‖ MYST histone acetyltransferase monocytic leukemia 4 |
| 287 | Tmlhe | Tmlhe ‖ trimethyllysine hydroxylase, epsilon |
| 288 | Camsap1 | Camsap1 ‖ calmodulin regulated spectrin-associated protein 1 |
| 289 | C80068 | C80068 ‖ expressed sequence C80068 |
| 290 | Plekhg2 | Plekhg2 ‖ pleckstrin homology domain containing, family G (with RhoGef domain) member 2 |
| 291 | Wipi1 | Wipi1 ‖ WD repeat domain, phosphoinositide interacting 1 |
| 292 | 6820424L24Rik | 6820424L24Rik ‖ RIKEN cDNA 6820424L24 gene |
| 293 | Klf7 | Klf7 ‖ Kruppel-like factor 7 (ubiquitous) |
| 294 | Tm4sf1 | Tm4sf1 ‖ transmembrane 4 superfamily member 1 |
| 295 | Mcpt8 | Mcpt8 ‖ mast cell protease 8 |
| 296 | Has2 | Has2 ‖ hyaluronan syntnase 2 |
| 297 | Slc29a1 | Slc29a1 ‖ solute carrier family 29 (nucleoside transporters), member 1 |
| 298 | Cd44 | Cd44 ‖ CD44 antigen |
| 299 | Tnc | Tnc ‖ tenascin C |
| 300 | Pdgfc | Pdgfc ‖ platelet-derived growth factor, C polypeptide |
| 301 | Tpcn1 | Tpcn1 ‖ two pore channel 1 |
| 302 | Tmeff1 | Tmeff1 ‖ transmembrane protein with EGF-like and two follistatin-like domains 1 |
| 303 | Cdyl | Cdyl ‖ chromodomain protein, Y chromosome-like |
| 304 | Gpr35 | Gpr35 ‖ G protein-coupled receptor 35 |
| 305 | Col6a2 | Col6a2 ‖ procollagen, type VI, alpha 2 |
| 306 | Stab1 | Stab1 ‖ stabilin 1 |
| 307 | Axin2 | Axin2 ‖ axin2 |
| 308 | AI428795 | AI428795 ‖ expressed sequence AI428795 |
| 309 | Igf2 | Igf2 ‖ insulin-like growth factor 2 |
| 310 | Snai1 | Snai1 ‖ snail homolog 1 (*Drosophila*) |
| 311 | Mgl1 | Mgl1 ‖ macrophage galactose N-acetyl-galactosamine specific lectin 1 |
| 312 | Spp1 | Spp1 ‖ secreted phosphoprotein 1 |
| 313 | Pdgfrb | Pdgfrb ‖ platelet derived growth factor receptor, beta polypeptide |
| 314 | Zfhx1a | Zfhx1a ‖ zinc finger homeobox 1a |
| 315 | Pdzrn3 | Pdzrn3 ‖ PDZ domain containing RING finger 3 |
| 316 | Olfml3 | Olfml3 ‖ olfactomedin-like 3 |
| 317 | Cdh11 | Cdh11 ‖ cadherin 11 |
| 318 | 9030425E11Rik | 9030425E11Rik ‖ RIKEN cDNA 9030425E11 gene |
| 319 | Gpr124 | Gpr124 ‖ G protein-coupled receptor 124 |
| 320 | Fstl1 | Fstl1 ‖ follistatin-like 1 |
| 321 | Prrx1 | Prrx1 ‖ paired related homeobox 1 |
| 322 | Timp1 | Timp1 ‖ tissue inhibitor of metalloproteinase 1 |
| 323 | Fn1 | Fn1 ‖ fibronectin 1 |
| 324 | Col1a1 | Col1a1 ‖ procollagen, type I, alpha 1 |
| 325 | Fbn1 | Fbn1 ‖ fibrillin 1 |
| 326 | Col1a2 | Col1a2 ‖ procolianen, type I, alpha 2 |
| 327 | Col5a2 | Col5a2 ‖ procollagen, type V, alpha 2 |
| 328 | Col5a1 | Col5a1 ‖ Procollagen, type V, alpha 1 |
| 329 | Col5a1 | Col5a1 ‖ procollagen, type V, alpha 1 |
| 330 | Col3a1 | Col3a1 ‖ procollagen, type III, alpha 1 |
| 331 | Spon1 | Spon1 ‖ spondin 1, (f-spondin) extracellutar matrix protein |
| 332 | Cxcl14 | Cxcl14 ‖ chemokine (C—X—C motif) ligand 14 |
| 333 | Dkk3 | Dkk3 ‖ dickkopf homolog 3 (*Xenopus laevis*) |
| 334 | Loxl1 | Loxl1 ‖ lysyl oxidase-like 1 |
| 335 | Adamts5 | Adamts5 ‖ a disintegrin-like and metallopeptidase (reprolysin type) with thrombospondin type 1 motif, 5 (aggrecanase-2) |
| 336 | Sox17 | Sox17 ‖ SRY-box containing gene 17 |

TABLE A-continued

| LC Assignment | CLID | NAME |
|---|---|---|
| 337 | Nedd9 | Nedd9 \|\| neural precursor cell expressed, developmentally down-regulated gene 9 |
| 338 | Vegfc | Vegfc \|\| vascular endothelial growth factor C |
| 339 | Slc16a2 | Slc16a2 \|\| solute carrier family 16 (monocarboxylic acid transporters), member 2 |
| 340 | 38968 | 38968 \|\| septin 8 |
| 341 | C2 | C2 \|\| complement component 2 (within H-2S) |
| 342 | Cfh | Cfh \|\| complement component factor h |
| 343 | Cpxm1 | Cpxm1 \|\| carboxypeptidase X 1 (M14 family) |
| 344 | Lum | Lum \|\| lumican |
| 345 | Mmp2 | Mmp2 \|\| matrix metallopeptidase 2 |
| 346 | Saa3 | Saa3 \|\| serum amyloid A 3 |
| 347 | Sfrp1 | Sfrp1 \|\| secreted frizzled-related sequence protein 1 |
| 348 | Masp1 | Masp1 \|\| mannan-binding lectin serine peptidase 1 |
| 349 | Hspg2 | Hspg2 \|\| perlecan (heparan sulfate proteoglycan 2) |
| 350 | Itgbl1 | Itgbl1 \|\| integrin, beta-like 1 |
| 351 | Lrrc35 | Lrrc35 \|\| leucine rich repeat containing 35 |
| 352 | Abca8a | Abca8a \|\| ATP-binding cassette, sub-family A (ABC1), member 8a |
| 353 | Dnajb5 | Dnajb5 \|\| DnaJ (Hsp40) homolog, subfamily B, member 5 |
| 354 | Mgp | Mgp \|\| matrix Gla protein |
| 355 | Serping1 | Serping1 \|\| serine (or cysteine) peptidase inhibitor, clade G, member 1 |
| 356 | Dnm3os | Dnm3os \|\| dynamin 3, opposite strand |
| 357 | Ptgis | Ptgis \|\| prostaglandin I2 (prostacyclin) synthase |
| 358 | Slc43a3 | Slc43a3 \|\| solute carrier family 43, member 3 |
| 359 | Cyp2d22 | Cyp2d22 \|\| cytochrome P450, family 2, subfamily d, polypeptide 22 |
| 360 | Hoxa3 | Hoxa3 \|\| homeo box A3 |
| 361 | Vldlr | Vldlr \|\| very low density lipoprotein receptor |
| 362 | Col6a1 | Col6a1 \|\| procollagen, type VI, alpha 1 |
| 363 | Ulk2 | Ulk2 \|\| Unc-51 like kinase 2 (*C. elegans*) |
| 364 | 2900009I07Rik | 2900009I07Rik \|\| RIKEN cDNA 2900009I07 gene |
| 365 | Cd163 | Cd163 \|\| CD163 antigen |
| 366 | Paqr7 | Paqr7 \|\| progestin and adipoQ receptor family member VII |
| 367 | Ube2r2 | Ube2r2 \|\| ubiquitin-conjugating enzyme E2R 2 |
| 368 | Bcl2l11 | Bcl2l11 \|\| BCL2-like 11 (apoptosis facilitator) |
| 369 | Dpysl3 | Dpysl3 \|\| dihydropyrimidinase-like 3 |
| 370 | Stmn2 | Stmn2 \|\| stathmin-like 2 |
| 371 | Leprel2 | Leprel2 \|\| leprecan-like 2 |
| 372 | Kcnj8 | Kcnj8 \|\| potassium inwardly-rectifying channel, subfamily J, member 8 |
| 373 | Cd1d1 | Cd1d1 \|\| CD1d1 antigen |
| 374 | Mthfr | Mthfr \|\| 5,10-methylenetetrahydrofolate reductase |
| 375 | Aebp1 | Aebp1 \|\| AE binding protein 1 |
| 376 | Prg4 | Prg4 \|\| proteoglycan 4 (megakaryocyte stimulating factor, articular superficial zone protein) |
| 377 | Ccdc80 | Ccdc80 \|\| coiled-coil domain containing 80 |
| 378 | Cd248 | Cd248 \|\| CD248 antigen, endosialin |
| 379 | Htra3 | Htra3 \|\| HtrA serine peptidase 3 |
| 380 | Cygb | Cygb \|\| cytoglobin |
| 381 | Loxl3 | Loxl3 \|\| lysyl oxidase-like 3 |
| 382 | A930004K21Rik | A930004K21Rik \|\| RIKEN cDNA A930004K21 gene |
| 383 | Col11a1 | Col11a1 \|\| procollagen, type XI, alpha 1 |
| 384 | Adpn | Adpn \|\| adiponutrin |
| 385 | Islr | Islr \|\| immunoglobulin superfamily containing leucine-rich repeat |
| 386 | Lepr | Lepr \|\| leptin receptor |
| 387 | Fndc1 | Fndc1 \|\| fibronectin type III domain containing 1 |
| 388 | Thbs2 | Thbs2 \|\| thrombospondin 2 |
| 389 | Ror2 | Ror2 \|\| receptor tyrosine kinase-like orphan receptor 2 |
| 390 | Fgfr1 | Fgfr1 \|\| fibroblast growth factor receptor 1 |
| 391 | Fap | Fap \|\| fibroblast activation protein |
| 392 | Ptger3 | Ptger3 \|\| prostaglandin E receptor 3 (subtype EP3) |
| 393 | Sox11 | Sox11 \|\| SRY-box containing gene 11 |
| 394 | Mmp7 | Mmp7 \|\| matrix metallopeptidase 7 |
| 395 | Penk1 | Penk1 \|\| preproenkephalin 1 |
| 396 | Stc2 | Stc2 \|\| stanniocalcin 2 |
| 397 | Slc2a2 | Slc2a2 \|\| solute carrier family 2 (facilitated glucose transporter), member 2 |
| 398 | Asz1 | Asz1 \|\| ankyrin repeat, SAM and basic leucine zipper domain containing 1 |
| 399 | Ihh | Ihh \|\| Indian hedgehog |
| 400 | Lgr5 | Lgr5 \|\| leucine rich repeat containing G protein coupled receptor 5 |
| 401 | Col10a1 | Col10a1 \|\| procollaven, type X, alpha 1 |
| 402 | D18Ertd232e | D18Ertd232e \|\| DNA segment, Chr 18, ERATO Doi 232, expressed |
| 403 | Ambp | Ambp \|\| alpha 1 microglobulin/bikunin |
| 404 | Pap | Pap \|\| pancreatitis-associated protein |
| 405 | Tnfrsf19 | Tnfrsf19 \|\| tumor necrosis factor receptor superfamily, member 19 |
| 406 | B130052G07Rik | B130052G07Rik \|\| RIKEN cDNA B130052G07 gene |
| 407 | Ncam1 | Ncam1 \|\| neural cell adhesion molecule 1 |
| 408 | Slit3 | Slit3 \|\| slit homolog 3 (*Drosophila*) |
| 409 | Muc3 | Muc3 /// LOC666339 /// LOC677034 \|\| mucin 3, intestinal /// similar to mucin 17 /// similar to mucin 17 |

TABLE A-continued

| LC Assignment | CLID | NAME |
|---|---|---|
| 410 | Col8a1 | Col8a1 \|\| procollagen, type VIII, alpha 1 |
| 411 | Aldh1a2 | Aldh1a2 \|\| aldehyde dehydrogenase family 1, subfamily A2 |
| 412 | Pdlim4 | Pdlim4 \|\| PDZ and LIM domain 4 |
| 413 | AW822216 | AW822216 \|\| expressed sequence AW822216 |
| 414 | Spsb1 | Spsb1 \|\| splA/ryanodine receptor domain and SOCS box containing 1 |
| 415 | F13a1 | F13a1 \|\| coagulation factor XIII, A1 subunit |
| 416 | Fstl3 | Fstl3 \|\| follistatin-like 3 |
| 417 | Wnt2 | Wnt2 \|\| wingless-related MMTV integration site 2 |
| 418 | Cyp26a1 | Cyp26a1 \|\| cytochrome P450, family 26, subfamily a, polypeptide 1 |
| 419 | Scamp5 | Scamp5 \|\| secretory carrier membrane protein 5 |
| 420 | Nppa | Nppa \|\| natriuretic peptide precursor type A |
| 421 | C1qtnf6 | C1qtnf6 \|\| C1q and tumor necrosis factor related protein 6 |
| 422 | Tmem119 | Tmem119 \|\| transmembrane protein 119 |
| 423 | Zmym3 | Zmym3 \|\| zinc finger, MYM-type 3 |
| 424 | Sdc3 | Sdc3 \|\| syndecan 3 |
| 425 | Hoxb2 | Hoxb2 \|\| homeo box B2 |
| 426 | D530037H12Rik | D530037H12Rik \|\| RIKEN cDNA D530037H12 gene |
| 427 | Falz | Falz \|\| fetal Alzheimer antigen |
| 428 | Itsn1 | Itsn1 \|\| intersectin 1 (SH3 domain protein 1A) |
| 429 | Sema6d | Sema6d \|\| sema domain, transmembrane domain (TM), and cytoplastnic domain, (semaphorin) 6D |
| 430 | Atp11c | Atp11c \|\| Atpase, class VI, type 11C |
| 431 | H2-Ea | H2-Ea \|\| histocompatibility 2, class II antigen E alpha |
| 432 | Farp1 | Farp1 \|\| FERM, RhoGEF (Arhgef) and pleckstrin domain protein 1 (chondrocyte-derived) |
| 433 | Smoc2 | Smoc2 \|\| SPARC related modular calcium binding 2 |
| 434 | Sash1 | Sash1 \|\| SAM and SH3 domain containing 1 |
| 435 | Cd47 | Cd47 \|\| CD47 antigen (Rh-related antigen, integrin-associated signal transducer) |
| 436 | Large | Large \|\| like-glycosyltransferase |
| 437 | F2r | F2r \|\| coagulation factor II (thrombin) receptor |
| 438 | Gfpt2 | Gfpt2 \|\| glutamine fructose-6-phosphate transaminase 2 |
| 439 | C1qtnf1 | C1qtnf1 \|\| C1q and tumor necrosis factor related protein 1 |
| 440 | Mcpt2 | Mcpt2 \|\| mast cell protease 2 |
| 441 | Ptprt | Ptprt \|\| protein tyrosine phosphatase, receptor type, T |
| 442 | D1Bwg1363e | D1Bwg1363e \|\| DNA segment, Chr 1, Brigham & Women's Genetics 1363 expressed |
| 443 | Rab2b | Rab2b \|\| RAB2B, member RAS oncogene family |
| 444 | Rffl | Rffl \|\| ring finger and FYVE like domain containing protein |
| 445 | Serpinb1a | Serpinb1a \|\| serine (or cysteine) peptidase inhibitor, clade B, member 1a |
| 446 | Zfyve26 | Zfyve26 \|\| zinc finger, FYVE domain containing 26 |
| 447 | Slamf6 | Slamf6 \|\| SLAM family member 6 |
| 448 | Gdap10 | Gdap10 \|\| ganglioside-induced differentiation-associated-protein 10 |
| 449 | Mafb | Mafb \|\| v-maf musculoaponeurotic fibrosarcoma oncogene family, protein B (avian) |
| 450 | Tcf7l2 | Tcf7l2 \|\| transcription factor 7-like 2, T-cell specific, HMG-box |
| 451 | Itga5 | Itga5 \|\| integrin alpha 5 (fibronectin receptor alpha) |
| 452 | Dock6 | Dock6 /// LOC670024 \|\| dedicator of cytokinesis 6 /// similar to Dedicator of cytokinesis protein 6 |
| 453 | Tesc | Tesc \|\| tescalcin |
| 454 | Tspan5 | Tspan5 \|\| tetraspanin 5 |
| 455 | Dopey2 | Dopey2 \|\| dopey family member 2 |
| 456 | Coil | Coil \|\| coilin |
| 457 | 2810055F11Rik | 2810055F11Rik \|\| RIKEN cDNA 2810055F11 gene |
| 458 | C1s | C1s \|\| complement component 1, s subcomponent |
| 459 | Dmd | Dmd \|\| dystrophin, muscular dystrophy |
| 460 | Dcn | Dcn \|\| decorin |
| 461 | 1110018M03Rik | 1110018M03Rik \|\| RIKEN cDNA 1110018M03 gene |

Inherited mutation in LKB1 results in the Peutz-Jeghers syndrome (PJS), characterized by intestinal hamartomas and an increased frequency of gastrointestinal and breast cancer[36]. Somatic inactivation of LKB1 occurs in human lung adenocarcinoma[9,10,37], but its tumor suppressor role in this tissue is uncertain. Although activation of many kinases (e.g. BRAF, EGFR, etc.) is oncogenic, LKB1 appears unusual in cancer biology in that its kinase activity conveys tumor suppressor activity[38]. LKB1 can phosphorylate multiple cellular substrates and has been implicated in playing important roles in a myriad of cellular metabolic functions including protein synthesis, gluconeogensis, adipogenesis, and steroidogenesis as well as cell polarity. All the substrates of LKB1 that are relevant to tumor suppression are not known, but AMPK, the kinase crucially involved in regulating the mTOR pathway, has been shown to be one definite LKB substrate[39-41].

LKB1 phosphorylates and activates AMP Kinase (AMPK) in settings of high AMP levels (i.e., low energy states). AMPK, in turn, phosphorylates Tuberin, but unlike phosphorylation by Akt, this activates Tuberin's GAP activity leading to inhibition of mTOR activity. However, in LKB1-deficient cells, AMPK cannot be activated, and mTOR remains constitutively active under conditions of energy stress. Thus, mTOR is regulated by growth factor receptor signaling, nutrient availability, and the energy status of the cell. This ensures that a cell normally commits to growth upon appropriate growth stimuli and environmental cues. Transformed and cancer cells, however, bypass one or more of these control mechanisms to grow without restraint. The mTOR pathway is frequently deregulated in many different types of cancer.

In addition, recent studies suggest that LKB1 may play an important role in mediating the cellular responses to DNA damage. ATM, a kinase involved in DNA damage checkpoint and p53-dependent apoptosis, phosphorylates LKB1 on Thr366 after radiation-induced DNA damage[43,44]. This region of LKB1 had been shown to be necessary for its growth suppression function[43,44]. Thus, the loss of LKB1 might render the affected cells more prone to DNA damage and increased genetic alterations. Lastly, reactive lipid species, such as cyclopentenone, often generated in the setting of chronic inflammation and oxidative stress, can inactivate the functional activity of LKB1 through the formation of a covalent adduct at Cys210, an important amino acid in LKB1's activation loop[45].

A human Lkb1 nucleic acid and polypeptide are shown in Table 1 and 2 repectively (SEQ ID NO:1 and SEQ ID NO:2).

TABLE 1

(SEQ ID NO: 1)
Lkb1 Nucleic Acid Sequence

GCGTGTCGGCGCGGAAGGGGAGGCGGCCCGGGGCGCCCGCGAGTGAGG

CGCGGGGCGGCGAAGGGAGCGCGGGTGGCGGCACTTGCTGCCGCGGCCTT

GGATGGGCTGGGCCCCCCTCGCCGCTCCGCCTCCTCCACACGCGCGGCGG

CCGCGGCGAGGGGACGCGCCGCCCGGGGCCCGGCACCTTCGGGAACCCC

CCGGCCCGGAGCCTGCGGCCTGCGCCGCCTCGGCCGCCGGGAGCCCCGTG

GAGCCCCGCCGCCGCGCCGCCCCGCGGACCGGACGCTGAGGGCACTCGG

GGCGGGGCGCGCGCTCGGGCAGACGTTTGCGGGGAGGGGGCGCCTGCCG

GGCCCCGGCGACCACCTTGGGGGTCGCGGGCCGGCTCGGGGGCGCCCAG

TGCGGGCCCTCGCGGGCGCCGGGCAGCGACCAGCCCTGAGCGGAGCTGTT

GGCCGCGGCGGGAGGCCTCCCGGACGCCCCAGCCCCCCGAACGCTCGCC

CGGGCCGGCGGGAGTCGGCGCCCCCCGGGAGGTCCGCTCGGTCGTCCGCG

GCGGAGCGTTTGCTCCTGGGACAGGCGGTGGGACCGGGGCGTCGCCGGAG

ACGCCCCCAGCGAAGTTGGGCTCTCCAGGTGTGGGGGTCCCGGGGGGTAG

CGACGTCGCGGACCCGGCCTGTGGGATGGGCGGCCCGGAGAAGACTGCGC

TCGGCCGTGTTCATACTTGTCCGTGGGCCTGAGCTCCCCGGAGGATGACC

TAGCACTGAAAAGCCCCGGCCGGCCTCCCCAGGGTCCCCGAGGACGAAGT

TGACCCTGACCGGGCCGTCTCCCAGTTCTGAGGCCCGGGTCCCACTGGAA

CTCGCGTCTGAGCCGCCGTCCCGGACCCCCGGTGCCCGCCGGTCCGCAGA

CCCTGCACCGGGCTTGGACTCGCAGCCGGGACTGACGTGTAGAACAATCG

TTTCTGTTGGAAGAAGGGTTTTTCCCTTCCTTTTGGGGTTTTTGTTGCCT

TTTTTTTTTCTTTTTTCTTTGTAAAATTTTGGAGAAGGGAAGTCGGAACA

CAAGGAAGGACCGCTCACCCGCGGACTCAGGGCTGGCGGCGGGACTCCAG

GACCCTGGGTCCAGCATGGAGGTGGTGGACCCGCAGCAGCTGGGCATGTT

CACGGAGGGCGAGCTGATGTCGGTGGGTATGGACACGTTCATCCACCGCA

TCGACTCCACCGAGGTCATCTACCAGCCGCGCCGCAAGCGGGCCAAGCTC

ATCGGCAAGTACCTGATGGGGGACCTGCTGGGGGAAGGCTCTTACGGCAA

TABLE 1-continued (SEQ ID NO: 1)
Lkb1 Nucleic Acid Sequence

GGTGAAGGAGGTGCTGGACTCGGAGACGCTGTGCAGGAGGGCCGTCAAGA

TCCTCAAGAAGAAGAAGTTGCGAAGGATCCCCAACGGGGAGGCCAACGTG

AAGAAGGAAATTCAACTACTGAGGAGGTTACGGCACAAAAATGTCATCCA

GCTGGTGGATGTGTTATACAACGAAGAGAAGCAGAAAATGTATATGGTGA

TGGAGTACTGCGTGTGTGGCATGCAGGAAATGCTGGACAGCGTGCCGGAG

AAGCGTTTCCCAGTGTGCCAGGCCCACGGGTACTTCTGTCAGCTGATTGA

CGGCCTGGAGTACCTGCATAGCCAGGGCATTGTGCACAAGGACATCAAGC

CGGGGAACCTGCTGCTCACCACCGGTGGCACCCTCAAAATCTCCGACCTG

GGCGTGGCCGAGGCACTGCACCCGTTCGCGGCGGACGACACCTGCCGGAC

CAGCCAGGGCTCCCCGGCTTTCCAGCCGCCCGAGATTGCCAACGGCCTGG

ACACCTTCTCCGGCTTCAAGGTGGACATCTGGTCGGCTGGGGTCACCCTC

TACAACATCACCACGGGTCTGTACCCCTTCGAAGGGGACAACATCTACAA

GTTGTTTGAGAACATCGGGAAGGGGAGCTACGCCATCCCGGGCGACTGTG

GCCCCCCGCTCTCTGACCTGCTGAAAGGGATGCTTGAGTACGAACCGGCC

AAGAGGTTCTCCATCCGGCAGATCCGGCAGCACAGCTGGTTCCGGAAGAA

ACATCCTCCGGCTGAAGCACCAGTGCCCATCCCACCGAGCCCAGACACCA

AGGACCGGTGGCGCAGCATGACTGTGGTGCCGTACTTGGAGGACCTGCAC

GGCGCGGACGAGGACGAGGACCTCTTCGACATCGAGGATGACATCATCTA

CACTCAGGACTTCACGGTGCCCGGACAGGTCCCAGAAGAGGAGGCCAGTC

ACAATGGACAGCGCCGGGGCCTCCCCAAGGCCGTGTGTATGAACGGCACA

GAGGCGGCGCAGCTGAGCACCAAATCCAGGGCGGAGGGCCGGGCCCCCAA

CCCTGCCCGCAAGGCCTGCTCCGCCAGCAGCAAGATCCGCCGGCTGTCGG

CCTGCAAGCAGCAGTGAGGCTGGCCGCCTGCAGCCCGTGTCCAGGAGCCC

CGCCAGGTGCCCGCGCCAGGCCCTCAGTCTTCCTGCCGGTTCCGCCCGCC

CTCCCGGAGAGGTGGCCGCCATGCTTCTGTGCCGACCACGCCCCAGGACC

TCCGGAGCGCCCTGCAGGGCCGGGCAGGGGGACAGCAGGGACCGGGCGCA

GCCCTCCCCCCTCGGCCGCCCGGCAGTGCACGCGGCTTGTTGACTTCGCA

GCCCCGGGCGGAGCCTTCCCGGGCGGGCGTGGGAGGAGGGAGGCGGCCTC

CATGCACTTTATGTGGAGACTACTGGCCCCGCCCGTGGCCTCGTGCTGCG

CAGGGCGCCCAGCGCCGTCCGGCGGCCCCGCCGCAGACCAGCTGGCGGGT

GTGGAGACCAGGCTCCTGACCCCGCCATGCATGCAGCGCCACCTGGAAGC

CGCGCGGCCGCTTTGGTTTTTTGTTTGGTTGGTTCCATTTTCTTTTTTC

TTTTTTTTTTAAGAAAAAATAAAAGGTGGATTTGAGCTGTGGCTGTGAG

GGGTGTTTGGGAGCTGCTGGGTGGCAGGGGGGCTGTGGGGTCGGGCTCAC

GTCGCGGCCGCCTTTGCGCTCTGGGTCACCCTGCTTTGGGGGCCCGGCC

GGAGGGCAGGACCCTCACCTCTCCCCCAAGGCCACTGCGCTCTTGGGACC

CCAGAGAAACCCGGAGCAAGCAGGAGTGTGCGGTCAATATTTATATCAT

CCAGAAAAGAAAAACACGAGAAACGCCATCGCGGGATGGTGCAGACGCGG

TABLE 1-continued (SEQ ID NO: 1)
Lkb1 Nucleic Acid Sequence

CGGGGACTCGGAGGGTGCCGTGCGGGCGAGGCCGCCCAAATTTGGCAATA

AATAAAGCTTGGGAAGCTTGGACCTGAAAAAAAAAA

TABLE 2

(SEQ ID NO: 2)
Lkb1 Polypeptide Sequence

MEVVDPQQLGMFTEGELMSVGMDTFIHRIDSTEVIYQPRRKRAKLIGKYL

MGDLLGEGSYGKVKEVLDSETLCRRAVKILKKKKLRRIPNGEANVKKEIQ

LLRRLRHKNVIQLVDVLYNEEKQKMYMVMEYCVCGMQEMLDSVPEKRFPV

CQAHGYFCQLIDGLEYLHSQGIVHKDIKPGNLLLTTGGTLKISDLGVAEA

LHPFAADDTCRTSQGSPAFQPPEIANGLDTFSGFKVDIWSAGVTLYNITT

GLYPFEGDNIYKLFENIGKGSYAIPGDCGPPLSDLLKGMLEYEPAKRFSI

RQIRQHSWFRKKHPPAEAPVPIPPSPDTKDRWRSMTVVPYLEDLHGADED

EDLFDIEDDIIYTQDFTVPGQVPEEEASHNGQRRGLPKAVCMNGTEAAQL

STKSRAEGRAPNPARKACSASSKIRRLSACKQQ

Diagnostic and Prognostic Methods

The aggressiveness of lung cancers is determined by examining the presence (e.g, expression) or absence of a Lkb1 nucleic acid, polypeptide or activity in a test sample (i.e., a patient derived sample). Preferably, the test sample is a tumor biopsy. A change in the level of the Lkb1 nucleic acid, polypeptide or activity compared to a control sample is indicative of the aggressiveness of the lung cancer in the subject. The absence of the Lkb1 nucleic acid or polypeptide or a decrease in the activity of Lkb1 in the test sample indicates that the cancer is aggressive, thus a less favorable prognosis for the patient. An aggressive tumor is metastatic, thus the absence of the Lkb1 nucleic acid or polypeptide or a decrease in the activity of Lkb1 in the test sample indicates that the tumor is metastatic. In contrast, the presence of the Lkb1 nucleic acid or polypeptide or activity of Lkb1 indicates that the lung cancer is not aggressive, thus a more favorable prognosis for the patient.

Additionally, the presence or absence of a mutation the Lkb1 nucleic acid is indicative of the aggressivness of the lung cancer in the subject. For example, the presence of a mutation in the the Lkb1 nucleic acid in the test sample indicates that the cancer is aggressive, thus a less favorable prognosis for the patient. Whereas the absence a mutation in the Lkb1 nucleic acid indicates that the lung cancer is not aggressive, thus a more favorable prognosis the the patient.

By aggressivness it is meant that that the tumor is quick growing and spreading (i.e, metastasizing.

The amount of the Lkb1 nucleic acid, polypeptide or activity is determined in the test sample and compared to the expression of the normal control level. By normal control level is meant the expression level of a Lkb1 nucleic acid, polypeptide or activity typically found in a subject not suffering from lung cancer.

The alteration in the amount of the Lkb1 nucleic acid, polypeptide or activity is statistically significant. By statistically significant is meant that the alteration is greater than what might be expected to happen by change alone. Statistical significance is determined by method known in the art. For example statistical significance is determined by p-value. The p-values is a measure of probability that a difference between groups during an experiment happened by chance. ($P(z \geq z_{observed})$). For example, a p-value of 0.01 means that there is a 1 in 100 chance the result occurred by chance. The lower the p-value, the more likely it is that the difference between groups was caused by treatment. An alteration is statistically significant if the p-value is at least 0.05. Preferably, the p-value is 0.04, 0.03, 0.02, 0.01, 0.005, 0.001 or less.

The "diagnostic accuracy" of a test, assay, or method concerns the ability of the test, assay, or method to distinguish between patients having aggressive lung cancer and non-aggressive lung cancer is based on whether the patients have a "clinically significant presence or absence" of a Lkb1 nucleic acid, polypeptide or activity. By "clinically significant presence" is meant that the presence of the Lkb1 nucleic acid, polypeptide or activity in the patient (typically in a sample from the patient) is higher or lower than the predetermined cut-off point (or threshold value) for Lkb1 nucleic acid, polypeptide or activity and therefore indicates that the patient has cancer for which the sufficiently high presence of that protein is a marker.

The terms "high degree of diagnostic accuracy" and "very high degree of diagnostic accuracy" refer to the test or assay for that Lkb1 nucleic acid, polypeptide or activity with the predetermined cut-off point correctly (accurately) indicating the presence or absence of the cancer. A perfect test would have perfect accuracy. Thus, for individuals who have aggressive lung cancer, the test would indicate only positive test results and would riot report any of those individuals as being "negative" (there would be no "false negatives"). In other words, the "sensitivity" of the test (the true positive rate) would be 100%. On the other hand, for individuals who did not have aggressive lung cancer, the test would indicate only negative test results and would not report any of those individuals as being "positive" (there would be no "false positives"). In other words, the "specificity" (the true negative rate) would be 100%. See, e.g., O'Marcaigh A S, Jacobson R M, "Estimating The Predictive Value Of A Diagnostic Test, How To Prevent Misleading Or Confusing Results," Clin. Ped. 1993, 32(8): 485-491, which discusses specificity, sensitivity, and positive and negative predictive values of a test, e.g., a clinical diagnostic test.

Changing the cut point or threshold value of a test (or assay) usually changes the sensitivity and specificity but in a qualitatively inverse relationship. For example, if the cut point is lowered, more individuals in the population tested will typically have test results over the cut point or threshold value. Because individuals who have test results above the cut point are reported as having the disease, condition, or syndrome for which the test is being run, lowering the cut point will cause more individuals to be reported as having positive results (i.e., that they have cancer). Thus, a higher proportion of those who have cancer will be indicated by the test to have it. Accordingly, the sensitivity (true positive rate) of the test will be increased. However, at the same time, there will be more false positives because more people who do not have the disease, condition, or syndrome (i.e., people who are truly "negative") will be indicated by the test to have Lkb1 nucleic acid, polypeptide or activity values above the cut point and therefore to be reported as positive rather than being correctly indicated by the test to be negative. Accordingly, the specificity (true negative rate) of the test will be decreased. Similarly, raising the cut point will tend to decrease the sensitivity and increase the specificity.

Therefore, in assessing the accuracy and usefulness of a proposed medical test, assay, or method for assessing a patient's condition, one should always take both sensitivity and specificity into account and be mindful of what the cut point is at which the sensitivity and specificity are being reported because sensitivity and specificity may vary significantly over the range of cut points.

There is, however, an indicator that allows representation of the sensitivity and specificity of a test, assay, or method over the entire range of cut points with just a single value. That indicator is derived from a Receiver Operating Characteristics ("ROC") curve for the test, assay, or method in question, See, e.g., Shultz, "Clinical Interpretation Of Laboratory Procedures," chapter 14 in Teitz, Fundamentals of Clinical Chemistry, Burtis and Ashwood (eds.), 4th edition 1996, W.B. Saunders Company, pages 192-199; and Zweig et al., "ROC Curve Analysis: An Example Showing The Relationships Among Serum Lipid And Apolipoprotein Concentrations In Identifying Patients With Coronary Artery Disease," Clin. Chem., 1992, 38(8): 1425-1428.

An ROC curve is an x-y plot of sensitivity on the y-axis, on a scale of zero to one (i.e., 100%), against a value equal to one minus specificity on the x-axis, on a scale of zero to one (i.e., 100%). In other words, it is a plot of the true positive rate against the false positive rate for that test, assay, or method. To construct the ROC curve for the test, assay, or method in question, patients are assessed using a perfectly accurate or "gold standard" method that is independent of the test, assay, or method in question to determine whether the patients are truly positive or negative for the disease, condition, or syndrome (for example, coronary angiography is a gold standard test for the presence of coronary atherosclerosis). The patients are also tested using the test, assay, or method in question, and for varying cut points, the patients are reported as being positive or negative according to the test, assay, or method. The sensitivity (true positive rate) and the value equal to one minus the specificity (which value equals the false positive rate) are determined for each cut point, and each pair of x-y values is plotted as a single point on the x-y diagram. The "curve" connecting those points is the ROC curve.

The area under the curve ("AUC") is the indicator that allows representation of the sensitivity and specificity of a test, assay, or method over the entire range of cut points with just a single value. The maximum AUC is one (a perfect test) and the minimum area is one half. The closer the AUC is to one, the better is the accuracy of the test.

By a "high degree of diagnostic accuracy" is meant a test or assay (such as the test of the invention for determining the clinically significant presence of Lkb1 nucleic acid, polypeptide or activity, in which the AUC (area under the ROC curve for the test or assay) is at least 0.70, desirably at least 0.75, more desirably at least 0.80, preferably at least 0.85, more preferably at least 0.90, and most preferably at least 0.95.

By a "very high degree of diagnostic accuracy" is meant a test or assay in which the AUC (area under the ROC curve for the test or assay) is at least 0.875, desirably at least 0.90, more desirably at least 0.925, preferably at least 0.95, more preferably at least 0.975, and most preferably at least 0.98.

Optionally, the subject is tested for carrying other indicators of susceptibility of developing cancer. For example, the presence or absence of a mutation in K-ras, EGFR or BRAF is determined in the test sample.

The Lkb1 nucleic acid, polypeptide or activity are detected in any suitable manner, but is typically detected by contacting a sample from the patient with an antibody which binds the Lkb1 nucleic acid, polypeptide add then detecting the presence or absence of a reaction product. The antibody may be monoclonal, polyclonal, chimeric, or a fragment of the foregoing, as discussed in detail above, and the step of detecting the reaction product may be carried out with any suitable immunoassay. The sample from the subject is typically a tumor biopsy as described above.

Lung cancer is also diagnosed by examining the expression of one or more LC nucleic acid or polypeptide sequences from a test population of cells, (i.e., a patient derived tissue sample) that contain or suspected to contain a non-small cell lung cancer cell. Preferably, the test cell population comprises a lung cell, e.g., a cell obtained from the lung. Gene expression is also measured from blood or other bodily fluids such as sputum.

Expression of one or more of a lung cancer-associated gene, e.g., LC 1 -461 is determined in the test cell and compared to the expression of the normal control level. By normal control level is meant the expression profile of the lung cancer-associated genes typically found in a population not suffering from lung cancer. An increase of the level of expression in the patient derived tissue sample of the lung cancer associated genes indicates that the subject is suffering from or is at risk of developing lung cancer.

Also provided is a method of assessing the prognosis of a subject with lung cancer by comparing the expression of one or more LC sequences in a test cell population to the expression of the sequences in a reference cell population derived from patients over a spectrum of disease stages. By comparing gene expression of one or more LC sequences in the test cell population and the reference cell population(s), or by comparing the pattern of gene expression over time in test cell populations derived from the subject, the prognosis of the subject can be assessed. For example, an increase in expression of one or more of the sequences LC 1-461 compared to a normal control indicates less favorable prognosis.

The differentially LC sequences identified herein also allow for the course of treatment of lung cancer to be monitored. In this method, a test cell population is provided from a subject undergoing treatment for lung cancer. If desired, test cell populations are obtained from the subject at various time points before, during, or after treatment. Expression of one or more of the LC sequences, in the cell population is then determined and compared to a reference cell population which includes cells whose lung cancer state is known. The reference cells have not been exposed to the treatment.

If the reference cell population contains no lung cancer cells, a similarity in expression between LC sequences in the test cell population and the reference cell population indicates that the treatment is efficacious. However, a difference in expression between LC sequences in the test population and this reference cell population indicates the a less favorable clinical outcome or prognosis.

By "efficacious" is meant that the treatment leads to a reduction in expression of a pathologically upregulated gene, increase in expression of a pathologically downregulated gene or a decrease in size, prevalence, or metastatic potential of lung cancer in a subject. When treatment is applied prophylactically, "efficacious" means that the treatment retards or prevents lung cancer from forming. Assessment of lung cancer is made using standard clinical protocols.

Efficaciousness is determined in association with any known method for diagnosing or treating non-small cell lung cancer. Lung cancer is diagnosed for example, by identifying symptomatic anomalies, e.g., chronic cough, hoarseness, coughing up blood, weight loss, loss of appetite, shortness of breath, wheezing, repeated bouts of bronchitis or pneumonia, and chest pain or histopathologically.

Expression of Lkb1 also allows the identification of patients who will be responsive to systemic therapy, e.g. m-TOR inhibitors. In this method, a tumor sample is provided from a subject and Lkb1 expression is determined. Identification of inactivation of the Lkb1 gene indicate that the therapy will be efficacious. In contrast a the patient will likely not be responsive to systemic treatment with an M-TOR inhibitor if the Lkb1 gene is active. By inactivation is meant a decrease in Lkb1 expression or activity. For example the Lkb1 gene is inactivated due to a mutation.

The subject is preferably a mammal. The mammal is, e.g., a human, non-human primate, mouse, rat, dog, cat, horse, or cow. Subjects are typically human females or human males.

The subject has been previously diagnosed as carrying a cancer, and possibly has already undergone treatment for the cancer. Alternatively, the subject has not been previously diagnosis as carrying a cancer. The present invention is useful with all patients at risk for a cancer. Although each type of cancer has their own set of risk factors, the risk of developing cancer increases as with aged, gender, race and personal and family medical history. Other risk factors are largely related to lifestyle choices, while certain infections, occupational exposures and some environmental factors can also be related to developing cancer. Lung cancer risk factors include personal and family history of lung cancer, smoking, exposure to asbestos, radon or other carcinogens, air pollution, Vitamin A deficiency, or reoccurring inflammation.

Diagnosis of cancer is typically made through the identification of a mass on an examination, though it may also be through other means such as a radiological diagnosis, or ultrasound. Treatment is typically through cytoreductive surgery. In addition, many patients will require radiation therapy.

Expression of the Lkb1, a LC nuclic acid or polypeptide or other cancer biomarkers (e.g., K-ras, EGFR or BRAf) is determined at the protein or nucleic acid level using any method known in the art. For example, Northern hybridization analysis using probes which specifically recognize one or more of these sequences can be used to determine gene expression. Alternatively, expression is measured using reverse-transcription-based PCR assays, e.g., using primers specific for the differentially expressed sequence of genes. Expression is also determined at the protein level, i.e., by measuring the levels of peptides encoded by the gene products described herein, or activities thereof. Such methods are well known in the art and include, e.g., immunoassays based on antibodies to proteins encoded by the genes. Any biological material can be used for the detection/ quantification of the protein or it's activity. Alternatively, a suitable method can be selected to determine the activity of proteins encoded by the marker genes according to the activity of each protein analyzed.

Immunoassays carried out in accordance with the present invention may be homogeneous assays or heterogeneous assays. In a homogeneous assay the immunological reaction usually involves the specific antibody (e.g., fibrinogen αC domain peptide or hemoglobin polypeptide), a labeled analyte, and the sample of interest. The signal arising from the label is modified, directly or indirectly, upon the binding of the antibody to the labeled analyte. Both the immunological reaction and detection of the extent thereof are carried out in a homogeneous solution immunochemical labels which may be employed include free radicals, radioisotopes, fluorescent dyes, enzymes, bacteriophages, or coenzymes.

In a heterogeneous assay approach, the reagents are usually the sample, the antibody, and means for producing a detectable signal. Samples as described above may be used. The antibody is generally immobilized on a support, such as a bead, plate or slide, and contacted with the specimen suspected of containing the antigen in a liquid phase. The support is then separated from the liquid phase and either the support phase or the liquid phase is examined for a detectable signal employing means for producing such signal. The signal is related to the presence of the analyte in the sample. Means for producing a detectable signal include the use of radioactive labels, fluorescent labels, or enzyme labels. For example, if the antigen to be detected contains a second binding site, an antibody which binds to that site can be conjugated to a detectable group and added to the liquid phase reaction solution before the separation step. The presence of the detectable group on the solid support indicates the presence of the antigen in the test sample. Examples of suitable immunoassays are radioimmunoassays, immunofluorescence methods, or enzyme-linked immunoassays.

Those skilled in the art will be familiar with numerous specific immunoassay formats and variations thereof, which may be useful for carrying out the method disclosed herein. See generally E. Maggio, Enzyme-Immunoassay, (1980) (CRC Press, Inc., Boca Raton, Fla.); see also U.S. Pat. No. 4,727,022 to Skold et al. titled "Methods for Modulating Ligand-Receptor Interactions and their Application," U.S. Pat. No. 4,659,678 to Forrest et al. titled "Immunoassay of Antigens," U.S. Pat. No. 4,376,110 to David et al., titled "Immunometric Assays Using Monoclonal Antibodies," U.S. Pat. No. 4,275,149 to Litman et al., titled "Macromolecular Environment Control in Specific Receptor Assays," U.S. Pat. No. 4,233,402 to Maggio et al., titled "Reagents and Method Employing Channeling," and U.S. Pat. No. 4,230,767 to Boguslaski et al., titled "Heterogeneous Specific Binding Assay Employing a Coenzyme as Label."

Antibodies are conjugated to a solid support suitable for a diagnostic assay (e.g., beads, plates, slides or wells formed from materials such as latex or polystyrene) in accordance with known techniques, such as precipitation. An antibody or antibody fragment that binds to CA-125 or CEA may optionally be conjugated to the same support, as discussed above. Antibodies as described herein may likewise be conjugated to detectable groups such as radiolabels (e.g., 35 S, 125 I, 131 I), enzyme labels (e.g., horseradish peroxidase, alkaline phosphatase), and fluorescent labels (e.g., fluorescein) in accordance with known techniques.

Screening Methods

An agent that inhibits the expression or activity of a lung cancer-associated gene is identified by contacting a test cell population expressing a lung cancer associated upregulated gene with a test agent and determining the expression level of the lung cancer associated gene. A decrease in expression compared to the normal control level indicates the agent is an inhibitor of a lung cancer associated upregulated gene and useful to inhibit non-small cell lung cancer.

The differentially expressed sequences disclosed herein can also be used to identify candidate therapeutic agents for treating lung cancer. The method is based on screening a candidate therapeutic agent to determine if it converts an expression profile of LC 1-461 sequences characteristic of a lung cancer state to a pattern indicative of a non lung cancer state.

In the method, a cell is exposed to a test agent or a combination of test agents (sequentially or consequentially) and the expression of one or more LC 1-461 sequences in the cell is measured. The expression profile of the IX sequences in the test population is compared to expression level of the LC sequences in a reference cell population that is not exposed to the test agent.

Alternatively, the screening of the present invention may comprise the steps described below. A protein required for the screening cart be obtained as a recombinant protein by using the nucleotide sequence of the marker gene. Based on the information on the marker gene, one skilled in the art can select the biological activity of a protein as an index of screening and a measurement method for the activity.

(1) the step of contacting a candidate agent with the protein encoded by a marker gene; and (2) the step of selecting a candidate agent that alters the activity of the protein as compared with that in a control.

Alternatively, the screening of the present invention may comprise the steps described below. A reporter construct required for the screening can be prepared by using the transcriptional regulatory region of a marker gene. When the transcriptional regulatory region of a marker gene has been known to those skilled in the art, a reporter construct can be prepared by using the previous sequence information. When the transcriptional regulatory region of a marker gene remains unidentified, a nucleotide segment containing the transcriptional regulatory region can be isolated from a genome library based on the nucleotide sequence information of the marker gene.

(1) the step of preparing a reporter construct that ensures the expression of the reporter gene under control of the transcriptional regulatory region of the marker gene;

(2) the step of contacting a candidate agent with host cells containing and capable of expressing the above-mentioned reporter construct; and (3) the step of measuring the expression level of the reporter gene, and selecting a candidate agent that has an activity of altering the expression level when compared with that in a control.

There is no limitation on the type of candidate agent in the screening of the present invention. The candidates of the present invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam (1997) Anticancer Drug Des. 12:145).

Examples of methods for the synthesis of molecular libraries can be found in the art, for example in: DeWitt et al. (1993) Proc. Natl. Acad. Sci. USA 90:6909; Erb et at. (1994) Proc. Natl. Acad. Sci. USA 91:11472; Zuckermann et al. (1994). J. Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and Gallop et al. (1994) J. Med. Chem. 37:1233.

Libraries of compounds may be presented in solution (e.g., Houghten (1992) Bio Techniques 13:412), or on beads (Lam (1991) Nature 354:82), chips (Fodor (1993) Nature 364:555), bacteria (U.S. Pat. No. 5,223,409), spores (U.S. Pat. Nos. 5,571,698; 5,403,484; and 5,223,409), plasmids (Cull et al. (1992) Proc. Natl. Acad. Sci. USA 89:1865) or phage (Scott and Smith (1990) Science 249:386; Devlin. (1990) Science 249:404; Cwirla et al. (1990) Proc. Natl. Acad. Sci. USA 87:6378; and Felici (1991) J. Mol. Biol. 222:301). (United States Patent Application 20020103360)

An agent effective i in suppressing expression of overexpressed genes is deemed to lead to a clinical benefit such compounds are further tested for the ability to prevent cancer cell growth.

Differences in the genetic makeup of individuals can result in differences in their relative abilities to metabolize various drugs. An agent that is metabolized in a subject to act as an anti-cell lung cancer agent can manifest itself by inducing a change in gene expression pattern in the subject's cells from that characteristic of a cancerous state to a gene expression pattern characteristic of a non-cancerous state. Accordingly, the differentially expressed LC sequences disclosed herein allow for a putative therapeutic or prophylactic anti-lung cancer agent to be tested in a test cell population from a selected subject in order to determine if the agent is a suitable ant lung cancer agent in the subject.

To identify an anti-lung cancer agent, that is appropriate for a specific subject, a test cell population from the subject is exposed to a therapeutic agent, and the expression of one or more of LC 1-461 sequences is determined. For example a test cell population is incubated in the presence of a candidate agent and the pattern of gene expression of the test sample is measured and compared to one or more reference profiles, e.g., a non-lung cancer reference expression profile or an lung cancer reference expression profile.

A decrease in expression of one or more of the sequences LC 1-461 oin a test cell population relative to a reference cell population containing non-lung cancer is indicative that the agent is therapeutic.

The test cell population is any cell expressing the lung cancer-associated genes. For example, the test cell population contains an epithelial cell. For example, the test cell is immortalized cell line derived from a lung cancer cell.

The test agent can be any compound or composition.

Kits

The invention also includes an Lkb1 or LC-detection reagent, e.g., a nucleic acid that specifically binds to or identifies one or more NSC nucleic acids such as oligonucleotide sequences, which are complementary to a portion of a Lkb1 or LC nucleic acid or antibodies which bind to proteins encoded by a Lkb1 or LC nucleic acid. The reagents are packaged together in the form of a kit. The reagents are packaged in separate containers, e.g., a nucleic acid or antibody (either bound to a solid matrix or packaged separately with reagents for binding them to the matrix), a control reagent (positive and/or negative), and/or a detectable label. Instructions (e.g., written, tape, VCR, CD-ROM, etc.) for carrying out the assay are included in the kit. The assay format of the kit is a Northern hybridization or a sandwich ELISA known in the art.

For example, Lkb1 or LC detection reagent, is immobilized on a solid matrix such as a porous strip to form at least one Lkb1 or LC detection site. The measurement or detection region of the porous strip may include a plurality of sites containing a nucleic acid. A test strip may also contain sites for negative and/or positive controls. Alternatively, control sites are located on a separate strip from the test strip. Optionally, the different detection sites may contain different amounts of immobilized nucleic acids, i.e., a higher amount in the first detection site and lesser amounts in subsequent sites. Upon the addition of test sample, the number of sites displaying a detectable signal provides a quantitative indication of the amount of Lkb1 or LC present in the sample.

The detection sites may be configured in any suitably detectable shape and are typically in the shape of a bar or dot spanning the width of a teststrip.

Alternatively, the kit contains a nucleic acid substrate array comprising one or more nucleic acid sequences. The nucleic acids on the array specifically identify one or more nucleic acid sequences represented by LKB1 ore LC 1-461. The expression of 2, 3, 4, 5, 6, 7, 8, 9, 10, 15, 20, 25, 40 or 50 or more of the sequences represented by LC 1-461 are identified by virtue if the level of binding to an array test strip or chin. The substrate array can be on, e.g., a solid substrate, e.g., a "chip" as described in U.S. Pat. No. 5,744,305.

Arrays and Pluralities

The invention also includes a nucleic acid substrate array comprising one or more nucleic acid sequences. The nucleic acids on the array specifically corresponds to one or more nucleic acid sequences represented by LC 1-461. The level expression of 2, 3, 4, 5, 6, 7, 8, 9, 10, 15, 20, 25, 40 or 50 or more of the sequences represented by LC 1-461 are identified by detecting nucleic acid binding to the array.

The invention also includes an isolated plurality (i.e., a mixture if two or more nucleic acids) of nucleic acid sequences. The nucleic acid sequence are in a liquid phase or a solid phase, e.g., immobilized on a solid support such as a nitrocellulose membrane. The plurality includes one or more of the nucleic acid sequences represented by LC 1-461. In various embodiments, the plurality includes 2, 3, 4, 5, 6, 7, 8, 9, 10, 15, 20, 25, 40 or 50 or more of the sequences represented by LC 1-461

Chips

The DNA chip is a device that is convenient to compare expression levels of a number of genes at the same time. DNA chip-based expression profiling can be carried out, for example, by the method as disclosed in "Microarray Biochip Technology" (Mark Schena, Eaton Publishing, 2000), etc.

A DNA chip comprises immobilized high-density probes to detect a number of genes. Thus, expression levels of many genes can be estimated at the same time by a single-round analysis. Namely, the expression profile of a specimen can be determined with a DNA chip. The DNA chip-based method of the present invention comprises the following steps of:

(1) synthesizing cRNAs or cDNAs corresponding to the marker genes;

(2) hybridizing the cRNAs or cDNAs with probes for marker genes; and (3) detecting the cRNA or cDNA hybridizing with the probes and quantifying the amount of mRNA thereof.

The cRNA refers to RNA transcribed from a template cDNA with RNA polymerase. A cRNA transcription kit for DNA chip-based expression profiling is commercially available. With such a kit, cRNA can be synthesized from T7 promoter-attached cDNA as a template by using T7 RNA polymerase. On the other hand, by PCR using random primer, cDNA can be amplified using as a template a cDNA synthesized from mRNA.

On the other hand, the DNA chip comprises probes, which have been spotted thereon, to detect the marker genes of the present invention. There is no limitation on the number of marker genes spotted on the DNA chip. For example, it is allowed to select 5% or more, preferably 20% or more, more preferably 50% or more, still more preferably 70% or more of the marker genes of the present invention. Any other genes as well as the marker genes can be spotted on the DNA chip. For example, a probe for a gene whose expression level is hardly altered may be spotted on the DNA chip. Such a gene can be used to normalize assay results when assay results are intended to be compared between multiple chips or between different assays.

A probe is designed for each marker gene selected, and spotted on a DNA chip. Such a probe may be, for example, an oligonucleotide comprising 5-50 nucleotide residues. A method for synthesizing such oligonucleotides on a DNA chip is known to those skilled in the art. Longer DNAs can be synthesized by PCR or chemically. A method for spotting long DNA, which is synthesized by PCR or the like, onto a glass slide is also known to those skilled in the art. A DNA chip that is obtained by the method as described above can be used for diagnosing a disease X according to the present invention.

The prepared DNA chip is contacted with cRNA, followed by the detection of hybridization between the probe and cRNA. The cRNA can be previously labeled with a fluorescent dye. A fluorescent dye such as Cy3 (red) and Cy5 (blue) can be used to label a cRNA. cRNAs from a subject and a control are labeled with different fluorescent dyes, respectively. The difference in the expression level between the two can be estimated based on a difference in the signal intensity. The signal of fluorescent dye on the DNA chip can be detected by a scanner and analyzed by using a special program. For example, the Suite from Affymetrix is a software package for DNA chip analysis.

Transgenic Animals

In another aspect, the present invention includes transgenic animals containing a heterologous (or exogenous) gene construct. Specifically, the invention provided a transgenic animal whose genome contains a mutant K-ras oncogene and at least one Lkb1 null allele. Optionally, animal is homozygous null for Lkb1. The animal exhibits accelerated development of a lung tumor. Preferably the K-ras mutation is a G12 D mutation.

The preparation of a transgenic mammal requires introducing a nucleic acid construct that will be used to express a nucleic acid encoding a light-generating fusion protein into an undifferentiated cell type, e.g., an embryonic stern (ES) cell. The ES cell is then injected into a mammalian embryo, where it will integrate into the developing embryo. The embryo is then implanted into a foster mother for the duration of gestation.

Embryonic stem cells are typically selected for their ability to integrate into and become part of the germ line of a developing embryo so as to create germ line transmission of the heterologous gene construct. Thus, any ES cell line that has this capability is suitable for use herein. One mouse strain that is typically used for production of ES cells is the 129J strain. A preferred ES cell line is murine cell line D3 (American Type Culture Collection catalog no. CRL 1934). The cells are cultured and prepared for DNA insertion using methods well known in the art, such as those set forth by Robertson (Robertson, In: *Teratocarcinomas and Embryonic Stem Cells: A Practical Approach*, E. J. Robertson, ed., IRL Press, Washington, D.C., 1987.). Insertion of the nucleic acid construct into the ES cells can be accomplished using a variety of methods well known in the art including for example, electroporation, microinjection, and calcium phosphate treatment.

The term "transgene" is used herein to describe genetic material that has been or is about to be artificially inserted into the genome of a mammalian cell, particularly a mammalian cell of a living animal. The transgene is used to transform a cell, meaning that a permanent or transient genetic change, preferably a permanent genetic change, is induced in a cell following incorporation of an heterologous nucleic acid, such as DNA. A permanent genetic change is generally achieved by introduction of the DNA into the genome of the cell. Vectors for stable integration include plasmids, retroviruses and other animal viruses, YACs, and the like. Of interest are transgenic mammals, cows, pigs, goats, horses, etc., and particularly rodents, e.g., rats, mice, etc. Preferably, the transgenic animals are mice.

Transgenic animals comprise an heterologous nucleic acid sequence present as an extrachromosomal element or stably integrated in all or a portion of its cells, especially in germ cells. Unless otherwise indicated, it will be assumed that a transgenic animal comprises stable changes to the germline sequence. During the initial construction of the animal, "chimeras" or "chimeric animals" are generated, in which only a subset of cells have the altered genome. Chimeras are primarily used for breeding purposes in order to generate the desired transgenic animal. Animals having a heterozygous alteration are generated by breeding of chimeras. Male and female heterozygotes are typically bred to generate homozygous animals.

The heterologous gene is usually either from a different species than the animal host, or is otherwise altered in its coding or non-coding sequence. The introduced gene may be a wild-type gene, naturally occurring polymorphism, or a genetically manipulated sequence, for example having deletions, substitutions or insertions in the coding or non-coding regions. Where the introduced gene is a coding sequence, it is usually operably linked to a promoter, which may be constitutive or inducible, and other regulatory sequences required for expression in the host animal. By "operably linked" is meant that a DNA sequence and a regulatory sequence(s) are connected in such a way as to permit gene expression when the appropriate molecules, e.g., transcriptional activator proteins, are bound to the regulatory sequence(s). The transgenic animals of the invention can comprise other genetic alterations in addition to the presence of the heterologous gene. For example, the host's genome may be altered to affect the function of endogenous genes, contain marker genes, or other genetic alterations such as are described in the Examples.

Although not necessary to the operability of the invention, the transgenic animals described herein may comprise alterations to endogenous genes in addition to (the genetic alterations described above. For example, the host animals may be either "knockouts" and/or "knockins" for a target gene(s) as is consistent with the goals of the invention (e.g., the host animal's endogenous HIF1α may be "knocked out" and/or the endogenous bioluminescent fusion protein "knocked in". Knockouts have a partial or complete loss of function in one or both alleles of an endogenous gene of interest. Knockins have an introduced transgene with altered genetic sequence and/or function from the endogenous gene. The two may be combined, for example, such that the naturally occurring gene is disabled, and an altered form introduced.

In a knockout, preferably the target gene expression is undetectable or insignificant. For example, a knock-out of an gene means that function of the gene has been substantially decreased so that expression is not detectable or only present at insignificant levels. This may be achieved by a variety of mechanisms, including introduction of a disruption of the coding sequence, e.g., insertion of one or more stop codons, insertion of a DNA fragment, etc., deletion of coding sequence, substitution of stop codons for coding sequence, etc. In sonic cases the exogenous transgene sequences are ultimately deleted from the genome, leaving a net change to the native sequence. Different approaches may be used to achieve the "knock-out". A chromosomal deletion of all or part of the native gene may be induced, including deletions of the non-coding, regions, particularly the promoter region, 3' regulatory sequences, enhancers, or deletions of gene that activate expression of genes. A functional knock-out may also be achieved by the introduction of an anti-sense construct that blocks expression of the native genes (See, e.g., Li and Cohen (1996) *Cell* 85:319-329). "Knock-outs" also include conditional knock-outs, for example where alteration of the target gene occurs upon exposure of the animal to a substance that promotes target gene alteration, introduction of an enzyme that promotes recombination at the target gene site (e.g. Cre in the Cre-lox system), or other method for directing the target gene alteration postnatally.

A "knockin" of a target gene means an alteration in a host cell genome that results in altered expression or function of a native target gene. Increased (including ectopic) or decreased expression may be achieved by introduction of an additional copy of the target gene, or by operatively inserting a regulatory sequence that provides for enhanced expression of an endogenous copy of the target gene. These changes may be constitutive or conditional, i.e. dependent on the presence of an activator or represser. The use of knockin technology may be combined with production of exogenous sequences to produce the transgenic animals of the invention.

A selection marker can be any nucleic acid sequence that is detectable and/or assayable. Examples of selection markers include positive selection markers and negative selection markers. Positive selection markers include drug resistance genes; e.g., neomycin resistance genes or hygromycin resistance genes, or beta-galactosidase genes. Negative selection markers, e.g., thymidine kinase gene, diphtheria toxin gene and ganciclovir are useful in the heterologous gene construct in order to eliminate embryonic stern (ES) cells that do not undergo homologous recombination. The selection marker gene is usually operably linked to its own promoter or to another strong promoter from any source that will be active or can easily be activated in the cell into which it is inserted; however, the marker gene need not have its own promoter attached as it may be transcribed using the promoter of the light-generating fusion protein gene to be suppressed. In addition, the marker gene will normally have a polyA sequence attached to the 3'

"Enhancer elements" include nucleic acid sequences that are bound by polypeptides associated with transcription, and are usually in cis with the nucleic acid encoding a light-generating fusion protein. Examples of enhancer elements include cyclic AMP response elements (CRE), serum response elements (SRE), nuclear factor B (NF-κB), activator protein 1 (AP-1), serum response factor (SRF), and p53 binding sites. These enhancer elements may further include a TATA box.

The heterologous gene construct may be constituitively expressed in the transgenic mammal. The gene construct may expressed in specific tissues, e.g., the construct is under the control of a tissue-specific promoter.

EXAMPLE 1

General Methods

Mouse Colony and Tumor Analysis:

All mice were housed and treated in accordance with protocols approved by the institutional care and use committees for animal research at the Dana-Farber Cancer Institute and the University of North Carolina. The LSL-K-

$ras^{G12D}$ mice (K-ras) were provided in a mixed genetic background by Dr. Tyler Jacks. All cohorts in Table I were of a similar, mixed genetic background (~75% C57B1/6, ~25% FVB/n and 129 SvEv). Over 500 mice were analyzed in a standard manner for Table I, but CRE-treated littermates of less informative genotypes (e.g. compound heterozygotes, etc.) and animals treated with empty adenovirus are not shown in the interest of brevity. In all cases, heterozygote mice showed tumor-prone phenotypes intermediate to the wild-type and homozygous mutant animals. For CRE-expression, $5 \times 10^4$ pfu adenoviral-CRE (purchased from University of Iowa adenoviral core) was administered intranasally as previously described[19,23].

Western Blotting and mRNA Analysis:

Western blot assays were performed as previously described[38] with antibodies against $p16^{INK4a}$ (M-156, Santa Cruz), Arf (ab-80, Abcam), Actin (C-1, Santa Cruz), Lkb1 (Rabbit polyclonal antibody, 1:5000 dilution), tubulin (clone DM 1A, Sigma-Aldrich Co), p63 (4892, Cell signaling). Expression of mRNA was analyzed by quantitative TaqMan real-time PCR as previously described with some modifications[39]. Reactions were carried out using cDNA equivalent to 80 ng RNA and performed in triplicate for each sample, 18S rRNA was used as a loading control for all reactions. Primer set for 18S (Hs99999901_s1) was purchased from Applied Biosystems; $p16^{INK4a}$ and Arf primers were generated as previously described[39].

TABLE I

Comparison of lung cancer cohorts:

| Genotype | # treated | Median survival (wks)# | Tumor Mult.& | Squamous or Mixed Histology | Metastasis | Comments |
|---|---|---|---|---|---|---|
| KRas. | 26 | 24 | Med. | 0 of 16 | 0 of 19 | See also [19, 23-25]. |
| $Lkb1^{L/-}$ or $^{L/L}$ | 15 | >40 | NA | NA | NA | No tumors observed |
| $p53^{L/L}$ | 16 | >40 | NA | 0 of 1 | NA | See also [28]. |
| $p16^{INK4a}$-/- $p53^{L/L}$ | 15 | 29 | Low | 0 of 5 | NA | High frequency of fatal pulmonary hemorrhage. |
| KRas $p16^{INK4a}$-/- | 19 | 24 | Med. | 0 of 12 | 3 of 15 (20%) | |
| KRas $p53^{L/L}$ | 17 | 14 | High | 0 of 9 | 4 of 9 (44%) | Compare with [26]. See also [24, 27]. |
| KRas Ink4a/Arf-/- | 26 | 22 | High | 0 of 11 | 0 of 11 | Compare with [26]. |
| KRas $Lkb1^{L/+ \text{ or } +/-}$ | 27 | 19 | High | 0 of 18 | 7 of 22 (32%) | |
| KRas $Lkb1^{L/L \text{ or } L/-}$ | 56 | 9 | High | 15 of 27 (56%) | 27 of 44 (61%) | 2 of 27 mice also demonstrated Large Cell histology |

Median Latency shown is after Adeno-CRE treatment at 5-6 weeks of age, estimated by Kaplan Meier analysis.
&Tumor multiplicity: Low < 3 per lung section, Medium = 3-10 per lung section, High > 10 per lung section Histology and Immunohistochemistry Mice were sacrificed and the left lungs were dissected. The right lung and mediastinal structures were inflated with neutral buffered 10% formalin for 10 minutes and fixed in 10% formalin overnight at room temperature. Fixed tissues were embedded in paraffin, sectioned at 5 m, and Hematoxylin and eosin (H&E) stained (Department of Pathology in Brigham and Women's Hospital). Immunohistochemical analyses were performed as described. The antibodies used were: CCSP (sc-9772, Santa Cruz), SPC (AB3786, Chemicon), pan-Keratin (Z0622, Dako), p63 (ab3239, Abeam), p-AMPK (2535, Cell signaling), Phospho-Acetyl-CoA Carboxylase (Ser79) (3661, Cell Signaling), and VEGFc (2712, Cell signaling).

In Vitro Analyses:

Murine Embryo Fibroblasts (MEFs) cultured from day 13.5 embryos were serially passaged in DMEM (GIBCO)+ 10% Fetal Bovine Serum (Sigma), 50M -mercaptoethanol. (Sigma), and pen/step antibiotic (Invitrogen) on a 3T9 protocol at 21% 0.2. For Lkb1 replacement, late passage (P18) $Lkb1^{-/-}$ MEFs or A549 cells (ATCC) were transduced with either pBABE-puro, or pBABE-Lkb1 (wild-type), or $pBABE-Lkb1^{K78I}$, selected with 1 g/ml puromycin for 4 days, and then harvested for RNA and protein after 4 days without selection. For conditional excision of Lkb1, $Lkb1^{L/-}$ MEFs were treated with $10^{10}$ PFU/mL of Adenoviral-CRE or Adenoviral-Empty for 24 hours. Cells were then passaged according to 319 protocol for an additional 15 days.

Soft Agar Assay

Parental A549 cell and A549 stable cell lines with expression of wt LKB1 and LKB1 K781 cells EGFR-expressing NIH-3T3 cells were suspended in a top layer of RPM111640 containing 10% FBS and 0.4% Select agar (Gibco/Invitrogen) at 5,000 cells per well in triplicate in 6-well plates and plated on a bottom layer of RPM11640 containing 10% FBS and 1% Select agar. After 2-wk culture, cells were stained with 0.5 ml of Crystal Violet for 1 hour. The colonies were then counted in triplicate wells from ten fields photographed with a 10×objective.

In Vivo Lung Seeding Assay of NSCLC Cell Lines

Parental A549 cell and A549 stable cell lines with expression of wt. LKB1 and LKB1 K78I cells were injected into SCID mice intravenously via tail veins. After 8-week of inoculation, the mice were sacrificed and the lungs were dissected for both gross inspection and histology analysis.

Statistical Analysis

Tumor-free survival and comparisons of tumor numbers and colonies in soft agar were analyzed using Graphpad Prism4. Statistical analysis were performed using nonparametric Mann-Whitney test. Comparisons of mRNA levels were made using the unpaired student t-test. All error bars indicate +/− standard error of the mean (SEM).

Microarray Analysis

Figure 3:
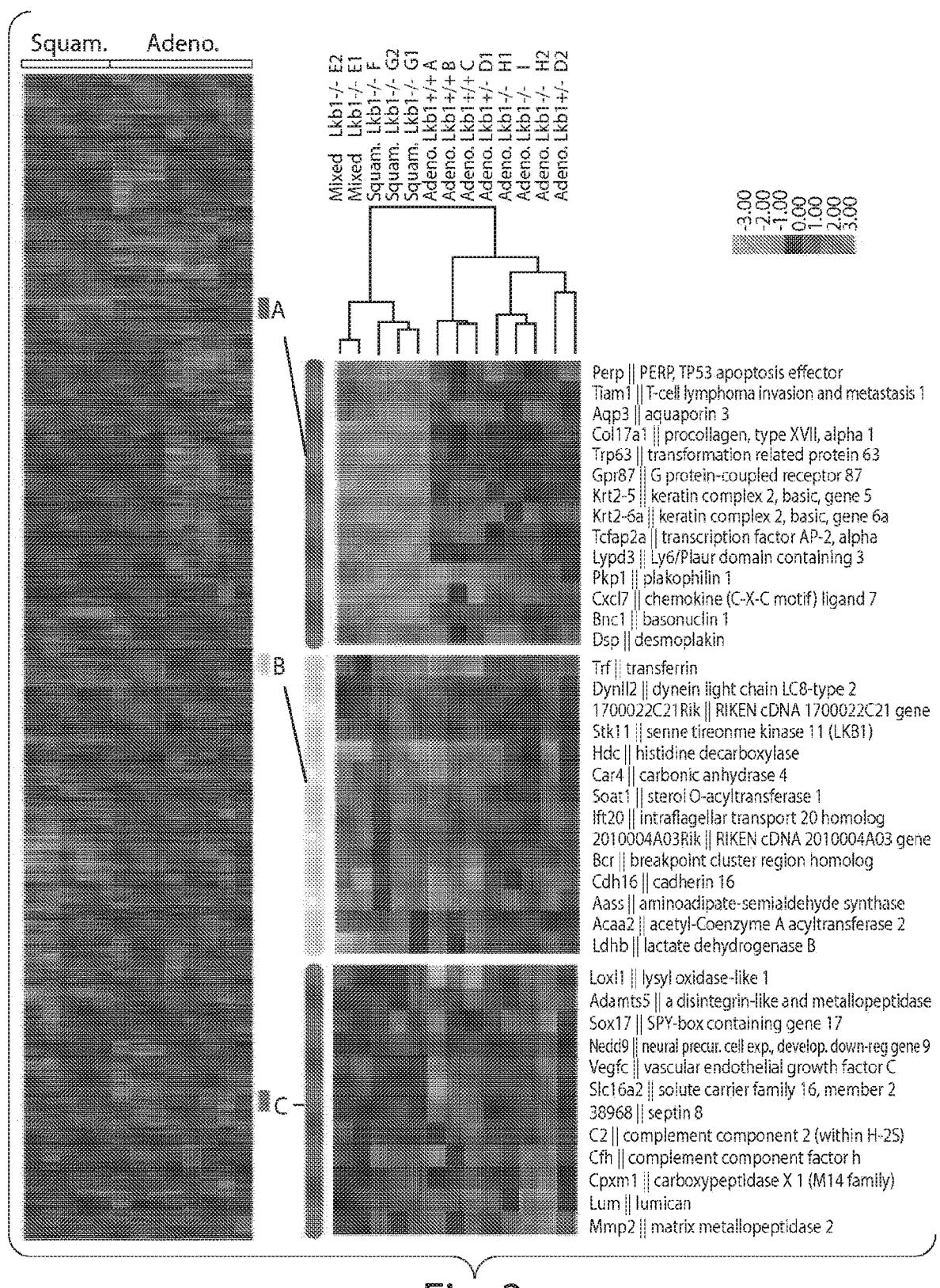
FIG. 3 is a schematic illustration of microarray analysis of K-ras-induced lung tumors. Two-way unsupervised hierarchical clustering was performed on 6,781 unique and dynamic transcripts (left). Excerpted gene clusters are shown at the right. Genes in blue are overexpressed in human SCC and genes in red are known regulators of metastasis. Lkb1 (Stk11) is indicated in orange.

Total RNA was extracted, amplified and labeled as described (Giovanni et al) and hybridized to Mouse430A2 GeneChip Arrays (Affymetrix, Santa Clara, Calif.) representing 22690 unique transcripts. Probe level intensity CEL tiles were preprocessed using the. Robust Multichip Average[40-42] as implemented in Bioconductor (http://www.bioconductor.org/). Gene expression data were filtered using low stringency, pre-defined criteria: probe set intensity (>32 in all samples) and dynamic variation (more than 2-fold over the entire sample set). After filtering, 9239 probe sets remained upon which unsupervised 2-way hierarchical clustering was performed (We can put a reference here if we have the space: Eisen M B, Spellman P T, Brown P O, Botstein D: Cluster analysis and display of genome-wide expression patterns. Proc Natl Acad Sci USA 1998, 95(25): 14863-14868). Multiple probe sets that presented the same genes were collapsed by taking the median value for that gene per array yielding 6871 unique genes, upon which 2-way hierarchical clustering was performed (FIG. 3). Excerpted clusters are shown in FIG. 3. 1).

EXAMPLE 2

Analysis of Tumor Suppressor Function of LKB1 in Context with Activation of K-RAS and In Vivo Lung Cancer Mice Model To discern the relationship among tumor suppressor lesions in lung carcinogenesis, a conditionally activatable Lox-Stop-Lox K-ras$^{G12D}$ (hereafter K-ras) allele[19] and four conditional (L/L) or germline null (−/−) alleles: Lkb1$^{L/L}$ (Ref.[15]) p53$^{L/L}$ (Ref.[20]), Ink4a/Arf−/− (Ref.[21]), and p16$^{INK4a}$−/− (Ref.[22]) were intercrossed. Somatic, lung-specific K-ras activation and/or tumor suppressor inactivation was accomplished through inoculation of young adult mice (5-6 weeks of age) with adenoviral-CRE by inhalation as reported[19,23]. This method transduced a small percentage of pulmonary cells, predominantly of the medium airways. Animals were sacrificed at scheduled time points or for morbidity, and comprehensive autopsies performed to determine tumor number, histology, invasion and metastasis (See, Table I). Control animals of each genotype were treated with empty adenovirus, but no tumors were noted in any cohort in the absence of transient CRE expression.

Isolated K-ras activation led to tumors with high multiplicity but relatively long latency and low aggressiveness. In contrast, concomitant p16$^{INK4a}$ and p53 inactivation in animals lacking the activatable K-ras allele produced infrequent, but highly lethal, hemorrhagic tumors; suggesting that K-ras mutation initiates tumorigenesis while p16$^{INK4a}$ and p53 constrain tumor progression (See, Table I). Potent cooperation was noted between somatic K-ras activation and somatic loss of p53. In contrast to the overexpression setting, however, only modest cooperation was noted between single copy K-ras mutation and p16$^{INK4a}$ inactivation alone or in combination with Arf (Ink4a/Arf−/−) inactivation (See, Table I). These data demonstrate that p16$^{INK4a}$ and p53 combine to suppress pulmonary tumorigenesis, but highlight a more prominent tumor suppressor role for p53 than p16$^{INK4a}$ or Arf in response to single-copy K-ras mutation in the lung.

Surprisingly, however, the strongest genetic interaction between any two alleles was that seen when K-ras mutation was combined with homozygous Lkb1 inactivation (See, Table I and FIG. 1a). The median survival for K-ras Lkb1$^{L/L\ or\ L/-}$ mice was 9 weeks after Cre-inoculation compared with a 14 week median survival seen in K-ras p53$^{L/L}$ mice, the next most tumor-prone cohort. Significant cooperation was also noted between K-ras activation and heterozygous Lkb1 mutation; although loss of the wild-type allele was not seen in the tumors of heterozygous mice inactivation of Lkb1 alone was not sufficient for pulmonary neoplasia, as Lkb1$^{L/L\ or\ L/-}$ mice did not develop tumors after Cre-treatment in the absence of K-ras activation (See, Table I and FIG. 1a). In accord with their more rapid clinical progression, mice harboring simultaneous K-ras mutation and Lkb1 loss showed an increased frequency of metastasis. Additionally, tumors from these mice showed an enhanced spectrum of tumor histology relative to the other genotypes analyzed (See, Table I). These data demonstrate potent in vivo cooperation between K-ras activation and Lkb1 loss in lung tumorigenesis.

EXAMPLE 3

Figure 1B:
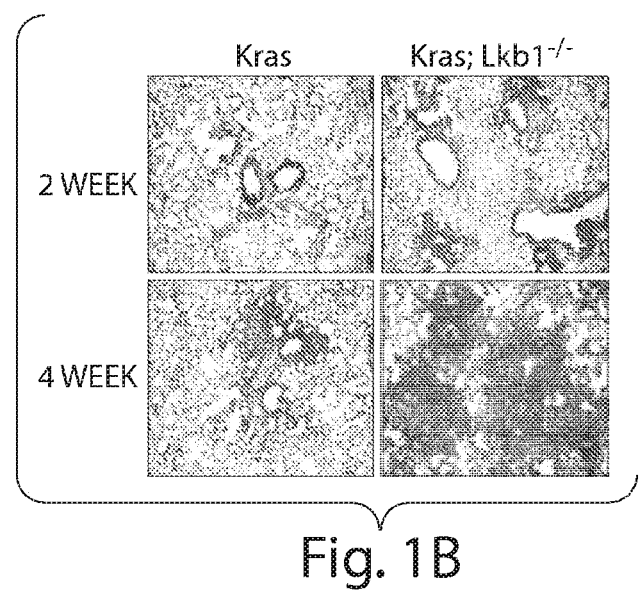
FIG. 1B are photographs illustrating representative histology of lesions in K-ras or K-ras Lkb$^{L/L}$ mice treated with adeno-CRE at 2 weeks (top) or 4 weeks (bottom) after treatment. Photographs are 100× original magnification.
Figure 1C:
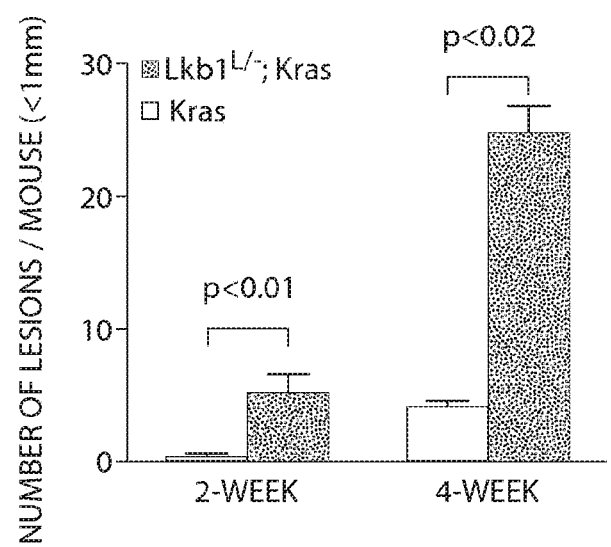
FIG. 1C is a bar chart showing the quantification of early lesions (<1 mm) found in K-ras or K-ras Lkb1$^{L/L}$ mice after treatment with adeno-CRE. 2 week group consisted of K-ras (n=5) and K-ras Lkb1$^{L/L}$ (n=6) mice, and 4 week groups consisted of K-ras (n=4) and K-ras Lkb1$^{L/L}$ (n=5) mice. Error bars represent +/− standard error of the mean (SEM).
Figure 1D:
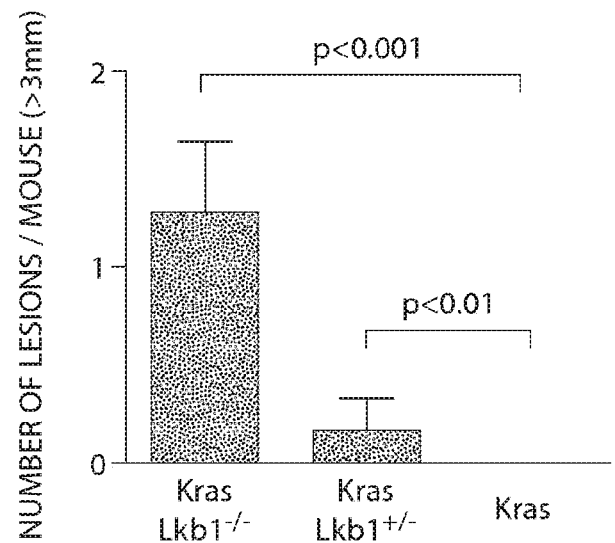
FIG. 1D is a bar chart showing the quantification of tumors of <3 mm in size from K-ras Lkb1$^{L/L\ or\ L/-}$ (n=12), K-ras Lkb1$^{-/-}$ (n=8) and K-ras (n=10) mice 8 weeks after adeno-CRE treatment. Error bars represent +/− SEM.

Evaluation of the Cooperation Between K-Ras Activation and Lkb1 Loss in Lung Tumorigenesis Time course experiments were performed to better delineate the cooperation between K-ras activation and Lkb1 loss in lung tumorigenesis. (FIGS. 1b-d). Two weeks after treatment with Adeno-CRE, there were few discernable lesions in the lungs of K-ras mice, while K-ras Lkb1$^{L/L\ or\ L/-}$ mice harbored a significantly increased tumor burden, which was pronounced by 4 weeks (FIGS. 1b, c). In addition to facilitating the formation of pulmonary lesions after K-ras activation, Lkb1 loss clearly enhanced progression: at eight weeks post-CRE treatment, large tumors (>3 mm) were seen with high frequency in K-ras Lkb1$^{L/L\ or\ L/-}$ or K-ras Lkb1$^{+/-}$ mice, but not in animals harboring K-ras activation alone (FIG. 1d). Even after 28 weeks of observation, tumors greater than 3 mm were not seen in K-ras mice. These results indicate that Lkb1 efficiently constrains lung tumor initiation within days of somatic K-ras activation, as well as tumor progression at later time points.

Figure 1E:
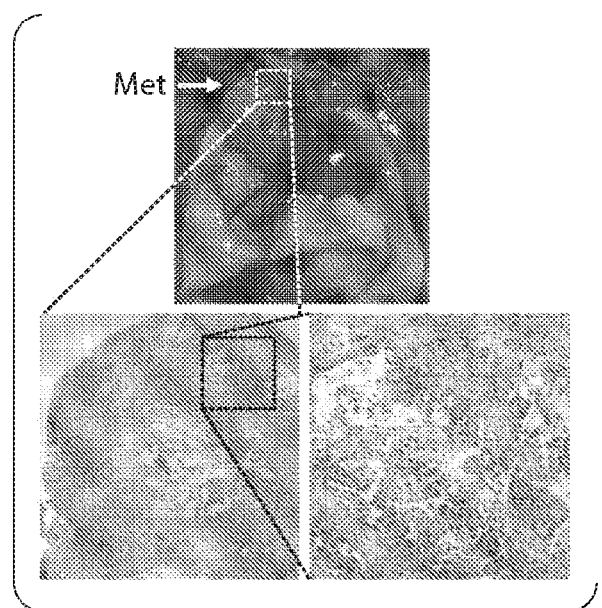
FIG. 1E is a photograph illustrating that mice lacking Lkb1 have increased metastasis. Representative photographs of lymph node metastasis from K-ras Lkb1$^{L/L\ or\ L/-}$ mice. Dissection showed that this was a lymph node separate from the lung itself. Note the adenocarcinoma histology, which was found in all metastatic lesions.

Local invasion or metastasis was not observed in in K-ras mice. In contrast, lung tumors from K-ras Lkb1$^{L/L\ or\ L/-}$ mice displayed local invasion into the pleura as well as metastases to lymph nodes and bone. Regional lymph node metastasis was observed in approximately one fourth of K-ras Lkb1$^{+/-\ or\ L/-}$ mice, and in the majority of K-ras Lkb1$^{L/L\ or\ L/-}$ mice (FIG. 1e, Table 1). Metastasis to the axial skeleton of four K-ras Lkb1$^{L/L\ or\ L//-}$ mice and one K-ras Lkb1$^{+/}$ mouse (Table 1) were noted. These results suggest reduced Lkb1 gene dosage facilitates metastasis in K-ras-induced lung cancers.

Figure 2A:
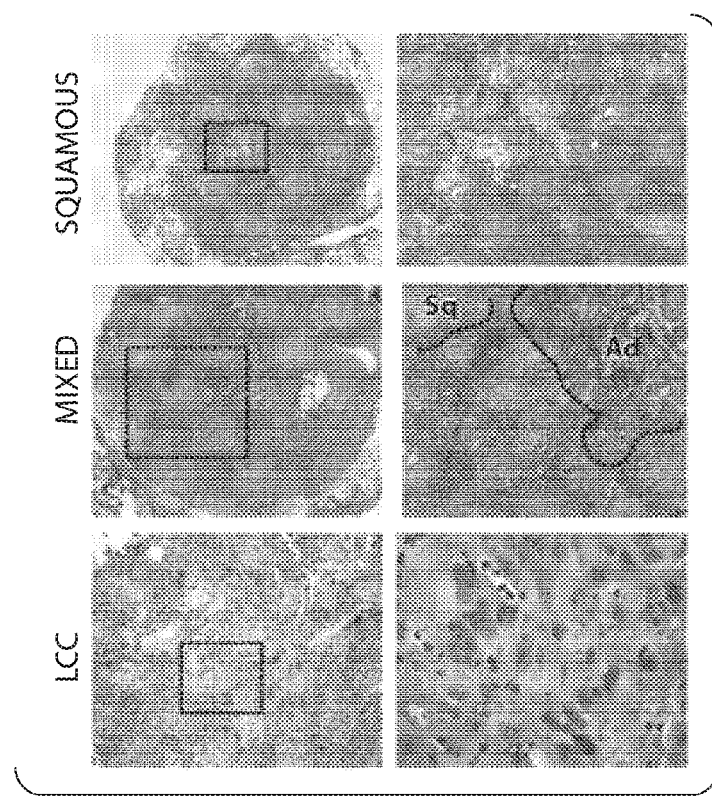
FIG. 2A are photographs showing K-ras Lkb1$^{L/L\ or\ L/-}$ tumors have mixed histology. Representative tumors from K-ras Lkb1$^{L/L\ or\ L/-}$ mice showing squamous histology (top), mixed histology (middle) or large cell histology (bottom).

Analysis of tumors from K-ras Lkb1$^{L/L\ or\ L/-}$ mice revealed distinct differences in tumor histopathology compared to tumors in the other cohorts listed in Table I. Consistent with prior reports[19,24-28], all tumors from K-ras mice with or without Ink4a/Arf or p53 inactivation were of the characteristic adenocarcinoma subtype, as were tumors from p16$^{INK4a}$−/− p53$^{L/L}$ mice. In contrast, the lungs 17 of 27 Adeno-CRE treated K-ras Lkb1$^{L/L\ or\ L/-}$ mice demonstrated a histology other than pure adenocarcinoma: 15 of 27 lungs harbored squamous cell carcinoma (SCC) or adenosquamous tumors (mixed) and 2 of 27 lungs showed large cell carcinoma (LCC) (FIG. 2a). Importantly, even though K-ras Lkb1$^{L/L\ or\ L/-\ (or\ +/-)}$ mice demonstrated decreased survival and increased metastasis (Table I), the metastatic tumors did not demonstrate squamous histology. These data indicate that Lkb1 modulates lung tumor differentiation.

EXAMPLE 4

Lkb1 Modulates Lung Tumor Differentiation

Analysis of tumors from K-ras Lkb1$^{L/L\ or\ L/-}$ mice revealed distinct differences in tumor histopathology compared to tumors in the other cohorts listed in Table I. Consistent with prior reports[19,24-28], all tumors from K-ras mice with or without Ink4a/Alf or p53 inactivation were of the characteristic adenocarcinoma subtype, as were tumors from p16$^{INK4a}$-/- p53$^{L/L}$ mice. In contrast, the lungs 17 of 27 Adeno-CRE treated K-ras Lkb1$^{L/L\ or\ L/-}$ mice demonstrated a histology other than pure adenocarcinoma: 15 of 27 lungs harbored squamous cell carcinoma (SCC) or adenosquamous tumors (mixed) and 2 of 27 lungs showed large cell carcinoma (LCC) (FIG. 2a). Importantly, even though K-ras Lkb1$^{L/L\ or\ L/--\ (or\ +/-)}$ mice demonstrated decreased survival and increased metastasis (Table I), the metastatic tumors did not demonstrate squamous histology. These data indicate that Lkb1 modulates lung tumor differentiation.

EXAMPLE 5

Protein Expression Analysis

Figure 2B:
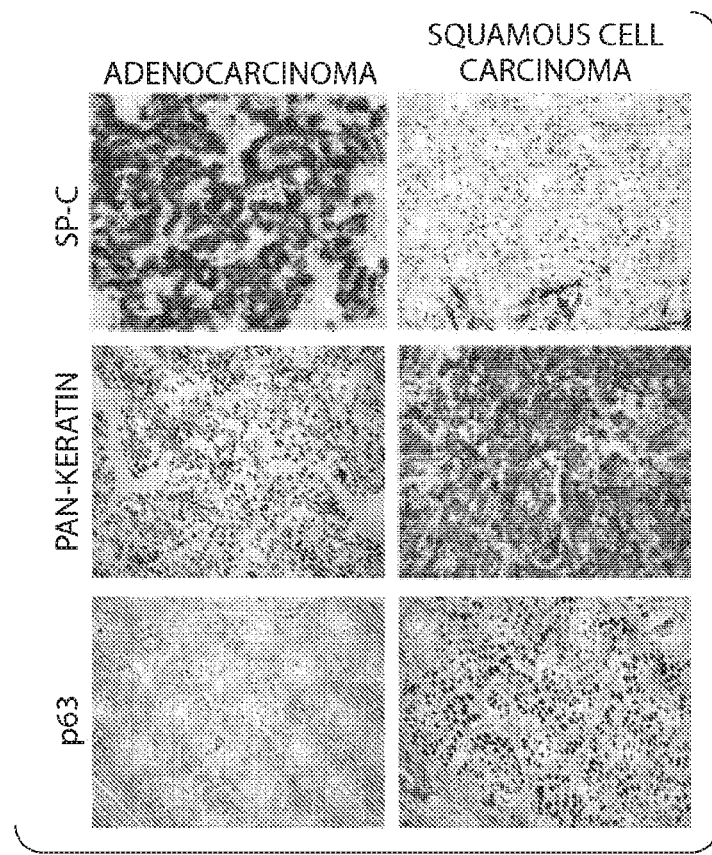
FIG. 2B are photographs showing immunohistochemical staining of tumors from K-ras Lkb1$^{L/L\ or\ L/-}$ mice. Adenocarcinomas (left) show high levels of prosurfactant protein C (SP-C), while squamous tumors (right) show strong staining for pan-keratin and p63. All pictures at 200× original magnification
Figure 2C:
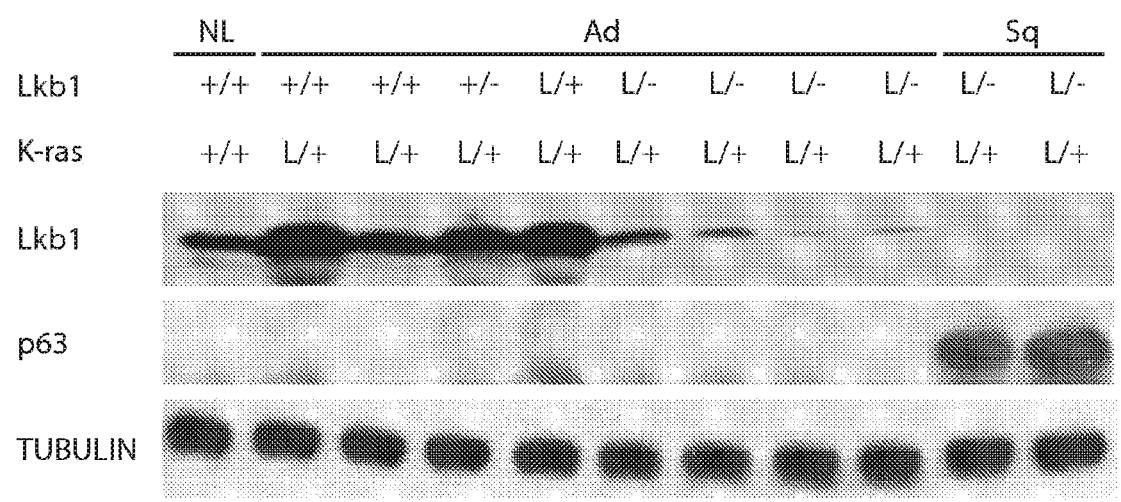
FIG. 2C is a photograph of a Western blot analysis of Lkb1 and p63 expression in tumors from mice of indicated genotype. Tubulin serves as a loading control.

Protein expression analyses confirmed these differences in tumor histology. Squamous tumors from K-ras Lkb1$^{L/L\ or\ L/-}$ mice did not stain for pro-surfactant protein C (SP-C), a marker of type II pneumocytes expressed in lung adenocarcinoma, but did demonstrate strong staining for pan-keratin and p63, markers of SCC (FIG. 2b). In contrast, expression of pan-keratin and p63 was tow or absent in adenocarcinoma. Western blot analysis of tumors from K-ras Lkb1 mice showed that p63 was only expressed in squamous tumors lacking Lkb1 expression (FIG. 2c). While some adenocarcinomas from K-ras Lkb1$^{L/L\ or\ L/-}$ mice demonstrated very low expression of Lkb1, immunostaining suggested that this was stromally derived in at least some of these tumors (data not shown). Therefore, complete absence of Lkb1 expression appeared consistent with each of ale four observed histologies: adenocarcinoma, squamous carcinoma, large cell carcinoma, and mixed tumors, whereas retained Lkb1 expression was only noted in adenocarcinomas.

EXAMPLE 6

RNA Expression Profiling

To study the mechanism whereby loss of Lkb1 modifies the histological versatility and malignancy of lung cancer, RNA expression profiling was performed of lung tumors with or without Lkb1 loss (FIG. 3). Thirteen tumors from 10 K-ras mice of the indicated histologies and Lkb1 genotypes were analyzed using Affymetrix arrays. Expression data were normalized, filtered, and collapsed as described in the methods, and unsupervised hierarchical clustering was performed using 6,871 unique and dynamic transcripts. This unbiased analysis revealed three discrete groups of tumors with regard to gene expression. The most distinct group (E-G) was comprised of squamous or adenosquamous (mixed) tumors from K-ras Lkb1$^{L/L\ or\ L/-}$ mice. These tumors showed a marked increase in the expression of genes (e.g. p63, Krt5, desmoplakin, PTH-like peptide, Sox2; Cluster A) known to be overexpressed in human squamous lung cancer compared to adenocarcinoma[29-31]. The full 135 gene list of the squamous cluster (r>0.85) appears in Supp. Data File 2. These tumors also demonstrated a sharply reduced expression of the Lkb1 (Stk11) transcript (Cluster B). Therefore, loss of Lkb1 expression is associated with tumors harboring a transcriptional profile that is highly similar to that of human squamous lung cancers.

Based on gene expression, the adenocarcinomas further clustered into two groups that were specified by Lkb1 expression. Tumors A-C from K-ras Lkb1$^{+/-}$ mice showed high expression of Lkb1 and several other transcripts associated with carbohydrate metabolism (e.g. Acetyl-CoA acyltransferase and lactate dehydrogenase; Cluster B). DAVID analysis[32] suggested that the 235 transcripts that strongly correlated (r>0.86,) with Lkb1 expression were significantly enriched for genes involved in ATP synthesis as well as metabolism of fatty acids and carbohydrates, consistent with the known role of Lkb1 in regulating the nutrient-sensing AMPK pathway[33]. Correspondingly, these tumors harbored increased expression of the active, phosphorylated forms of AMPK and an AMPK target (Acetyl Co-A carboxylase or ACC) compared to tumors lacking Lkb1. The other group of adenocarcinomas, from K-ras Lkb1$^{L/+\ or\ L/-}$ mice (tumors D, H and I), were characterized by reduced, but not necessarily absent, expression of Lkb1. In accord with the increased frequency metastasis of this group (Table I), these tumors also demonstrated increased expression of several genes associated with angiogenesis and/or metastasis. For example, the 461 gene cluster (r>0.65, Supp. Data File 4) surrounding Cluster C contained Nedd9, Vegf-c, lys1 oxidases (Lox, Lox11 and Lox13), Pdgf's (A, B and C), Pdgf receptor, and MMP2. Increased Vegf-c expression was confirmed by immunohistochemical analysis (Supp. FIG. 2). In particular, several of the pro-metastasis transcripts in Cluster C are targets of hypoxia-inducible factors (HIF), consistent with the hypothesis that LKB1 loss activates HIF signaling[34]. Moreover, as previously reported[27], these metastatic adenocarcinomas appeared more fibrotic by trichrome staining, consistent with increased expression of exctracellular matrix proteins (e.g. Fibronectin and Vimentin) in this cluster. Therefore, Lkb1 appears to activate metabolic regulators and repress metastasis genes in K-ras induced lung adenocarcinomas.

EXAMPLE 7

In Vitro Analysis

Figure 4A:
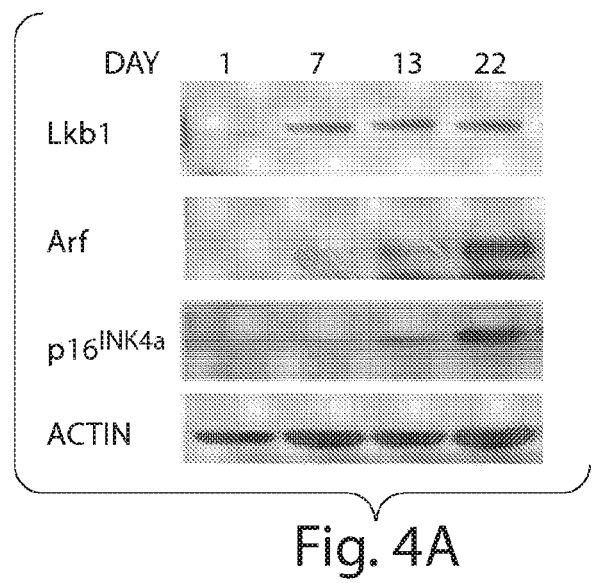
FIG. 4A is a photograph of a blot showing MEFs increase p16$^{INK4a}$ and Arf protein with passage. Cells were serially passaged and assessed for Lkb1, p16$^{INK4a}$, or Arf expression. Actin serves as a loading control. Lysates represent a pool of two independent lines. Lkb1$^{-/-}$ or Ink4a/Arf$^{-/-}$ MEFs serve as negative controls (−).
Figure 4B:
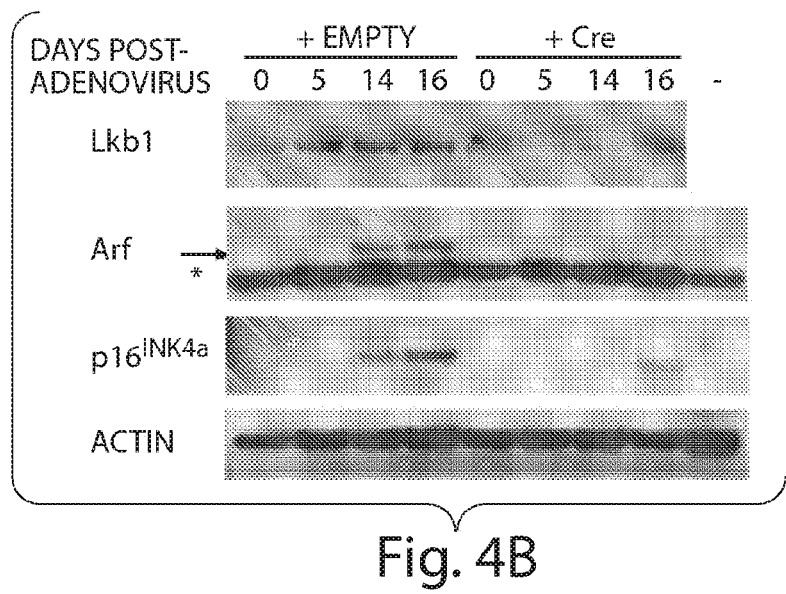
FIG. 4B is a is a photograph of a blot showing Excision of Lkb1 reduces accumulation of p16$^{INK4a}$ and Arf protein. Western blot analysis of Lkb1, p16$^{INK4a}$, and Arf protein levels at various times after adenoviral treatment. Actin serves as a loading control. * designates a non-specific background band. Arrow designates Arf protein.
Figure 4C:
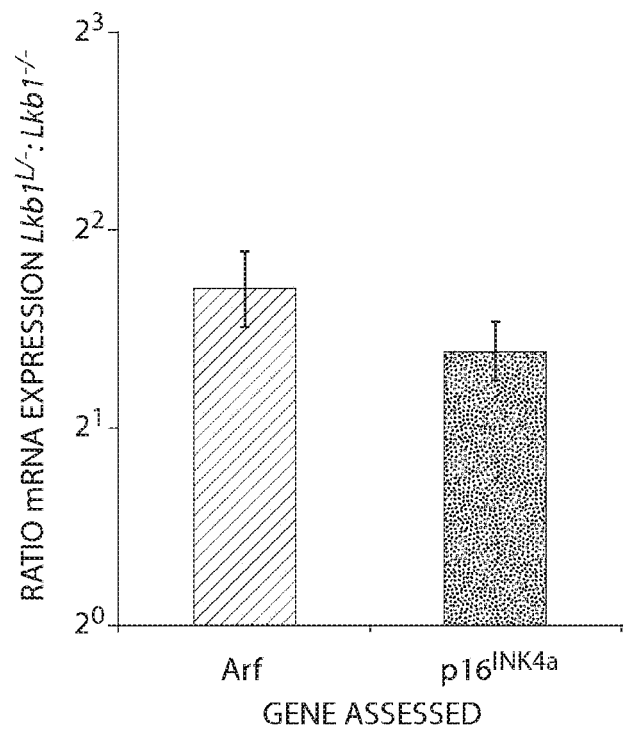
FIG. 4C is a bar chart showing excision of Lkb1 reduces accumulation of p16$^{INK4a}$ and Arf mRNA MEFs. Taqman Real-Time PCR analysis of p16$^{INK4a}$ or Arf levels in MEFs 16 days after conditional excision of Lkb1 by adenoviral-CRE. Values represent ratio of mRNA levels in Lkb1$^{L/-}$ (treated with adeno-empty) to mRNA levels in Lkb1$^{-/}$ (treated with Adeno-CRE). Data represent 4 independent experiments. Error bars represent+/−SEM.
Figure 4D:
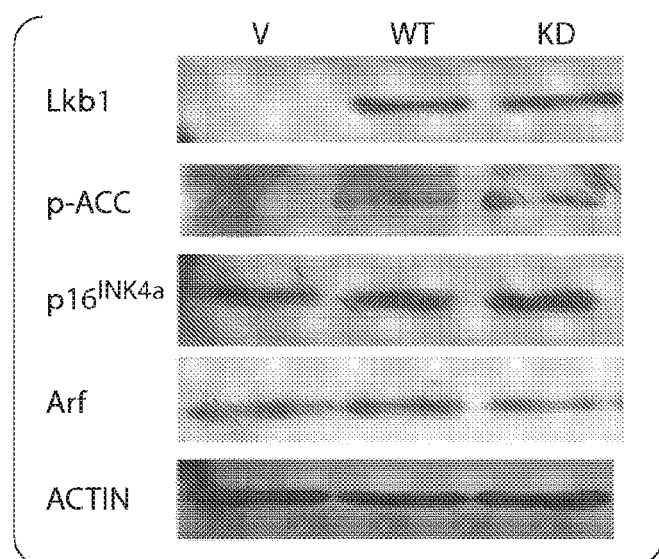
FIG. 4D is a photograph of a blot showing forced expression of Lkb1 in Lkb1−/− MEFs does not affect p16$^{INK4a}$ or Arf levels. Late passage (P10) Lkb1−/− MEFs were transduced with either pBABE (V), pBABE-Lkb1 (WT), or kinase dead pBABE-Lkb1$^{K78D}$ (KD). Levels of Lkb1, p16$^{INK4a}$, Arf, and phosphorylated acetyl CoA carboxylase-2 (p-ACC) were assessed 8 days after transduction. Actin serves as a loading control.

In an effort to further delineate these disparate anti-cancer functions of Lkb1, in vitro analyses was performed. Previous reports have suggested that loss of Lkb1 and p16$^{INK4a}$ are mutually exclusive in human lung adenocarcinoma[3], and that loss of Lkb1 attenuates expression of p16$^{INK4a}$ and Arf protein in response to oncogenic Ras in murine embryo fibroblasts[15]. Cultured murine embryo fibroblasts (MEFs) was used to examine the relationship between Lkb1 and expression of the Ink4a/Arf tumor suppressor locus. Upon culture, wild-type MEFs demonstrated a rapid increase in Lkb1 protein expression which preceded the culture-induced expression of p16$^{INK4a}$ and Arf (FIG. 4a). Inactivation of Lkb1 expression through CRE expression in Lkb1$^{L/-}$ MEFs substantially reduced the passage-dependent increase in p16$^{INK4a}$ and Arf protein (FIG. 4b) and mRNA (FIG. 4c). This effect was likely due to changes in transcription, as no difference in mRNA decay rate was seen for the Arf transcript between Lkb1$^{L/-}$ and Lkb1$^{-/-}$ MEFs (not shown). Re-introduction of wild-type Lkb1 or Lkb1$^{K78I}$, a kinase-dead mutant, into wild-type or Lkb1$^{-/-}$ MEFs did not, however, result in a further increased p16$^{INK4a}$ or Arf expression (FIG. 4d). Therefore, Lkb1 activity cooperates with culture-induced stresses to potentiate Ink4a/Arf transcription in MEFs, but Lkb1 appears unable to enhance Ink4a/Arf expression after culture-induced activation of the locus. As K-ras Ink4a/Arf-/- mice show enhanced tumor progression compared to K-ras mice (Table I), transcriptional activation of Ink4a/Arf expression may in part explain the anti-progression effects of Lkb1 in mice with somatic K-ras activation. As K-ras Ink4a/Arf−/− and K-ras p53$^{L/L}$ mice are less tumor-prone than K-ras Lkb1$^{L/L\ or\ L/-}$ mice and do not develop squamous tumors, however, clearly some effects of Lkb1 on tumor progression and differentiation are independent of p16$^{INK4a}$ and Arf-p53.

Figure 5A:
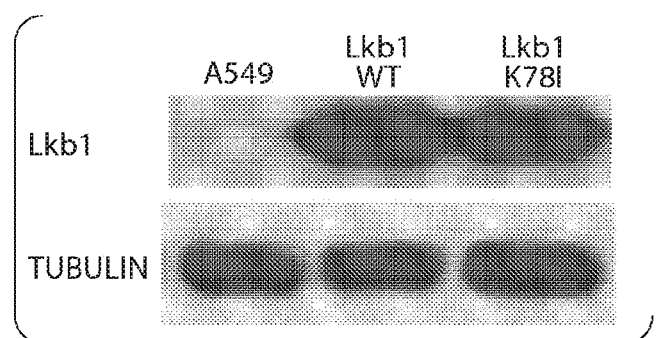
FIG. 5A is a photograph of a blot showing expression of exogenous LKB1 in A549 cells. A549 cells were stably transduced with either pBABE-LKB1 (WT), or kinase dead pBABE-LKB1$^{K78D}$ (KD) via retroviral infection and assessed for expression of LKB1 by western blotting. Tubulin serves as a loading control.
Figure 5B:
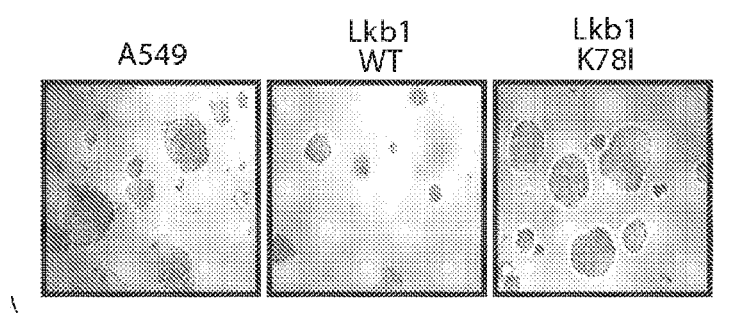
FIG. 5B is a phptograph showing that LKB1 suppresses colony formation in soft agar. A549 cells stably transduced with either pBABE-LKB1 (WT), or kinase dead pBABE-LKB1$^{K78D}$ (KD) were assessed for the ability to form colonies in soft agar. Representative photographs of 4 independent experiments.
Figure 5C:
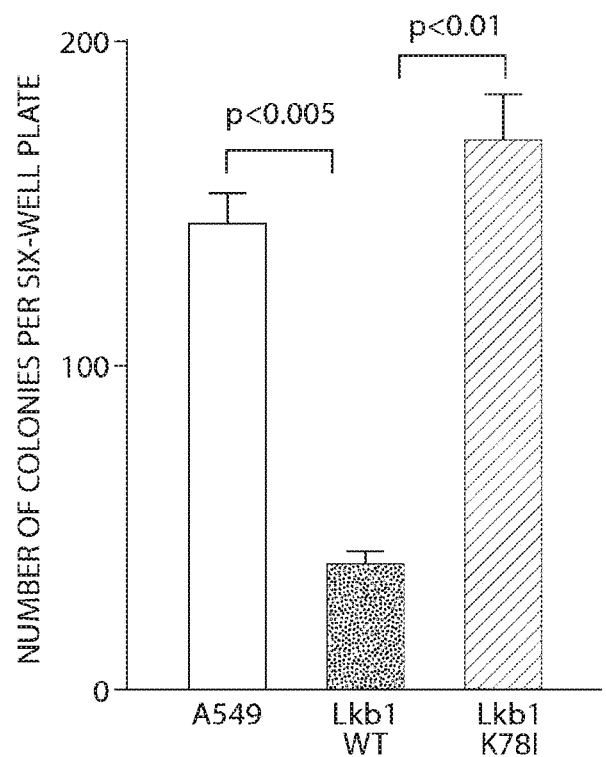
FIG. 5C is a bar chart sshowing that LKB1 suppresses colony formation in soft agar. A549 cells stably transduced with either pBABE–LKB1 (WT), or kinase dead pBABE-LKB$^{K78D}$ (KD) were assessed for the ability to form colonies in soft agar. Average number of colonies per well from 4 independent experiments. Error bars indicate+/−SEM.
Figure 5D:
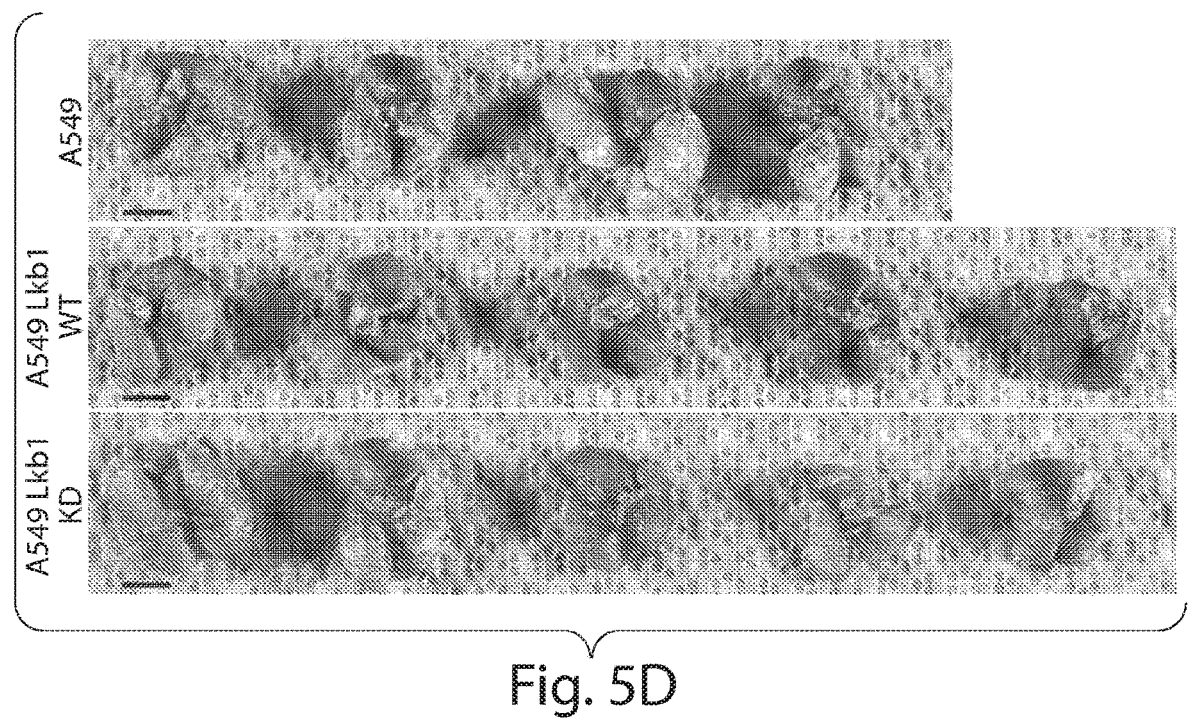
FIG. 5D is a photograph illustrating that exogenous LKB1 suppresses metastasis in SCID mice. A549 cells were stably transduced with either pBABE-LKB1 (WT), or kinase dead pBABE-LKB1$^{K78D}$ (KD) and injected into the tail vein of SCID mice. Representative photographs of lungs.
Figure 6:
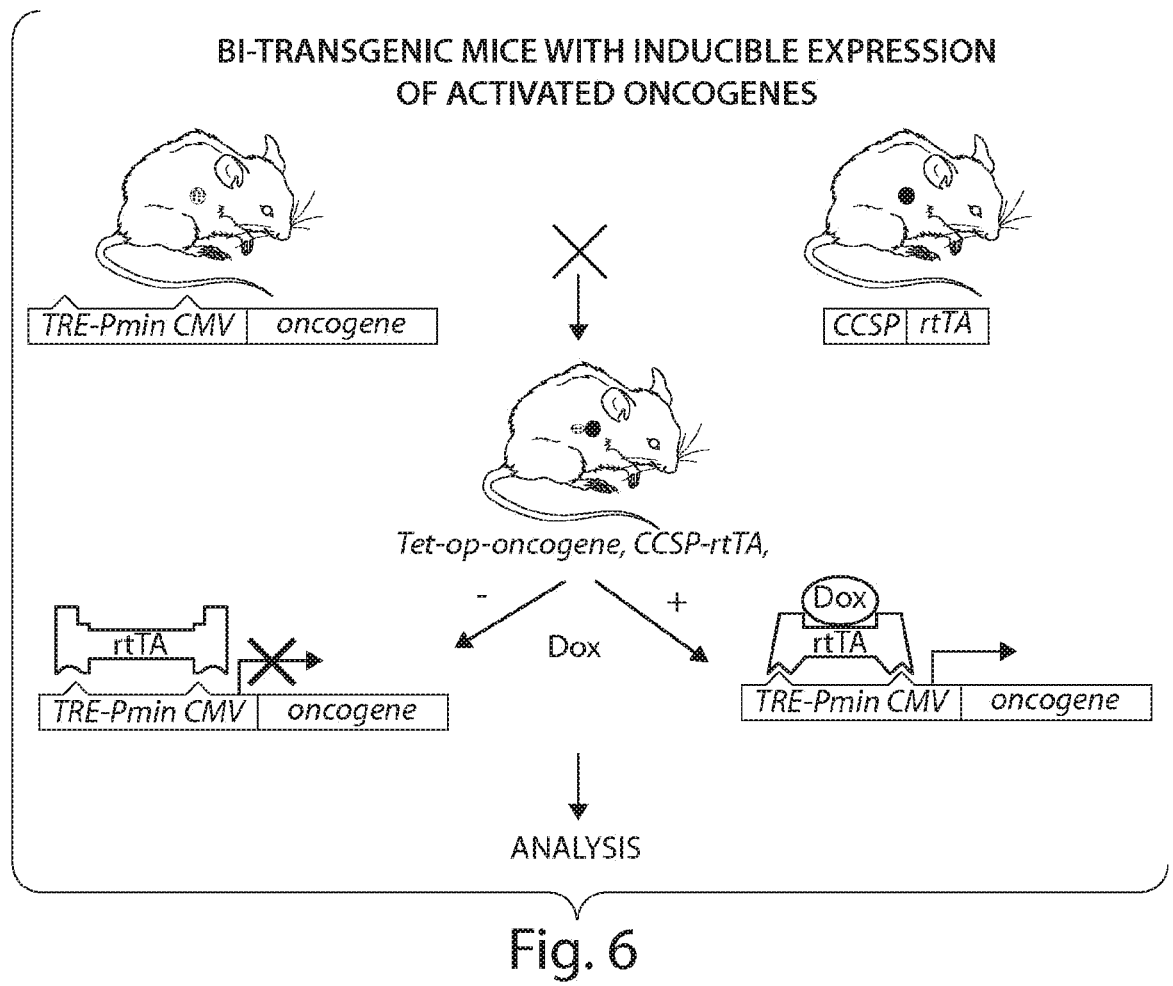
FIG. 6 is a schematic illustrating the tetracycline bitransgenic regulatory system.
Figure 7:
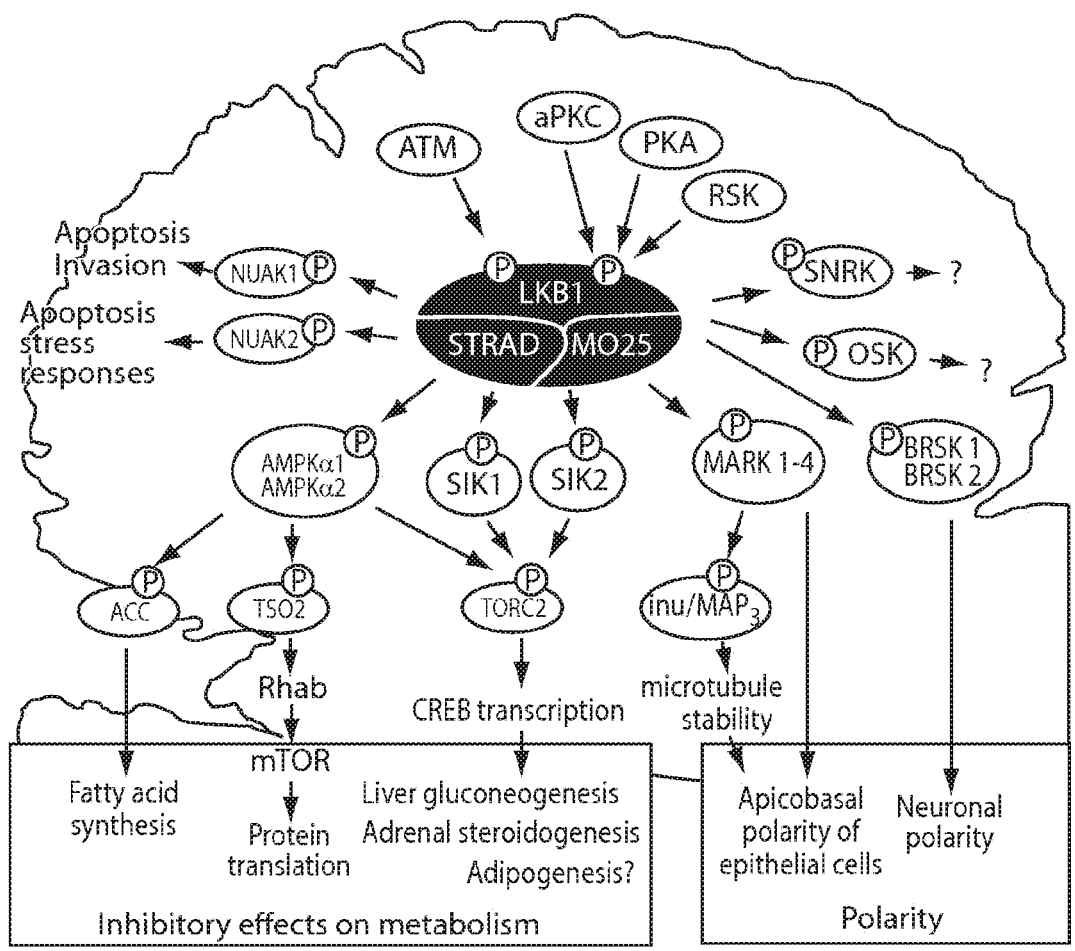
FIG. 7 is a schematic illustrating the Lkb1 signaling pathways linking it to DNA damage response, growth control and cell polarity FIG. 8 are line graphs showing Power (red) and type 1 error rates (green) for detecting mean differences of 0.58, 1, 1.32, and 1.58, plotted against the number of genes truly exhibiting a mean difference of 0.58, 1, 1.32, and 1.58, assuming 15 samples for each cohort.

To investigate the INK4a/ARF-independent effects of LKB1 on metastasis, A549 cells, a human lung carcinoma cell line, that harbor a K-RAS activating mutation was and lack INK4a/ARF and LKB1 expression was used. A549 cells stably expressing equivalent LKB1 or LKB1$^{K78I}$ were established (FIG. 5a) through transduction with amphotropic retrovirus. Although the in vitro proliferation was not dramatically different among the lines regardless of LKB1 expression (data not shown), the A549-wt LKB1 cells demonstrated a profound inability to form colonies in soft agar (FIG. 5b, c) or metastasize to the lung after tail-vein injection in SCID mice (FIG. 5d). The suppression of metastasis by LKB1 required its kinase activity, as A549-LKB1$^{K78I}$ cells demonstrated soft agar growth and metastasis comparable to the parental A549 line (FIG. 5b-d). These results, are consistent with the genetic data (Table I) as well as a prior report[13], suggest that LKB1 kinase activity represses lung cancer metastasis independent of INK4a/ARF function.

EXAMPLE 8

Genetical Dissection and Comparison of the Role of Lkb1 in the Initiation and Progression of K-Ras, EGFR, and BRAF Mutant-Driven Lung Tumorigenesis Multiple cytogenetic and molecular studies have shown that there are many genetic changes in human lung carcinomas resulting in the inactivation of tumor suppressor genes and mutation/activation of oncogenes[61,62]. Thus, it is virtually certain that in lung carcinomas (or other tumor types) that K-ras, EGFR, or BRAF mutants are not the sole mutation that occurs. Furthermore, these additional genetic alterations likely play important roles in the initiation and progression of tumorigenesis as well as sensitivities of the tumors to treatments. LKB1 mutations appear to be relatively common (~25%) in NSCLC and thus, are likely to occur concurrently with K-ras, EGFR and BRAF mutations. A recent study suggested that LKB1 mutations are commonly found with K-RAS mutations in human lung cancers. It has been recently shown that Lkb1 cooperates with K-ras mutant to shorten the latency of lung tumorigenesis in the lox-stop-lox K-ras knock-in model (See, examples above). These preliminary findings will be confirmed in the tet-op K-ras G12D mouse model. This is important, as the lox-stop-lox K-ras model has a different level (endogenous level) of K-ras expression than the tet-op K-ras model (overexpression), and this might have a differential effect on tumorigenesis. Furthermore, the K-RAS locus is commonly amplified in human NSCLCs, thus suggesting K-RAS is over-expressed in this tumor type. Similarly, it will be determined whether Lkb1 deficiency will synergize with EGFR and BRAF mutations in lung tumorigenesis and if the tet-op-K-ras cohorts can serve as a positive control.

The inventors have generated and characterized the doxycycline inducible tet-op-K-ras, tet-op-EGFR, tet-op-BRAF mutant alleles Upon induced expression of K-ras, EGER or BRAF mutant in the lung epithelial cells, these mice develop lung adenocarcinomas with a latency of 12 to 16 weeks (See.

Examples above) To specifically delete the Lkb1 conditional alleles in the same lung cells that express mutant K-ras, EGFR, or BRAF, a recently generated SPC-Cre-ER$^{T2}$ allele will be employed. The SPC promoter will direct the expression of the Cre-recombinase/estrogen receptor (Cre-ER$^{T2}$) mutant fusion protein specifically in the lung type II pneumocytes epithelial cells (in the same cell compartment that are expressing the K-ras/EGFR/BRAF mutants. The administration of tamoxifen will activate the Cre recombinase activity. Using these unique alleles, the following 12 cohorts of mice (30 mice in each cohort) will be generated:

1. Lkb1 L/L, tet-op-K-ras G12D, CCSP-rtTA, SPC-Cre-ER$^{T2}$ (no doxy and no tamoxifen: control)
2. Lkb1 L/L, tet-op-K-ras G12D, CCSP-rtTA, SPC-Cre-ER$^{T2}$ (no doxy and tamoxifen: control)
3. Lkb1 L/L, tet-op-K-ras G12D, CCSP-rtTA, SPC-Cre-ER$^{T2}$ (doxy and no tamoxifen: control)
4. Lkb1 L/L, tet-op-K-ras G12D, CCSP-rtTA, SPC-Cre-ER$^{T2}$ (doxy and tamoxifen: experimental cohort)
   1a. Lkb1 L/L, tet-op-EGFR L858R, CCSP-rtTA, SPC-Cre-ER$^{T2}$ (no doxy and no tamoxifen: control)
   2a. Lkb1 L/L, tet-op-EGFR L858R, CCSP-rtTA, SPC-Cre-ER$^{T2}$ doxy and tamoxifen: control)
   3a. Lkb1 L/L, tet-op-EGFR L858R, CCSP-rtTA, SPC-Cre-ER$^{T2}$ (doxy and no tamoxifen: control)
   4a. Lkb1 L/L, tet-op-EGFR L858R, CCSP-rtTA, SPC-Cre-ER$^{T2}$ (doxy and tamoxifen: experimental cohort)
   1b. Lkb1 L/L tet-op-BRAF V600E, CCSP-rtTA, SPC-Cre-ER$^{T2}$ (no doxy and no tamoxifen: control)
   2b. Lkb1 L/L, tet-op-BRAF V600E, CCSP-rtTA, SPC-Cre-ER$^2$ (no doxy and tamoxifen: control)
   3b. Lkb1 L/L, tet-op-BRAF V600E, CCSP-rtTA, SPC-Cre-ER$^{T2}$ (doxy and no tamoxifen: control)
   4b. Lkb1 L/L, tet-op-BRAF V600E, CCSP-rtTA, SPC-Cre-ER$^{T2}$ (doxy and tamoxifen: experimental cohort)

At 3 weeks of age, mice from cohorts 2, 4, 2a, 4a, 2b, and 4b will be injected intraperitionally with 4 mg of tamoxifen over a 5-day period to activate the Cre-recombinase activity in the type II pneumocytes and delete the Lkb1 alleles as described above.

Mice from cohorts 3, 3a, 3b, 4, 4a, and 4b will be administered doxycycline continuously through their drinking water to activate the expression of mutant K-ras, EGFR, and BRAF. During these experiments, mice will be inspected daily Monday through Friday. Any mouse that show evidence of respiratory distress or illness will be euthanized (along with age-matched controls from the other cohorts) and subjected to analysis. To determine if the loss of Lkb1 affects overall survival of these mice, 10 mice from each cohort will be followed until it is time for them to be euthanized and a Kaplan-Meier survival curve will be generated. Of note, the person deciding which mice should be euthanized will be blinded regarding their specific genotypes. In addition to measuring effects on survival, we will also determine if loss of Lkb1 affects K-ras, EGFR, and BRAF mutant-induced tumor burden. For these studies, three mice from each cohort will be sacrificed by $CO_2$ inhalation at 3, 6, 9, 12, 15, and 18 weeks after continuous administration for the lung tumor burden analyses and assessment of Lkb1 signaling. At the time of sacrifice, each organ from the mouse, including the heart, bones, liver, spleen, brain, kidney, and adrenal glands will be microscopically inspected for visible signs of metastases. Additionally, these organs will be fixed in formalin for subsequent detailed histological analyses. The left lung will be removed and snap-frozen in liquid nitrogen for protein, DNA, and RNA analyses. When macroscopic tumors are evident, they will be dissected out of the tumor to enable tumor specific molecular studies. The right lung (with the left main bronchus ligated with a suture) will then be inflated at 25 cm $H_2O$ pressure with 10% buffered formalin for 10 minutes via of an intratracheal catheter. The right lung will then be removed and fixed in 10% buffered formalin for 24 hours before embedding in paraffin, Serial mid-sagittal sections (5 µM thickness) will be obtained for histological analysis.

Data on the histological types, lung tumor multiplicity as well as the grade of the tumor will be tabulated on each lung. Paraffin-embedded lung is cut in to 4 um sections, stained with H&E and tumor-quantified using Bioquant software; specifically, the size and number of specific tumors are determined. Using this software, lung sections are captured in a 2×field and a line is drawn around the periphery of the lung. The software then calculates the area of the tumor (mm). The same tools are used to determine the size of each tumor in the lung (total tumor area/total lung area X 100). These measurements will be compared at different time points after Cre activation. Experiments will be performed at all six time points (5 mice of each genotype per time point).

EXAMPLE 9

Assessment of LKB1 Signaling in Lung Tumors

Lung tumors will be evaluated by western blot and IHC analyses to probe the activity of the known LKB1 signaling two scores are multiplied to give an overall score of 0-9, of which 0-2 is considered negative, 3-6 moderate, and 7-9 strong staining. The second method of scoring examines the intensity of staining of tumor cells compared to adjacent normal cells. Here, the intensity of staining in greater than 50% of the tumor is compared to the intensity of staining in adjacent normal glands on the same slide and scored on a scale of 1-3, where 1=tumor staining less than normal, 2=tumor equivalent to normal and 3=tumor greater than normal. A score of 3 is considered as overexpression. The choice of the scoring method will depend on the antigen. Controls for the specificity of an antibody used for IHC will include tumor derived from xenografts that are known to express or not express a given protein as determined by western blot analysis. Data will be collected on the intensity and frequency of staining using immunohistochemistry and a semi-quantitative scoring system will be used as described above. Furthermore, tumors will be categorized as positive or negative. For example, for the first scoring method described above, scores 0-2 and 3-6 would be grouped together as "negative," and scores 7-9 would he "positive." The most appropriate groupings will be determined empirically for each antigen. The list of antibodies suitable for use in this analyses are listed in Table 2.

| Antibody | epitope | Company | Cat |
| --- | --- | --- | --- |
| Phospho-AMPKalpha (Thr172) (40H9) Rabbit mAb | PT172 | Cell Signaling | 2535S |
| Phospho-Acetyl-CoA Carboxylase (Ser79) Rabbit polyclonal Ab | pS79 | Cell Signaling | 3661S |
| Phospho-S5 Ribosomal Protein (Ser235/236) Rabbit polyclonal Ab | pS235/236 | Cell Signaling | 2211S |
| Phospho-Akt (Ser473) (736E11) Rabbit mAb | pS473 | Cell Signaling | 3787 |
| Phospho-p44/42 MAP Kinase (Thr202/Tye204) (20G11) Rabbit mAb | pT202/pY204 | Cell Signaling | 4376 |
| Phospho-EGF Receptor (Tyr1068) Rabbit polyclonal Ab | pY1068 | Cell Signaling | 2234 |
| Akt1 isofom specific (2H10) Mouse mAb | NA | Cell Signaling | 4057 |
| SPC | amino acids of 1-33 of human Pro-Surfactant Protein C | Cell Signaling | 07-647 |
| CC10 (T-18) | epitope near the C-terminus of mouse CC10 | Cell Signaling | sc-9972 |
| Raf-B (H-145) | N/A | Cell Signaling | SC-9002 |
| VEGF (Ab-7) Clone VG1 | N/A | Cell Signaling | Ab-7 |
| antiLKB1.clone 5c10 | 1-433 of human LKB1 | Cell Signaling | 05-832 | pathway. When tumors arise, they will be evaluated by IHC, using specific antibodies against LKB1 to ensure the loss of LKB1 and antibodies against P-S6 Kinase and P-S6 as readouts for activated mTOR signaling. IHC will be performed Drs. Padera, using previously described methods. Colored signal will be generated with a combined secondary antibody-peroxidase kit (Envision+, DAKO, Carpinteria, Calif.), according to the manufacturer's instructions. The slides will be evaluated the pathologists using light microscopy to select and analyze the 100×-magnification field with the highest concentration of positive-staining tumor cells with a clear background. Positive cases are defined by the presence of membrane, cytoplasmic, or nuclear staining, depending on the antigen. The grading of antigen expression is performed independently by at least two of the pathologists. The presence of positive staining in in situ lesions is noted. Scoring of invasive tumor is performed by two methods as previously described[69]. In the first method, scores of 0-3 are assigned according to the percentage of positive tumor cells (0=0%; 1=<25%; 2=25-50%; 3=>50%) and the intensity of staining (0=0; 1=1+; 2=2+; 3=3+). The Protein, DNA and RNA will be harvested from any found tumors in the left lungs. With these reagents, the level of mutated kinase expression and autophosphorylation will be analayzed as well as the activation status of the various downstream pathways via western blot and expression analyses. The loss of Lkb1 in the tumors from the various cohorts with. genotyping and western analyses will be assessed. All tumors found will also be cultured in an attempt to establish cell lines. These cell lines will greatly facilitate the in vitro signal transduction and drug sensitivity studies.

To determine whether or not the temporal sequence of genetic alterations play differential and distinct roles in the initiation and progression of lung tumorigenesis, the same experiment as outlined above with the same identical cohorts of mice above (30 mice in each cohort), but switch the sequence of Lkb1 inactivation and K-ras/EGFR/BRAF mutant induction. First doxycycline will be administered continuously through the drinking water to all the mice in the cohort. After 8 weeks on doxycycline, two treated mice from each cohort will be sacrificed and their lungs harvested for immunohistochemical staining and western analyses to confirm the expression of the K-ras, EGFR, or BRAF mutant expression and the activation of the downstream pathways. After the confirmation, the remaining 18 mice in each cohort will be injected intraperitionally with fling of tamoxifen over a 5-day period to activate the Cre-recombinase activity in the nucleus to delete the Lkb1 alleles, Three mice from each cohort will be sacrificed by $CO_2$ inhalation at 3, 6, 9, 12, 15, and 18 weeks after tamoxifen treatment for analysis. Identical analyses on these mice as outlined for the initial reverse temporal sequence will be performed.

The results from both sets of experiments will be compared directly, in particular, the histological types, lung tumor multiplicity as well as the grade of the tumor.

Lastly, the following mouse cohorts (30 mice per cohort) will be generated:
1. Lkb1 L/+, tet-op-K-ras G12D, CCSP-rtTA, SPC-Cre-$ER^{T2}$ (no doxy and no tamoxifen: control)
2. Lkb1 L/+, tet-op-K-ras G12D, CCSP-rtTA, SPC-Cre-$ER^{T2}$ (no doxy and tamoxifen: control)
3. Lkb1 L/+, tet-op-K-ras G12D, CCSP-rtTA, SPC-Cre-$ER^{T2}$ (doxy and no tamoxifen: control)
4. Lkb1 L/+, tet-op-K-ras G12D, CCSP-rtTA, SPC-Cre-$ER^{T2}$ (doxy and yes tamoxifen: experimental cohort)
1a. Lkb1 L/+, tet-op-EGFR L858R, CCSP-rtTA, SPC-Cre-$ER^{T2}$ (no doxy and no tamoxifen: control)
2a. Lkb1 L/+, tet-op-EGFR L858R, CCSP-rtTA, SPC-Cre-$ER^{T2}$ (no doxy and tamoxifen: control)
3a. Lkb1 L/+, tet-op-EGFR L858R, CCSP-rtTA, SPC-Cre-$ER^{T2}$ (doxy and no tamoxifen: control)
4a. Lkb1 L/+, tet-op-EGFR L858R, CCSP-rtTA, SPC-Cre-$ER^{T2}$ (doxy and tamoxifen: experimental cohort)
1b. Lkb1 L/+, tet-op-BRAF V600E, CCSP-rtTA, SPC-Cre-$ER^{T2}$ (no doxy and no tamoxifen: control)
2b. Lkb1 L/+, tet-op-BRAF V600E, CCSP-rtTA, SPC-Cre-$ER^{T2}$ (no doxy and yes tamoxifen: control)
3b. Lkb1 L/+, tet-op-BRAF V600E, CCSP-rtTA, SPC-Cre-$ER^{T2}$ (doxy and no tamoxifen: control)
4b. Lkb1 L/+, tet-op-BRAF V600E, CCSP-rtTA, SPC-Cre-$ER^{T2}$ (doxy and yes tamoxifen: experimental cohort)

The same experiments as outlined above for the initial cohorts to determine whether the loss of a single copy of Lkb1 (haploinsufficiency) impact on the phenotypes of the K-ras, EGFR, and BRAF mutant-driven lung tumors.

EXAMPLE 10

Use Pharmacological and Genetic Approaches to Dissect the Role of Dysregulated Pathways Caused by Lkb1 Loss that are Involved in the Initiation and Progression of K-Ras, EGFR, and BRAF Lung Tumorigenesis Lkb1 is implicated in various aspects of cellular metabolism and polarity control. Lkb1 exerts its effects on diverse cellular functions through phosphorylation of different cellular substrates. In addition to the first identified physiological substrate of Lkb1 kinase, AMPK, 13 other AMPK-related serine/threonine kinases have been subsequently identified as Lkb1 substrates. Of these different pathways, the most characterized is the AMPK/TSC1/TSC2/mTOR signaling pathways, as this pathway is frequently activated in various types of cancers. In the preliminary studies, it was revealed in K-ras-driven lung tumors with LKB1 loss had elevated mTOR activity. The role of the activated AMPK/TSC1/TSC2/mTOR pathway caused by the loss of Lkb1 function in worsening the biological behavior of the K-ras LKB1 compound mutant lung tumors will be determined To determine if the activated mTOR pathway is the main cause for the more aggressive phenotype seen in the K-ras/Lkb1 compound mutant lung tumors 78 mice from each of the following cohorts will be generated:
1. Tet-op-K-ras G12D, CCSP-rtTA SPC-Cre-$ER^{T2}$ (control cohort)
2. Tet-op-K-ras G12D, CCSP-rtTA, Lkb1 L/L, SPC-Cre-$ER^{T2}$ (experimental cohort)

Seventy-eight mice will be used for experiments in which Lkb1 is deleted after K-ras-driven tumors are present, and the other 78 mice will be used for experiments in which Lkb1 is deleted before K-ras expression is induced. For the first set of experiments, Lkb1 will be deletaed after K-ras tumors are formed.

In the experiment in which Lkb1 is deleted before K-ras expression is induced, 78 mice at 3 weeks of age from the each cohort will be injected intraperitionally with 4 mg of tamoxifen over a 5 day period to activate the Cre recombinase activity in the nucleus (deleting both alleles of LKB1 in pneumocytes in cohort 2). These tamoxifen-treated animals will be then administered doxycycline continuously through their diet to activate the expression of the mutant K-ras. Concurrently, in each cohort, 26 mice will be treated once daily with 2 mg/kg of rapamycin intraperitionally, 26 mice with 4 mg/kg of rapamycin intraperitionally and 26 mice with placebo vehicle. These dosing schedules are well established and have been shown to inhibit mTOR activity in xenograft models. Eight mice from each of the sub-cohorts will be followed until it is appropriate for them to be euthanized, and a Kaplan-Meier survival curve will be generated. To evaluate the effects of mTOR inhibition on the phenotype of the K-ras LKB1 compound mutant lung tumors, three mice from each sub-cohort will be sacrificed by $CO_2$ inhalation following 3, 6, 9, 12, 15, and 18 weeks of doxycycline treatment. At the time of sacrifice, tumor burden, tumor histology, and inhibition of the mTOR signaling by methods outlined above will be evaluated. If possible, the mice will be sacrificed 4 hours after the administration of the last dose of the drug to ensure uniformity, as serum from the mouse will be collected at the time of harvest to assess rapamycin levels. In addition, any tumor nodules from these tumor-bearing mice will be microdissected out. PCR and southern analyses on DNA isolated from these microdissected tumors will be utilized to verify if the Lkb1 recombination indeed occurs. Furthermore, we will assess tumors via IHC and western blot analysis to document loss of LKB1 protein expression. By comparing the results from the different cohorts, it can be determined if activated mTOR pathway plays a significant rote in the altered phenotype seen in the K-ras Lkb1 compound mutant mice.

The above experiments will allow for the determination of the role of activated mTOR pathway in K-ras Lkb1 mutant lung tumor initiation.

To evaluate the potential differing effects on the initiation and progression of K-ras compound mutant-driven lung tumorigenesis, the same experiments as outlined above will be repeated with the same identical cohorts of mice (80 mice in each cohort). Doxycycline will be administered continuously through their diet to all mice in the cohort. After 8 weeks on doxycycline, two treated mice from each cohort will be sacrificed and their lungs harvested for immunohistochemical staining and western analyses to confirm the expression of the mutant K-ras expression and the activation of the downstream pathways. After the confirmation, the remaining mice in each cohort will be injected intraperitionally with 4 mg of tamoxifen over a 5-day period to activate Cre-recombinase activity to delete the Lkb1 alleles. The remaining 78 mice from each cohort will be divided into 3 sub-cohorts and be administered placebo, rapamycin at 2 mg/kg and rapamycin at 4 mg/kg once daily as outlined above while remaining on continuous doxycycline treatment. Eight mice from each sub-cohort will be utilized to generate Kaplan-Meier survival curves. As described above, three mice from each sub-cohort will be sacrificed by $CO_2$ inhalation following 3, 6, 9, 12, 15, and 18 weeks of doxycycline treatment. At the time of sacrifice, tumor burden, tumor histology, and inhibition of the mTOR signaling will be evaluated by methods outlined above.

As TSC1/TSC2 is directly downstream of AMPK but upstream of mTOR, if the effect seen with loss of Lkb1 in the K-ras/Lkb1 tumors is mainly due to the activated mTOR, pathway, genetic inactivation of the TSC1/TSC2 complex in the K-ras lung tumors should give a similar phenotype as the K-ras Lkb1 mutant mice. A Tsc1 conditional knockout allele into lox-stop-lox K-ras conditional mouse strain (K-ras L/+) will be breed and the following colonies will be generated:

1. Tsc1+/+, K-ras L/30
2. Tsc1 L/L, K-ras L/+
3. Tsc1 L/+, K-ras L/+
4. Lkb1+/+, K-ras L/+
5. Lkb1 L/L, K-ras L/+
6. Lkb1 L/+, K-ras L/+

Tumors will be induced in the K-ras L/+ mice by treating the mice with a recombinant adenovirus expressing Cre recombinase (adeno-Cre) via inhalation as has been done previously. Expression of the Cre recombinase promotes a recombination event that induces expression of the mutant K-ras. In brief, when the mice are ~7 weeks old, they will be anaesthetized with 0.13 ml/kg of Avertin solution. 5 million colony-forming units of adenoviral Cre (purchased from the University of Iowa) will be administered in a solution of MEM and CaCl2. The solution will be applied to the nares of the anesthetized mice. This procedure invariably induces tumors in *M. musculus* and the mice usually become ill from respiratory distress starting at about 8 weeks. During these experiments, mice will be inspected daily, Monday through Friday. Any mice that show evidence of respiratory distress or illness will be euthanized (along with age-matched controls from the other cohorts) and subjected to analysis. To determine if the loss of Tsc1 affects overall survival of these mice and directly compare the results to LKB1 loss, 10 mice from each cohort will be followed until it is time for them to be euthanized and a Kaplan-Meier survival curve will be generated. Of note, the person deciding which mice should be euthanized will be blinded regarding their specific genotypes. In addition to measuring effects on survival, it will also be determined if loss of Tsc1 affects K-ras-induced tumor burden. For these studies, five mice from each cohort will be sacrificed by $CO_2$ inhalation at 6, 8, 12, 18, and 21 weeks after Cre administration for the lung tumor burden and immunohistochemical analyses. At the time of sacrifice, each organ from the mouse, including the heart, bones, liver, spleen, brain, kidney, and adrenal glands we be inspected macroscopically for visible signs of metastases. Additionally, these organs will be fixed in formalin for subsequent detailed histological analyses. The left lung will be removed and snap-frozen in liquid nitrogen for protein, DNA, and RNA analyses. When macroscopic tumors are evident, they will be dissected out of the tumor to enable tumor specific molecular studies. The right lung (with the left main bronchus ligated with a suture) will then be inflated at 25 cm H2O pressure with 10% buffered formalin for 10 minutes via of an intratracheal catheter. The right lungs will then be removed and fixed in 10% buffered formalin for 24 hours before embedding in paraffin. Serial mid-sagittal sections (5 μM thickness) will be obtained for histological analysis. Tumor genotyping will also be performed to confirm recombination and deletion of the Tsc1 locus.

These experiments will determine if loss of Tsc1 effects K-ras mutant-induced tumorigenesis in a similar manner as Lkb1 loss. It is anticipated that loss of Tsc1 will accelerate K-ras tumorigenesis. However, these Lkb1 experiments are necessary controls for direct comparison to the impact Tsc1 loss in K-ras lung tumorigenesis.

To globally determine the effect of LKB1 in K-ras/EGFR/BRAF-driven tumorigenesis expression profiling from the RNA derived from the lung tumor nodules collected from the tumor bearing cohorts (3, 4, 3a, 4a, 3b, 4b) described above will be performed. All the tumors to be profiled will first be confirmed for the presence or absence of Lkb1 by genotyping and immunohistochemical analyses and for their precise histological classification by the three pathologists. It is anticipated that in the K-ras Lkb1 mutant cancers, there will be both adenocarcinomas and squamous cell carcinomas. RNA for profiling from 15 adenocarcinomas from K-ras alone tumors (from cohort 3) and 15 adenocarcinomas from K-ras Lkb1−/− compound mutant tumors (from cohort 4) will be prepared. 15 lung squamous cell carcinomas from the K-ras Lkb1 mutant mouse cohorts will also be collected. It is not expected to have any lung squamous cell carcinomas from the K-ras alone cohort. 15 paired EGFR, EGFR Lkb1−/−, BRAF, BRAF Lkb1−/− adenocarcinomas from the other cohorts will also be collected. If tumors of other histological types emerge from these cohorts, RNA from them will be prepared (up to 15 tumors from each histological subtype) for expression profiling.

Briefly, RNA will be prepared from the mouse tumors generated from the different cohorts using the standard trizol method and digested with DNase 1, and purified through the Qiagen column. The purified RNA will be sent to the Dana-Farber Cancer Institute Microarray Core Facility for expression profiting using the Affymetrix Mouse Expression Array 430A2.0 (22,626 known genes).

Data generated from each profiling will be downloaded as "cel" image files. Low-level analyses will be performed using the dChip software. These analyses will include image analysis (grid alignment, target detection, intensity extraction, and local background correction), normalization based on an invariant set and subsequent median smoothing; and model-based expression indices will be computed for each probe.

High-level analyses of the gene expression data will be performed in the R statistical computing environment. A total of approximately 105 samples (see above) will be expression-profiled to determine the transcriptional level of 22,626 known genes. Gene expression profiles between paired K-ras, EGFR, and BRAF cohorts with and without Lkb1 function will also be compared. In addition, the transcription signature of the K-ras alone driven tumors will also be compared to those driven by EGFR or BRAF alone. Specifically, we will compare gene expression profiles of: (1) K-ras, Lkb1+/+ vs. K-ras, Lkb1−/−, (2) EGFR, Lkb1+/+ vs. EGER, Lkb1−/−, (3) BRAF, Lkb1+/+ vs. BRAF, Lkb1−/−, (4) K-ras, Lkb1+/+ vs. EGFR, Lkb1+/+ vs. BRAF, Lkb1+/+, (5) K-ras, Lkb1−/− vs. EGFR, Lkb1−/− vs. BRAF, Lkb1−/−. Both individual gene analyses and pathway analyses will be performed. For individual gene analyses, individually differentially expressed genes will be studied by performing the comparisons listed above using two-sample t-tests tailored towards micro-array analysis, e.g., using the software package SAM[72,73]. To control for the error rates of a large number of hypothesis tests, the False Discovery Rates will be calculated. Each cohort to be compared will have 15 tumors, and the number of genes to be compared will depend on filtering of unexpressed genes done in the low level analysis.

To assess expected power of our study, preliminary data comparing gene expression profiles of K-ras Lkb1+/+ tumors vs. K-ras Lkb1−/− tumors will be used to estimate the standard errors and a reasonable range of effect sizes and performed power calculations using the method of Tibshirani, which gives estimates of false discovery rates and false negative rates and which is particularly suitable, as it makes few assumptions regarding correlation and variance of genes. Power in this situation is defined as 1-FDR and depends on the mean difference between groups of logged expression values, sample size, and the number of genes that are truly significant for that effect size (for Tibshirani's method this is set equal to the number of genes called significant). Plots of FDR estimates for mean differences of 0.58, 1, 1.32, and 1.58 (corresponding to fold changes of 1.5, 2, 2.5, and 3 for the raw unlogged data) are given below.

Figure 8:
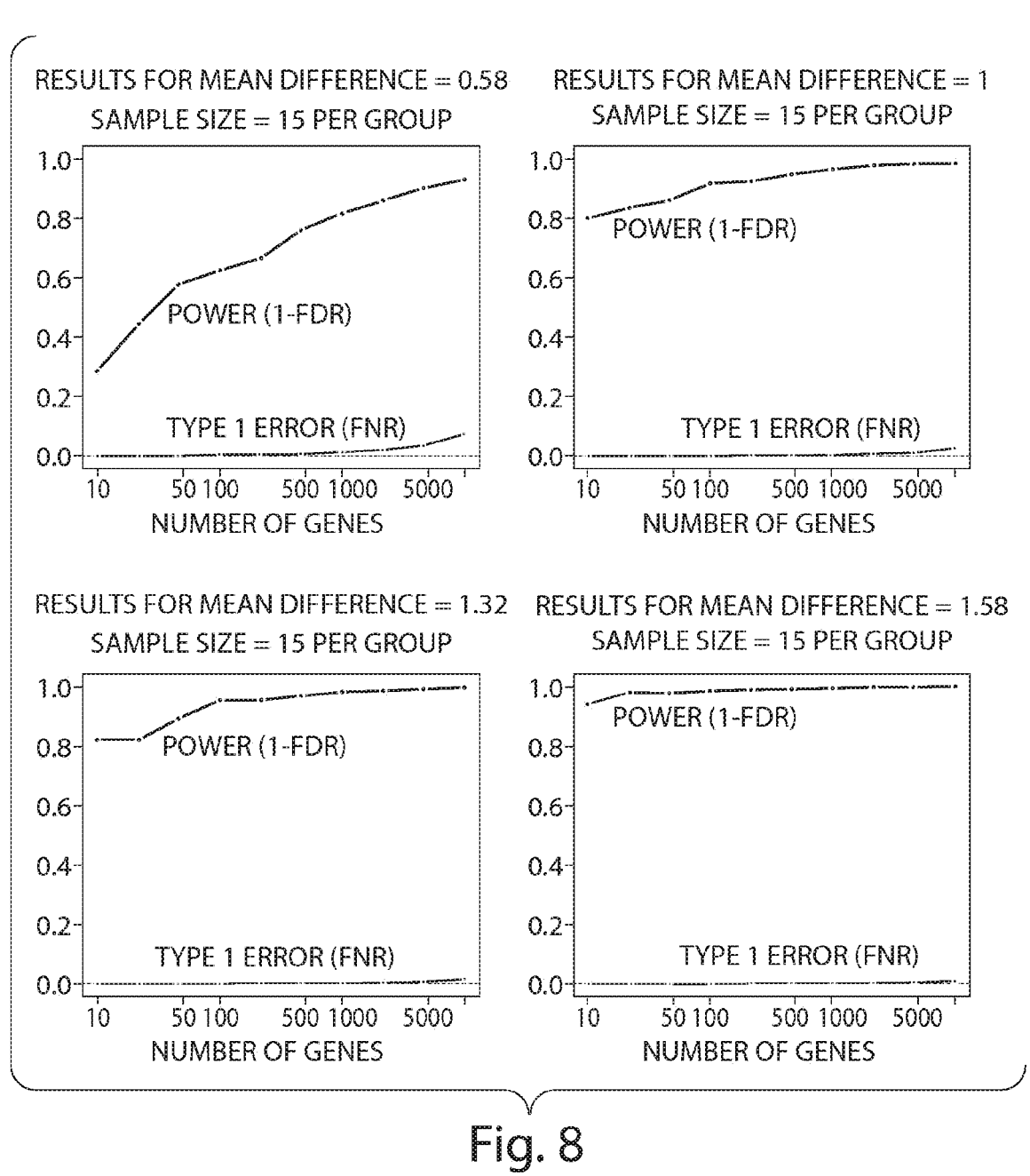

From these plots on FIG. 8 for a sample size of 15 per cohort and a mean difference of 1 unit in the logged scale between two cohorts, it is expected that greater than 80% power if the hypothesized number of genes with a 2-fold change in expression level is between 10 and 100. It is expected to be over 90% power if the hypothesized number of genes with a 2-fold change in expression level is greater than 100. For a mean difference of 0.58 (1.5-fold change in a gene's unlogged expression), we expect greater than 60% power if the true number of genes with a 1.5 fold change is greater than 50. For a mean difference of 1.32 in the log-scale (2.5 fold changes in the original scale), the estimated power is greater than 80% and becomes greater than 90% if the number of such genes is greater than 100. For a mean difference of 1.58 (3-fold change in the original scale) with 100 such genes, the estimated power is greater than 90%. Preliminary data finds that the number of significantly expressed genes is close to 1000 when comparing K-ras, Lkb1+/+ tumors vs. K-ras Lkb1−/− tumors. Hence it is expected that the proposed sample sizes are likely to have excellent power for comparing different cohorts. In each case shown, the estimated false negative rate (type 1 error) is low.

Although individual gene analysis is useful, cellular processes often affect sets of genes. Traditional analyses have focused on individually highly ranked genes. However, this approach suffers from several major limitations: (1) Long lists of individually significant genes without a single encompassing theme are difficult to interpret. (2) Single gene analyses miss important pathway effects as cellular processes often affect sets of genes and individually highly ranked genes are often downstream genes, so moderate changes in many genes may give more insight into biological mechanisms than dramatic change in a single gene. (3) Individual highly ranked genes can be poorly annotated and are often not reproducible from studies to studies. Knowledge-based studies on gene sets, e.g. genetic pathways are more biologically interpretable and reproducible. Biological knowledge based pathway analysis will also be performed. Examples of candidate lung cancer pathways we will consider include the mTOR and the angiogenesis pathway as seen from our preliminary studies. Pathways will be constructed based on: (1) genes demonstrated to be associated with a particular gene ontology term; (2) genes demonstrated to be associated with a particular KEGG pathway; (3) gene lists manually assembled based on the previous literature.

Gene set enrichment analysis (GSEA), the principle component analysis, the global testing approach and logistic version of the kernel machine method can be used to test for modified regulation of entire groups of genes between samples cohorts. GSEA is suitable for comparative tests, while the others are suitable for self-contained tests. Since this pathway analysis is knowledge-based, self-contained tests are more suitable. The Principle Components Analysis method essentially performs dimension reduction by constructing weighted averages of genes comprising a pathway. Weights are based on directions of greatest variability of the genes in the pathway and can be found by finding the eigenvectors corresponding to the largest eigenvalues of the covariance matrix of the genes. Each weighted average can then be considered as a super-gene and we will test for differences in these super-genes between pathways via standard multivariate tests, the Hotelling's $T^2$-test in the two-group comparison case and in the multiple groups setting, MANOVA The principle component analysis is particularly suitable when the number of subjects per group is small. Both the global testing method and the kernel machine method are based on logistic regression by regression cohort status on gene expressions. The global testing method and principal components method can also show which genes, and what combination of genes, drive the difference between cohorts for each pathway. For the global testing method, influence plots are generated while for the principal components analysis method the weights used to find the super-genes indicate the relative importance of each gene in generating a difference. This can potentially elucidate the mechanisms by which a pathway is affected. The logistic analog of the kernel machine method further allows interactions among genes within a pathway when comparing different cohorts.

From the above expression profiling experiments and analyses, it is anticipated that the expression profiling will confirm that the mTOR pathways are hyper-activated in tumors without Lkb1 function. More importantly, it is also anticipated that many novel Lkb1 dependent genes and pathways that are involved in lung cancer progression and metastases will be discovered. In addition, there might be unique Lkb1 cancer relevant pathways that are activated/inactivated depending on the initial oncogenic stimuli. (For example, Lkb1 dependent pathway X is only activated in EGFR mutant driven lung tumors while Lkb1 dependent pathway Y is only activated in K-ras mutant driven lung tumors.) It is also anticipated that the expression profiling to confirm that the mTOR pathways are hyper-activated in tumors without Lkb1 function.

EXAMPLE 11

Determination of the the Impact of Concentrated Ambient Particles (CAPs), an Environmental Insult, on Inflammation, Proliferation, Apoptosis, and LKB1 Function on K-Ras, EGFR, and BRAF Mutant Mice With the generation of different genetically engineered mice that are prone to develop lung cancer, we now have the tools and reagents to examine the environmental interaction with these defined oncogenic stimuli and determine the role of environmental insult on lung cancer initiation and progression. Concentrated air particles (CAPS) system is a well-established and ideal model to dissect the role of air pollution in lung cancer progression through its effect on the primed lung epithelial compartment in our genetically defined lune oncogenic mouse models. It is hypothesized that prolonged CAPs exposure will cause chronic lung inflammation. The chronic lung inflammatory environment will generate reactive oxidative species leading to increased DNA damage, and genetic inactivation of important lung tumor suppressors such as LKB1, and accelerate lung, tumorigenesis. The following series of experiments will test tins hypothesis.

The following 6 cohorts of mice (60 mice per cohort) will be generated:
1. Tet-op-K-ras G12D, CCSP-rtTA, (no doxy: control)
2. Tet-op-K-ras G12D, CCSP-rtTA, (doxy: experimental cohort)
   1a. Tet-op-EGFR L858R, CCSP-rtTA (no doxy: control)
   2a. Tet-op-EGFR L858R, CCSP-rtTA (doxy: experimental control)
   1b. Tet-op-BRAF V600E, CCSP-rtTA, (no doxy: control)
   2b. Tet-op-BRAF V600E, CCSP-rtTA, (doxy: experimental)

At 10 weeks of age, mice from cohort 2, 2a, and 2b will be put on continuous doxycycline diet. All the mice from each of the cohorts will then be randomly divided into two equal groups (30 mice in each sub-cohort). One group of mice will be exposed The Harvard/EPA Ambient Particle Concentrator (HAPC) generates concentrated aerosols of outdoor air particles that can subsequently be directly delivered to animals (described below) for a total of 20 weeks. The other group will be exposed to filtered air in an identical exposure chamber.

The Harvard/EPA Ambient Fine Particle Concentrator (HAPC) will be used to expose animals to concentrated ambient fine particles (0.1-2.5 µm). Boston atmospheres typically consist of particles generated by vehicle exhaust, power plant emissions, home heating, and transported aerosols. Employment of this system allows for the direct investigation of the potential harm of "real world" particles in our genetically defined mouse models. Briefly, the HAPC used for the animal inhalation studies consists of three components: (1) a high-volume conventional impactor with a 2.5-µm cutoff size, (2) a series of three virtual impactors with a 0.1-µm cutoff size (concentrator stages I, II, and III), and (3) an animal exposure chamber. The first impactor is a high-volume conventional impactor (Fractionating Sampler, Anderson, Inc., Atlanta, Ga.) and removes particles larger than 2.5 µm operating at 5000 L/min, while smaller particles escape collection. The deflected flow of the conventional impactor is drawn through a series of three virtual Impactors. Each virtual impactor accelerates all airborne particles in a rectangular nozzle. These particles cross the deflected air streamlines, and enter a slit-shaped collection probe, while particles smaller than 0.1 µm follow the deflected streamlines, or enter the collection probe, but are unlikely to be concentrated. Particles in the size range 0.1-2.5 µm pass through the collection probe and are referred to as the minor flow (20% of the total flow). The minor flow of the third stage virtual impactor contains the concentrated aerosol. The total flow rate into the third stage is 50 L/min, and concentrated particles are supplied to the animal exposure chamber at 40 L/min. The remaining 10 L/min is used for characterization of the aerosol. The total concentration factor for the three virtual impactor stages is about 30. The concentrated air from stage III of the virtual impactor is supplied to the whole-body animal exposure unit (described below) through a manifold connection port on top of the chamber. Sham exposures are also performed in the exposure unit at the same pressure and flow rate with the air passed through a glass fiber filter (Gelman, Type A/E, Ann Arbor, Mich.) connected at the inlet of the chamber to remove particles. The filter efficiency is 99.6-99.9%. The use of the three virtual impactor stages results in a pressure drop of about 10 in H2O. The aerosol flow rate provides for a residence time in the exposure chamber of about 3.5 minutes. This residence time results in minimal particle losses on the chamber wall. The virtual impactor residence time is only a few seconds. The portable chamber for rodent concentrated air particle (CAPs) exposure has a volume of 142 L and is specially designed to fit inside a larger 1000-L stainless steel and glass outer chamber. Because the air pumping units are downstream from the concentrator/inhalation chamber, both the external chamber and the exposure chamber are operated under a negative pressure (~10 in H2O). The chamber is designed to optimally utilize the flow rates from the concentrator to deliver the aerosol to the rodents. A manifold connection port on top of the chamber allows for direct connection to the HAPC. The unit is rectangular in shape with a grated floor to allow waste products to fall into trapezoidal waste collection areas underneath; drain valves in the bottom of the trapezoidal waste collection areas allow for removal of animal waste during exposure. A second manifold on the back of the unit is connected to a negative pressure system to maintain air exchange in the system. Up to six stainless steel wire-mesh cages (holding up to 50 animals each) can be placed into the unit at one time.

CAPs characterization will be performed weekly to ensure that there is no dramatic change in its composition during the course of the experiments using gravimetric particle mass determinations, liquid chromatography for sulfate, X-ray fluorescence for elemental analysis and thermal and optical reflectance method for elemental carbon analyses.

Mice from all the cohorts will be monitored closely for clinical signs of stress or tumors. Any mouse that shows any clinical signs of having stress or tumors will be sacrificed for analyses into the causality and nature of pathology. In addition four mice from each cohort will be sacrificed for analyses at weeks 2, 4, 8, 12, and 16 weeks post CAPs or filtered air exposure. The remaining 10 mice from each cohort are used to generate Kaplan Meier curves.

At the time of sacrifice, each organ from the mouse including the heart, lung, pancreas, liver, spleen, kidney, bladder, and intestines will be inspected macroscopically for signs of abnormality and fix them in formalin for subsequent detailed histological analyses Blood and serum from each mouse via cardiac puncture will also be collected. For the lungs, prior to fixation, bronchioalevolar lavage (BAL) will be performed to obtain fluids and cells. As described above, ligated left lung will be harvested and snap-frozen for subsequent DNA, RNA, and protein analyses. The right lung will then be inflated at 25 mm with 3% glutaraldehyde in 0.1M cacodylte buffer to 25 cm $H_2O$ (for 15 min), then ligated and removed. This procedure would preserve the physiological air space architecture. The lungs collected from the different cohorts will be assessed for tumor burden. The tumors will also be analyzed for loss of Lkb1 via IHC and western analyses as well as activated mTOR pathway.

Bone marrow from the femurs will be harvested to generate primary bone marrow culture suspension. Metaphase spreads from these primary cells derived from the various cohorts will be prepared to quantitatively determine the frequency of chromosomal aberrations caused by chronic oxidative and mutagenic stress from the CAPs. This series of experiments will determine the potency of CAPs as a carcinogen and inducers of DNA double strand breaks.

Immuno-staining with Ki67 antibody will be performed on histological sections of the lungs and the other organs from the six cohorts harvested at the determined time points to assess the steady state rate of proliferation in response to chronic CAPs exposure in the various organs from the different cohorts. Similarly, TUNEL analyses will be performed to determine the steady state rate of apoptosis.

The steady state level of the lung and the circulating pro-inflammatory cytokines including IL-1β, IL-2, IL-4, IL-5, IL-6, IL-10, IL-12 (p70), TNFα, IFNγ and GM-CSF will be quantitatively determinde using the Upstate Beadlyte®/Luminex® multiplex mouse multi-cytokine detection system which allowed for sensitive and accurate measurement of all the above cytokine simultaneously in a small volume of serum.

As the temporal relationship between environmental exposure to CAPs and oncogene activation might be important to lung tumorigenesis and progression. Thus, the experiments described above will be repeated in a different temporal sequence. Using the same cohorts of animals as described above, animals in the different cohorts we be chronically exposed the either to CAPs or filtered air starting at 3 weeks of age. After 20 weeks of exposure, all the mice will be placed on filtered air, and the mice in 2, 2a, and 2b will be put on continuous doxycycline diet. This set of experiment will address the impact of existing chronic lung inflammation caused by environmental insult (CAPs) on oncogene-driven lung tumorigenesis.

Lastly, if there are major differences in the between the CAPs exposed mouse cohorts and the control cohorts in either the latency, aggressiveness or the histology of lung tumors, the tumors from each of the cohorts will be isolated and similar expression profiling analyses will be performed as detailed above to determine the pathways that are deregulated as a result of the CAPs exposure.

REFERENCES

1. Hearle, N. et al. Frequency and spectrum of cancers in the Peutz-Jeghers syndrome. *Clin Cancer Res* 12, 3209-15 (2006).
2. Carretero, J., Medina, P. P., Pio, R., Montuenga, L. M. & Sanchez-Cespedes, M. Novel and natural knockout lung cancer cell lines for the LKB1/STK11 tumor suppressor gene. *Oncogene* 23, 4037-40 (2004).
3. Sanchez-Cespedes, M. et al. Inactivation of LKB1/STK11 is a common event in adenocarcinomas of the lung. *Cancer Res* 62, 3659-62 (2002).
4. Avizienyte, E. et al. LKB1 somatic mutations in sporadic tumors. Am J Pathol 154, 677-81 (1999).
5. *Pathology and Genetics of Tumours of the Lung, Pleura, Thymus and Heart* (ed. William D. Travis, E. B., H. Konrad Muller-Hermelink, Curtis C. Harris) (IARC Press, Lyon, 2004).
6. Forbes, S. et al. Cosmic 2005. *Br J Cancer* 94, 318-22 (2006).
7. Launonen, V. Mutations in the human LKB1/STK11 gene. *Hum Mutat* 26, 291-7 (2005).
8. Carretero, J. et al. Dysfunctional AMPK activity, signalling through mTOR and survival in response to energetic stress in LKB1-deficient lung cancer. *Oncogene* (2006).
9. Shaw, R. J. et al. The LKB1 tumor suppressor negatively regulates mTOR signaling. *Cancer Cell* 6, 91-9 (2004).
10. Corradetti, M. N., Inoki, K., Bardeesy, N., DePinho, R. A. & Guan, K. L. Regulation of the TSC pathway by LKB1: evidence of a molecular link between tuberous sclerosis complex and Peutz-Jeghers syndrome. *Genes Dev* 18, 1533-8 (2004).
11. Tiainen, M., Vaahtomeri, K., Ylikorkala, A. & Makela, T. P. Growth arrest by the LKB1 tumor suppressor: induction of p21 (WAF1/CIP1). *Hum Mol Genet* 11, 1497-504 (2002).
12. Karuman, P. et al. The Peutz-Jegher gene product LKB1 is a mediator of p53-dependent cell death. *Mol Cell* 7, 1307-19 (2001).
13. Upadhyay, S. et al. LKB1/STK11 Suppresses Cyclooxygenase-2 Induction and Cellular Invasion through PEA3 in Lung Cancer. *Cancer Res* 66, 7870-9 (2006).
14. Zhong, D. et al. LKB1 mutation in large cell carcinoma of the lung. *Lung Cancer* (2006).
15. Bardeesy, N. et al. Loss of the Lkb1 tumour suppressor provokes intestinal polyposis but resistance to transformation. *Nature* 419, 162-7 (2002).
16. Entius, M. M. et al. Peutz-Jeghers polyps, dysplasia, and K-ras codon 12 mutations. *Gut* 41, 320-2 (1997).
17. Entius, M. M. et al. Molecular genetic alterations in hamartomatous polyps and carcinomas of patients with Peutz-Jeghers syndrome. *J Pathol* 54, 126-31 (2001).
18. Gruber, S. B. et al. Pathogenesis of adenocarcinoma in Peutz-Jeghers syndrome, *Cancer Res* 58, 5267-70 (1998).
19. Jackson, E. L. et al, Analysis of lung tumor initiation and progression using conditional expression of oncogenic K-ras. *Genes Dev* 15, 3243-8 (2001).
20. Jonkers, J. et al. Synergistic tumor suppressor activity of BRCA2 and p53 in a conditional mouse model for breast cancer. *Nat Genet* 29, 418-25 (2001).
21. Serrano, M. et al. Role of the INK4a locus in tumor suppression and cell mortality. *Cell* 85, 27-37 (1996).
22. Sharpless, N. E. et al. Loss of p16Ink4a with retention of p19Arf predisposes mice to tumorigenesis, *Nature* 413, 86-91 (2001).
23. Ji, H. et al. K-ras activation generates an inflammatory response in lung tumors. *Oncogene* (2005).
24. Johnson, L. et al. Somatic activation of the K-ras oncogene causes early onset lung cancer in mice. *Nature* 410, 1111-6 (2001).
25. Meuwissen, R., Linn, S. C., van der Valk, M., Mooi, W. J, & Berns, A. Mouse model for lung tumorigenesis through Cre/lox controlled sporadic activation of the K-Ras oncogene. *Oncogene* 20, 6551-8 (2001).
26. Fisher, G. H. et al. induction and apoptotic regression of lung adenocarcinomas by regulation of a K-Ras transgene in the presence and absence of tumor suppressor genes. *Genes Dev* 15, 3249-62 (2001).
27. Jackson, E. L. et al. The differential effects of mutant p53 alleles on advanced murine lung cancer. *Cancer Res* 65, 10280-8 (2005).
28. Meuwissen, R. et al. Induction of small cell lung cancer by somatic inactivation of both Trp53 and Rb1 in a conditional mouse model. *Cancer Cell* 4, 181-9 (2003).
29. Young, G. D. et al. Differential expression and biodistribution of cytokeratin 18 and desmoplakins in non-small cell lung carcinoma subtypes. *Lung Cancer* 36, 133-41 (2002).
30. Camilo, R., Capelozzi, V. L., Siqueira, S. A. & Del Carlo Bernardi, F. Expression of p63, keratin 5/6, keratin 7, and surfactant-A in non-small cell lung carcinomas. *Hum Pathol* 37, 542-6 (2006).
31. Raponi, M. et al. Gene expression signatures for predicting prognosis of squamous cell and adenocarcinomas of the lung. *Cancer Res* 66, 7466-72 (2006).

32. Dennis, G., Jr. et at. DAVID: Database for Annotation, Visualization, and Integrated Discovery. *Genome Biol* 4, P3 (2003).

33. Hardie, D. G. New roles for the LKB1-->AMPK pathway. *Curr Opin Cell Biol* 17, 167-73 (2005).

34. Brugarolas, J. et al. Regulation of mTOR function in response to hypoxia by REDD1 and the TSC1/TSC2 tumor suppressor complex. *Genes Dev* 18, 2893-904 (2004).

35. Fernandez, P. et al. Distinctive gene expression of human lung adenocarcinomas carrying LKB1 mutations. *Oncogene* 23, 5084-91 (2004).

36. Ji, H. et al. K-ras activation generates an inflammatory response in lung tumors. *Oncogene* 25, 2105-12 (2006).

37. Ji, H. et al. The impact of human EGFR kinase domain mutations on lung tumorigenesis and in vivo sensitivity to EGFR-targeted therapies. *Cancer Cell* 9, 485-95 (2006).

38. Sharpless, N. E., Ramsey, M. R., Balasubramanian, P., Castrillon, D. H. & DePinho, R. A. The differential impact of p16 (INK4a) or p19 (ARF) deficiency on cell growth and tumorigenesis. *Oncogene* 23, 379-85 (2004).

39. Krishnamurthy, J. et al. Ink4a/Arf expression is a biomarker of aging. *J Clin Invest* 114, 1299-307 (2004).

40. Irizarry, R. A. et al. Exploration, normalization, and summaries of high density oligonucleotide array probe level data. *Biostatistics* 4, 249-64 (2003).

41. Bolstad, B. M., Irizarry, R. A., Astrand, M. & Speed, T. P. A comparison of normalization methods for high density oligonucleotide array data based on variance and bias. *Bioinformatics* 19, 185-93 (2003).

42. Irizarry, R. A. et al. Summaries of Affymetrix GeneChip probe level data. *Nucleic Acids Res* 31, e15 (2003).

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating a human subject with a non-small cell lung cancer (NSCLC), comprising:
   providing an NSCLC sample obtained from the human subject;
   detecting a level of Lkb1 activity in the human subject-derived NSCLC sample and a level of Lkb1 activity in a normal sample;
   detecting activated K-ras in the human subject-derived NSCLC sample; and
   administering an mTor inhibitor to the human subject if the level of Lkb1 activity in the subject-derived NSCLC sample is reduced compared to the level in the normal sample and activated K-ras is detected.

2. The method of claim 1, wherein the subject-derived NSCLC sample is a tumor biopsy.

3. The method of claim 1, wherein detecting the levels of Lkb1 activity in the human subject-derived NSCLC sample and the normal sample comprises detecting a level of Lkb1 nucleic acid or protein.

4. The method of claim 3, wherein the level of Lkb1 protein is detected using an immunoassay.

5. The method of claim 3, wherein the level of Lkb1 nucleic acid is detected using Northern hybridization analysis comprising at least one probe that binds to an Lkb1 sequence, or reverse transcriptase (RT)-PCR.

6. The method of claim 1, wherein the level of Lkb1 activity is reduced when the level of Lkb1 nucleic acid or protein in the human subject-derived NSCLC sample is statistically significantly less than the level of nucleic acid or protein in the normal sample.

7. The method of claim 6, wherein the level of Lkb1 nucleic acid or protein is statistically significantly less in the human subject-derived NSCLC sample when the probability that the difference in the levels of Lkb1 nucleic acid or protein between the two samples occurred by random chance is less than or equal to 0.05.

8. The method of claim 1, wherein detecting the level of Lkb1 activity in the human subject-derived NSCLC sample comprises detecting a sequence of an Lkb1 nucleic acid in the subject-derived NSCLC sample.

9. The method of claim 8, wherein the level of Lkb1 activity is reduced when the Lkb1 nucleic acid sequence comprises an inactivating mutation.

10. The method of claim 9, wherein the inactivating mutation inactivates Lkb1 kinase activity.

11. The method of claim 9, wherein the inactivating mutation comprises a disruption of the Lkb1 coding sequence, an insertion of one or more stop codons in the Lkb1 coding sequence, an insertion of a DNA fragment, a deletion of coding sequence or a substitution of a stop codon for coding sequence.

12. The method of claim 9, wherein the inactivating mutation comprises a mutation at amino acid residue 78 of the Lkb1 protein.

13. The method of claim 1, wherein the NSCLC is squamous carcinoma, large cell carcinoma, adenocarcinoma or a mixed tumor.

14. The method of claim 1, wherein detecting the activation of K-ras comprises detecting one or more mutations in K-ras comprising a glycine to aspartic acid substitution at amino acid 12 of the K-ras protein (K-ras$_{G12D}$).

15. The method of claim 1, wherein the mTor inhibitor is rapamycin.

* * * * *

SEQUENCE LISTING

```
<160> NUMBER OF SEQ ID NOS: 2

<210> SEQ ID NO 1
<211> LENGTH: 3286
<212> TYPE: DNA
<213> ORGANISM: Homo sapiens

<400> SEQUENCE: 1
gcgtgtcggg cgcggaaggg ggaggcggcc cggggcgccc gcgagtgagg cgcggggcgg      60
cgaagggagc gcgggtggcg gcacttgctg ccgcggcctt ggatgggctg ggccccctc     120 gccgctccgc ctcctccaca cgcgcggcgg ccgcggcgag ggggacgcgc cgcccggggc    180 ccggcaccttt cgggaacccc ccggcccgga gcctgcggcc tgcgccgcct cggccgccgg   240 gagcccgtg gagcccccgc cgccgcgccg ccccgcggac cggacgctga gggcactcgg     300
ggcggggcgc gcgctcgggc agacgtttgc ggggaggggg gcgcctgccg ggccccggcg    360
accaccttgg gggtcgcggg ccggctcggg gggcgcccag tgcgggccct cgcgggcgcc    420
gggcagcgac cagccctgag cggagctgtt ggccgcggcg ggaggcctcc cggacgcccc    480
cagccccccg aacgctcgcc cgggccggcg ggagtcggcg cccccggga ggtccgctcg     540 gtcgtccgcg gcggagcgtt tgctcctggg acaggcggtg ggaccggggc gtcgccggag    600 acgccccag cgaagttggg ctctccaggt gtgggggtcc cgggggggtag cgacgtcgcg    660 gacccggcct gtgggatggg cggcccggag aagactgcgc tcggccgtgt tcatacttgt    720
ccgtgggcct gaggtccccg gaggatgacc tagcactgaa aagcccggc cggcctcccc     780 agggtccccg aggacgaagt tgaccctgac cgggccgtct cccagttctg aggcccgggt    840
cccactggaa ctcgcgtctg agccgccgtc ccggaccccc ggtgcccgcc ggtccgcaga    900
ccctgcaccg ggcttggact cgcagccggg actgacgtgt agaacaatcg tttctgttgg    960 aagaagggt tttcccttcc ttttggggtt tttgttgcct ttttttttc ttttttcttt    1020 gtaaaatttt ggagaaggga agtcggaaca caaggaagga ccgctcaccc gcggactcag   1080
ggctggcggc gggactccag gaccctgggt ccagcatgga ggtggtggac ccgcagcagc   1140
tgggcatgtt cacggagggc gagctgatgt cggtgggtat ggacacgttc atccaccgca   1200
tcgactccac cgaggtcatc taccagccgc gccgcaagcg ggccaagctc atcggcaagt   1260
```

-continued

```
acctgatggg ggacctgctg ggggaaggct cttacggcaa ggtgaaggag gtgctggact    1320
cggagacgct gtgcaggagg gccgtcaaga tcctcaagaa gaagaagttg cgaaggatcc    1380
ccaacgggga ggccaacgtg aagaaggaaa ttcaactact gaggaggtta cggcacaaaa    1440
atgtcatcca gctggtggat gtgttataca acgaagagaa gcagaaaatg tatatggtga    1500
tggagtactg cgtgtgtggc atgcaggaaa tgctggacag cgtgccggag aagcgtttcc    1560
cagtgtgcca ggcccacggg tacttctgtc agctgattga cggcctggag tacctgcata    1620
gccagggcat tgtgcacaag gacatcaagc cggggaacct gctgctcacc accggtggca    1680
ccctcaaaat ctccgacctg gcgtggccg aggcactgca cccgttcgcg gcggacgaca    1740
cctgccggac cagccagggc tccccggctt ccagccgcc cgagattgcc aacggcctgg    1800
acaccttctc cggcttcaag gtggacatct ggtcggctgg ggtcaccctc tacaacatca    1860
ccacgggtct gtaccccttc aaggggaca acatctacaa gttgtttgag aacatcggga    1920
aggggagcta cgccatcccg ggcgactgtg gcccccgct ctctgacctg ctgaaaggga    1980
tgcttgagta cgaaccggcc aagaggttct ccatccggca gatccggcag cacagctggt    2040
tccggaagaa acatcctccg gctgaagcac cagtgcccat cccaccgagc ccagacacca    2100
aggaccggtg gcgcagcatg actgtggtgc cgtacttgga ggacctgcac ggcgcggacg    2160
aggacgagga cctcttcgac atcgaggatg acatcatcta cactcaggac ttcacggtgc    2220
ccggacaggt cccagaagag gaggccagtc acaatggaca cgccggggc ctccccaagg    2280 ccgtgtgtat gaacggcaca gaggcggcgc agctgagcac caaatccagg cggagggcc    2340 gggcccccaa ccctgcccgc aaggcctgct ccgccagcag caagatccgc cggctgtcgg    2400
cctgcaagca gcagtgaggc tggccgcctg cagcccgtgt ccaggagccc gccaggtgc    2460 ccgcgccagg ccctcagtct tcctgccggt tccgcccgcc ctcccggaga ggtggccgcc    2520
atgcttctgt gccgaccacg ccccaggacc tccggagcgc cctgcagggc cgggcagggg    2580
gacagcaggg accgggcgca gccctccccc ctcggccgcc cggcagtgca cgcggcttgt    2640
tgacttcgca gccccgggcg gagccttccc gggcgggcgt gggaggaggg aggcggcctc    2700
catgcacttt atgtggagac tactggcccc gccgtggcc tcgtgctccg cagggcgccc    2760
agcgccgtcc ggcggcccg ccgcagacca gctggcgggt gtggagacca ggctcctgac    2820
cccgccatgc atgcagcgcc acctggaagc cgcgcggccg ctttggtttt ttgtttggtt    2880
ggttccattt tctttttttc tttttttttt taagaaaaaa taaaaggtgg atttgagctg    2940
tggctgtgag gggtgtttgg gagctgctgg gtggcagggg ggctgtgggg tcgggctcac    3000
gtcgcggccg cctttgcgct ctcgggtcac cctgctttgg cggcccggcc ggagggcagg    3060
accctcacct ctccccaag gccactgcgc tcttgggacc ccagagaaaa cccgagcaa    3120 gcaggagtgt gcggtcaata tttatatcat ccagaaaaga aaaacacgag aaacgccatc    3180
gcgggatggt gcagacgcgg cggggactcg gagggtgccg tgcgggcgag gccgcccaaa    3240
tttggcaata aataaagctt gggaagcttg gacctgaaaa aaaaaa                  3286
```

<210> SEQ ID NO 2
<211> LENGTH: 433
<212> TYPE: PRT
<213> ORGANISM: Homo sapiens

<400> SEQUENCE: 2

```
Met Glu Val Val Asp Pro Gln Gln Leu Gly Met Phe Thr Glu Gly Glu
1               5                   10                  15
```

-continued

```
Leu Met Ser Val Gly Met Asp Thr Phe Ile His Arg Ile Asp Ser Thr
            20                  25                  30

Glu Val Ile Tyr Gln Pro Arg Arg Lys Arg Ala Lys Leu Ile Gly Lys
            35                  40                  45

Tyr Leu Met Gly Asp Leu Leu Gly Glu Gly Ser Tyr Gly Lys Val Lys
 50                  55                  60

Glu Val Leu Asp Ser Glu Thr Leu Cys Arg Arg Ala Val Lys Ile Leu
 65                  70                  75                  80

Lys Lys Lys Lys Leu Arg Arg Ile Pro Asn Gly Glu Ala Asn Val Lys
                85                  90                  95

Lys Glu Ile Gln Leu Leu Arg Arg Leu Arg His Lys Asn Val Ile Gln
            100                 105                 110

Leu Val Asp Val Leu Tyr Asn Glu Glu Lys Gln Lys Met Tyr Met Val
            115                 120                 125

Met Glu Tyr Cys Val Cys Gly Met Gln Glu Met Leu Asp Ser Val Pro
            130                 135                 140

Glu Lys Arg Phe Pro Val Cys Gln Ala His Gly Tyr Phe Cys Gln Leu
145                 150                 155                 160

Ile Asp Gly Leu Glu Tyr Leu His Ser Gln Gly Ile Val His Lys Asp
                165                 170                 175

Ile Lys Pro Gly Asn Leu Leu Leu Thr Thr Gly Gly Thr Leu Lys Ile
            180                 185                 190

Ser Asp Leu Gly Val Ala Glu Ala Leu His Pro Phe Ala Ala Asp Asp
            195                 200                 205

Thr Cys Arg Thr Ser Gln Gly Ser Pro Ala Phe Gln Pro Pro Glu Ile
            210                 215                 220

Ala Asn Gly Leu Asp Thr Phe Ser Gly Phe Lys Val Asp Ile Trp Ser
225                 230                 235                 240

Ala Gly Val Thr Leu Tyr Asn Ile Thr Thr Gly Leu Tyr Pro Phe Glu
                245                 250                 255

Gly Asp Asn Ile Tyr Lys Leu Phe Glu Asn Ile Gly Lys Gly Ser Tyr
            260                 265                 270

Ala Ile Pro Gly Asp Cys Gly Pro Pro Leu Ser Asp Leu Leu Lys Gly
            275                 280                 285

Met Leu Glu Tyr Glu Pro Ala Lys Arg Phe Ser Ile Arg Gln Ile Arg
            290                 295                 300

Gln His Ser Trp Phe Arg Lys Lys His Pro Pro Ala Glu Ala Pro Val
305                 310                 315                 320

Pro Ile Pro Pro Ser Pro Asp Thr Lys Asp Arg Trp Arg Ser Met Thr
                325                 330                 335

Val Val Pro Tyr Leu Glu Asp Leu His Gly Ala Asp Glu Asp Glu Asp
            340                 345                 350

Leu Phe Asp Ile Glu Asp Asp Ile Ile Tyr Thr Gln Asp Phe Thr Val
            355                 360                 365

Pro Gly Gln Val Pro Glu Glu Glu Ala Ser His Asn Gly Gln Arg Arg
            370                 375                 380

Gly Leu Pro Lys Ala Val Cys Met Asn Gly Thr Glu Ala Ala Gln Leu
385                 390                 395                 400

Ser Thr Lys Ser Arg Ala Glu Gly Arg Ala Pro Asn Pro Ala Arg Lys
                405                 410                 415
```

```
Ala Cys Ser Ala Ser Ser Lys Ile Arg Arg Leu Ser Ala Cys Lys Gln
            420                 425                 430
Gln
```